US008328765B2

(12) United States Patent
Daily et al.

(10) Patent No.: US 8,328,765 B2
(45) Date of Patent: *Dec. 11, 2012

(54) AUTOMATIC NEEDLE DEVICE

(75) Inventors: David Daily, Herzliya (IL); Lior Raday, D. N. Hof Ashkelon (IL)

(73) Assignee: Dali Medical Devices Ltd., Herzliya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/040,520

(22) Filed: Mar. 4, 2011

(65) Prior Publication Data
US 2011/0152783 A1    Jun. 23, 2011

Related U.S. Application Data

(63) Continuation of application No. 10/572,215, filed as application No. PCT/IL2004/000852 on Sep. 15, 2004, now Pat. No. 7,901,382.

(30) Foreign Application Priority Data

Sep. 17, 2003  (IL) ............................................. 157984

(51) Int. Cl.
*A61M 5/32* (2006.01)
(52) U.S. Cl. ....................................... 604/192; 604/198
(58) Field of Classification Search .................. 604/192, 604/198, 187, 137, 131, 156, 263
See application file for complete search history.

(56) References Cited

U.S. PATENT DOCUMENTS

| | | | |
|---|---|---|---|
| 4,333,457 A | 6/1982 | Margulies | |
| 4,592,742 A | 6/1986 | Landau | |
| 4,623,332 A | 11/1986 | Lindmayer et al. | |
| 4,902,279 A | 2/1990 | Schmidtz et al. | |
| 4,998,918 A | 3/1991 | Mimura | |
| 5,092,842 A | 3/1992 | Bechtold et al. | |
| 5,137,516 A | 8/1992 | Rand et al. | |
| 5,215,536 A | 6/1993 | Lampropoulos et al. | |
| 5,267,963 A | 12/1993 | Bachynsky | |
| 5,295,965 A | 3/1994 | Wilmot | |
| 5,300,030 A | 4/1994 | Crossman et al. | |

(Continued)

FOREIGN PATENT DOCUMENTS

CA    2356614 A1    4/2000

(Continued)

OTHER PUBLICATIONS

An examination report dated Jul. 30, 2012, which issued during prosecution of Applicant's European Application No. 04 770 523.1.

(Continued)

*Primary Examiner* — Kevin C Sirmons
*Assistant Examiner* — Deanna K Hall
(74) *Attorney, Agent, or Firm* — Fish & Richardson P.C.

(57) ABSTRACT

An automatic needle device including a housing element, at least one resilient element arranged to be located within the housing element, at least one needle bearing element adapted, when actuated, to be displaced by the at least one resilient element with respect to the housing element from a non-penetration position to a penetration position and a needle guard adapted for positioning with respect to the housing element and wherein displacement of the needle guard is operative to actuate displacement of the at least one needle bearing element from the non-penetration position to the penetration position.

19 Claims, 82 Drawing Sheets

U.S. PATENT DOCUMENTS

| | | |
|---|---|---|
| 5,320,609 A | 6/1994 | Haber et al. |
| 5,478,316 A | 12/1995 | Bitdinger et al. |
| 5,527,287 A | 6/1996 | Miskinyar |
| 5,584,815 A | 12/1996 | Pawelka et al. |
| 5,599,309 A | 2/1997 | Marshall et al. |
| 5,616,128 A | 4/1997 | Meyer |
| 5,665,071 A | 9/1997 | Wyrick |
| 5,681,291 A | 10/1997 | Galli |
| 5,695,472 A | 12/1997 | Wyrick |
| 5,779,677 A | 7/1998 | Frezza |
| 5,823,998 A | 10/1998 | Yamagata |
| 5,957,897 A | 9/1999 | Jeffrey |
| 6,015,396 A | 1/2000 | Buttgen et al. |
| 6,070,623 A | 6/2000 | Aneas |
| 6,099,503 A | 8/2000 | Stradella |
| 6,099,504 A | 8/2000 | Gross et al. |
| 6,149,626 A | 11/2000 | Bachynsky et al. |
| 6,159,181 A | 12/2000 | Crossman et al. |
| 6,241,708 B1 | 6/2001 | Reilly et al. |
| 6,280,421 B1 | 8/2001 | Kirchhofer et al. |
| 6,319,233 B1 | 11/2001 | Jansen et al. |
| 6,387,078 B1 | 5/2002 | Gillespie |
| 6,530,903 B2 | 3/2003 | Wang et al. |
| 6,544,234 B1 | 4/2003 | Gabriel |
| 6,565,553 B2 | 5/2003 | Sadowski et al. |
| 6,572,590 B1 | 6/2003 | Stevens et al. |
| 6,585,690 B1 | 7/2003 | Hoeck et al. |
| 6,592,555 B1 | 7/2003 | Wen et al. |
| 6,595,962 B1 | 7/2003 | Perthu |
| 6,607,508 B2 | 8/2003 | Knauer |
| 6,613,019 B2 | 9/2003 | Munk |
| 6,620,137 B2 | 9/2003 | Kirchhofer et al. |
| 6,638,255 B1 | 10/2003 | Weber |
| 6,673,049 B2 | 1/2004 | Hommann et al. |
| 6,685,676 B2 | 2/2004 | Jansen et al. |
| 6,971,999 B2 | 12/2005 | Py et al. |
| 7,901,382 B2 * | 3/2011 | Daily et al. .................. 604/187 |
| 2001/0037087 A1 | 11/2001 | Knauer |
| 2002/0133122 A1 * | 9/2002 | Giambattista et al. ........ 604/198 |
| 2003/0093036 A1 | 5/2003 | Crossman et al. |
| 2003/0105430 A1 | 6/2003 | Lavi et al. |

FOREIGN PATENT DOCUMENTS

| | | |
|---|---|---|
| EP | 1034809 A1 | 9/2000 |
| FR | 2770404 B1 | 1/2000 |
| WO | WO9903529 A2 | 1/1999 |
| WO | WO0224259 A3 | 6/2002 |
| WO | WO03047663 A2 | 6/2003 |
| WO | WO2005025636 A2 | 3/2005 |
| WO | WO2005025637 A2 | 3/2005 |
| WO | WO2005086587 A2 | 9/2005 |
| WO | WO2004060445 A3 | 4/2006 |
| WO | WO2008047372 A2 | 4/2008 |

OTHER PUBLICATIONS

US 5,954,699, 09/1999, Jost et al. (withdrawn)

* cited by examiner

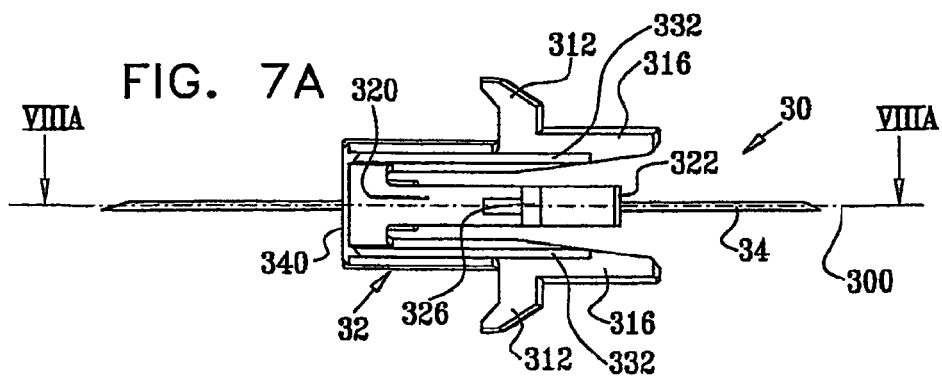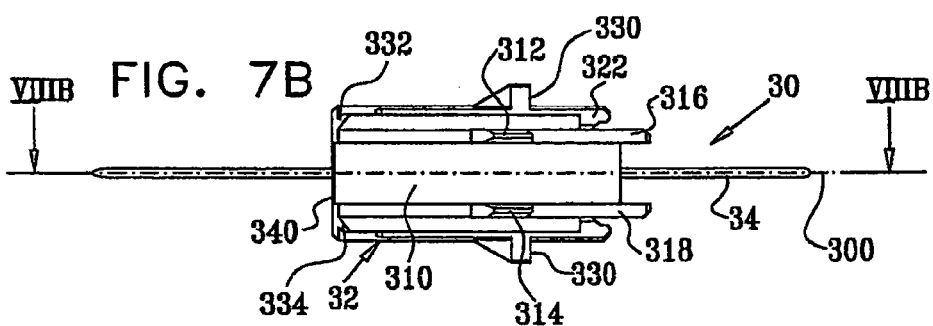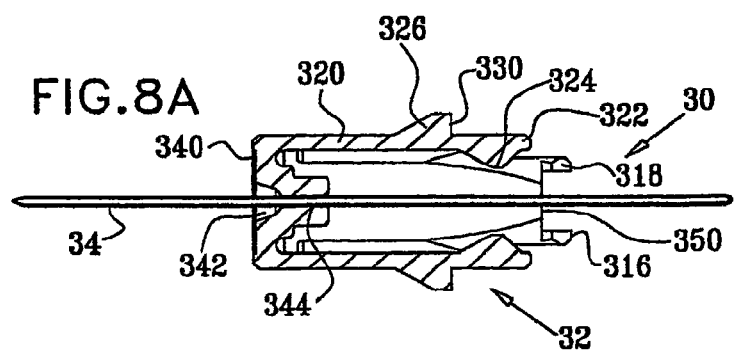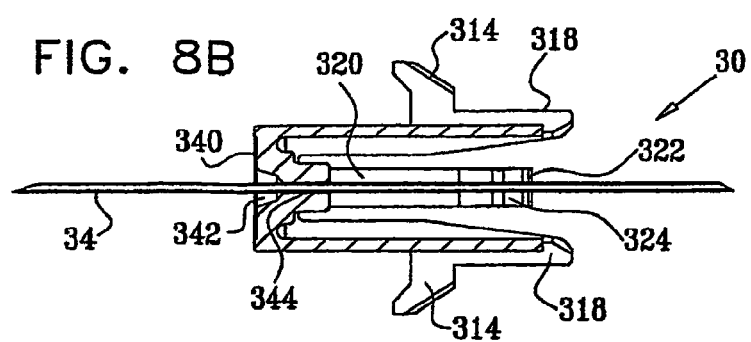

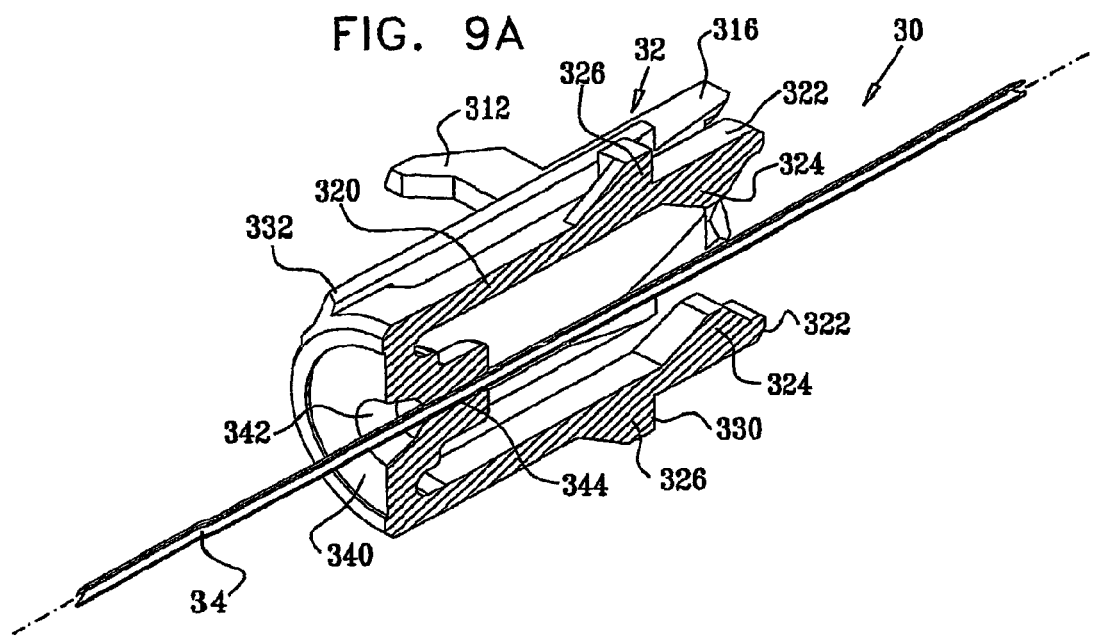
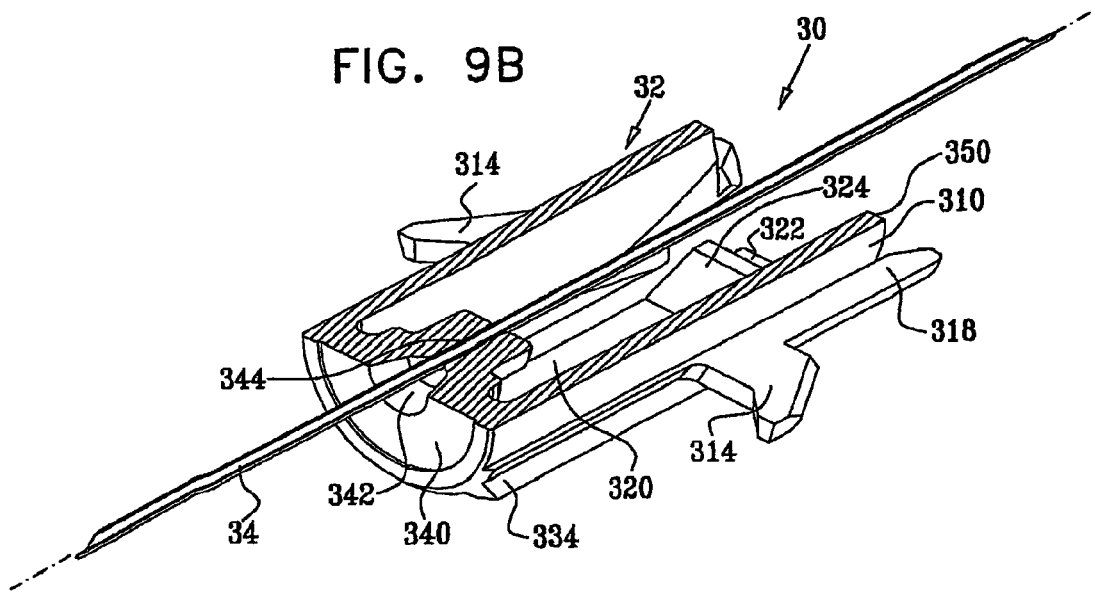

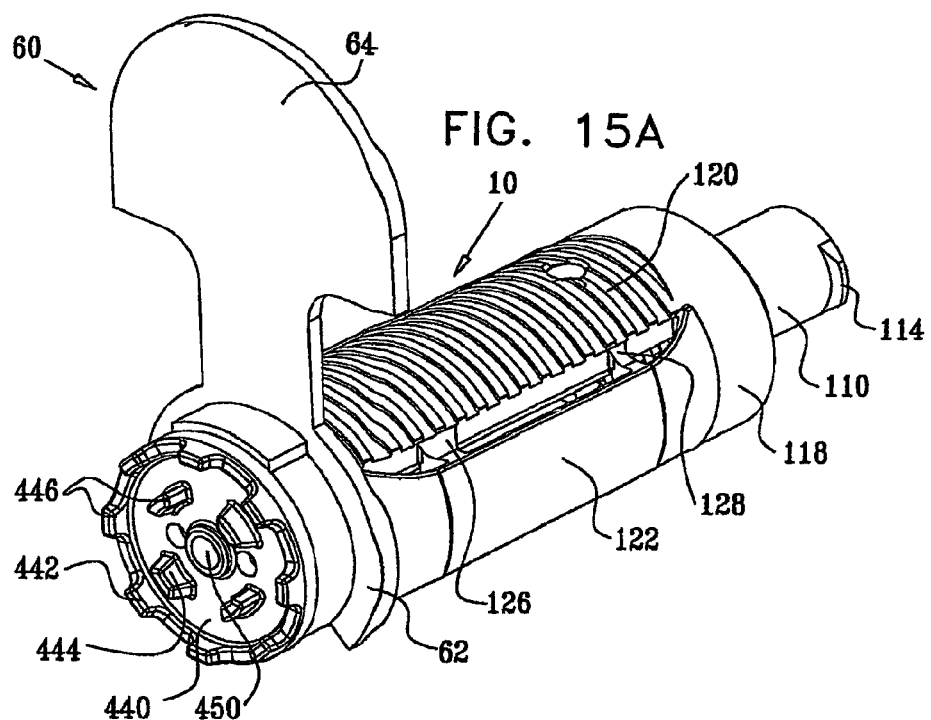
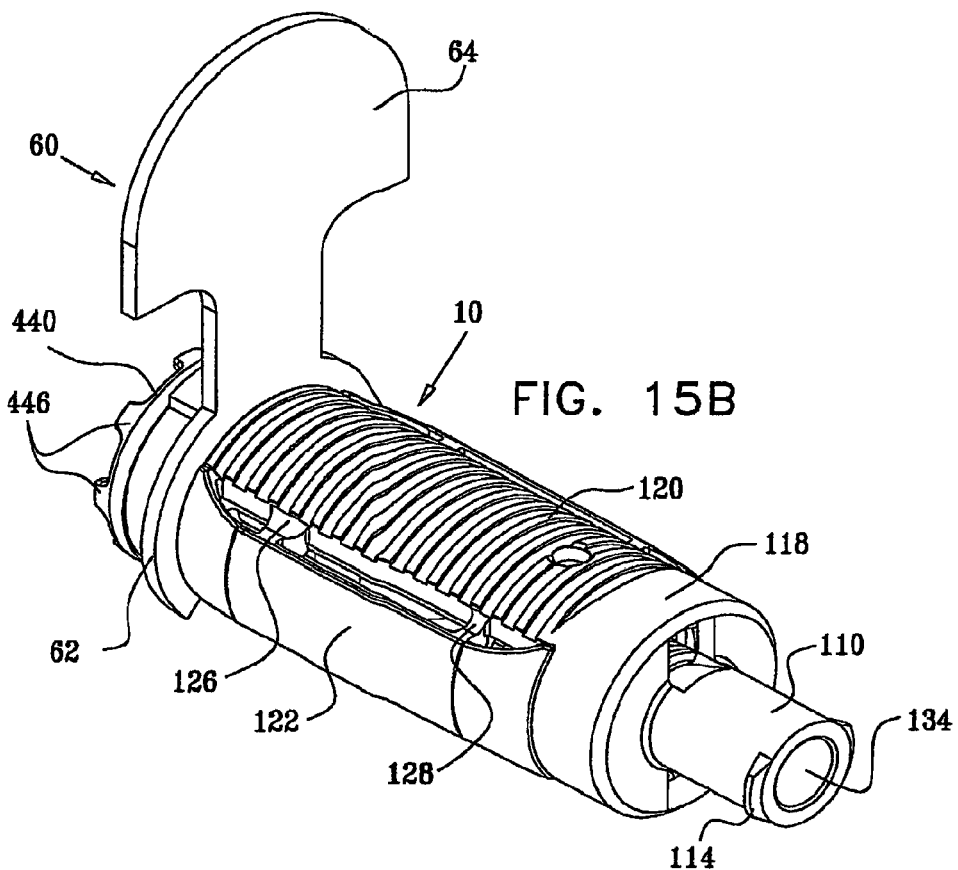

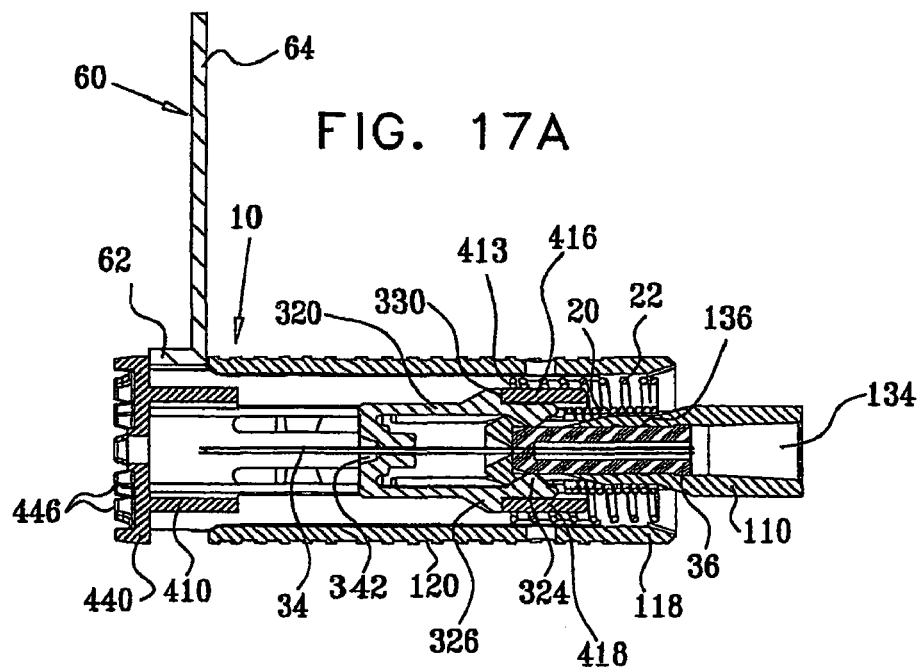
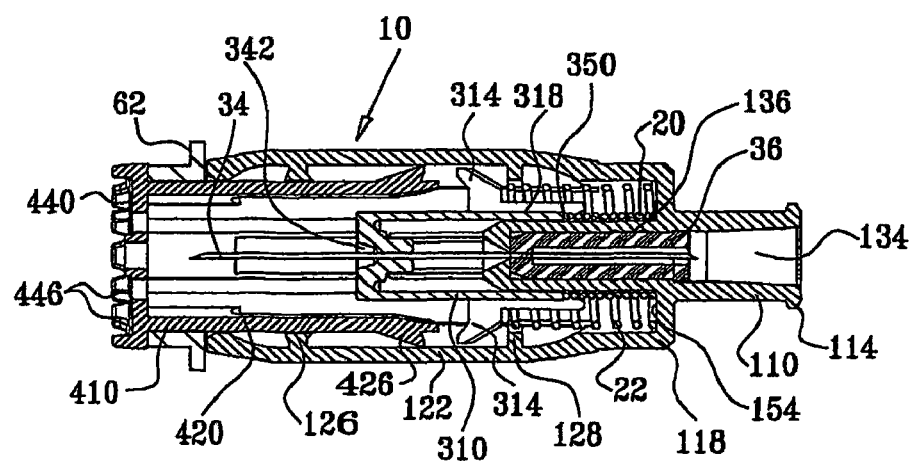

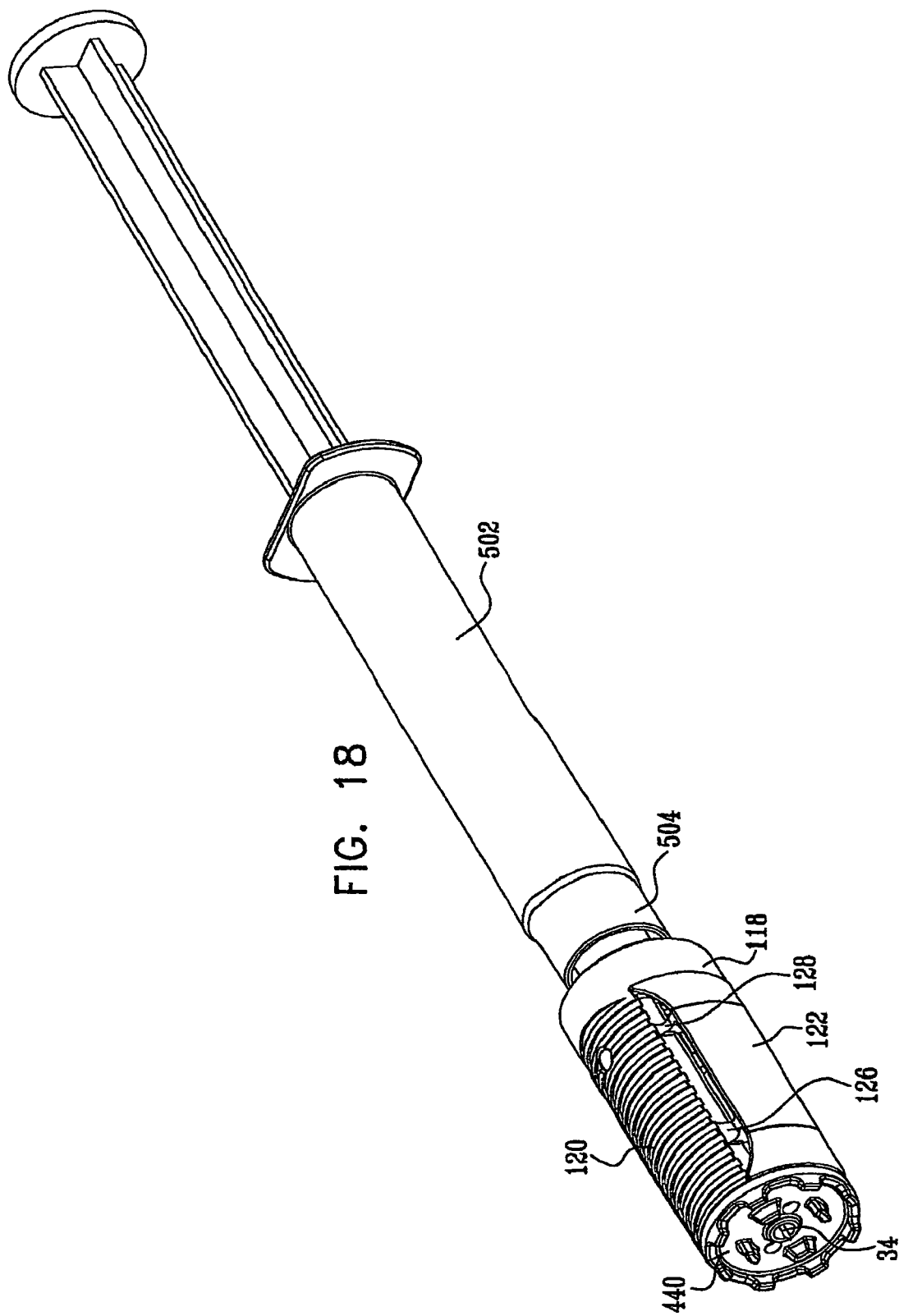

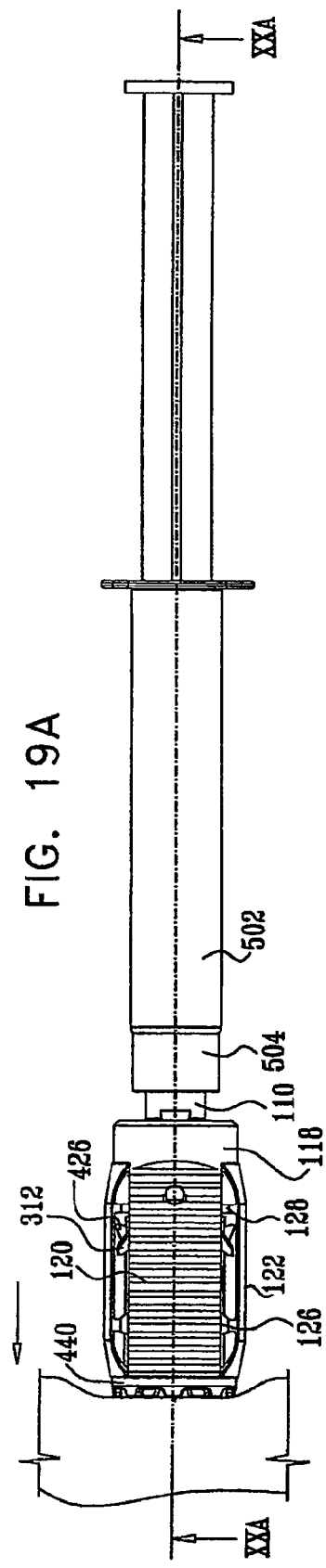
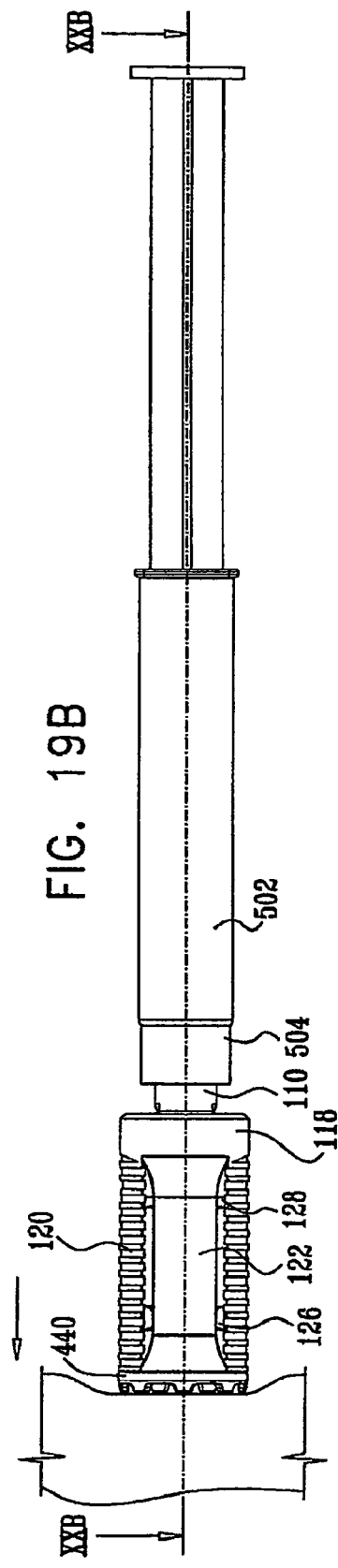

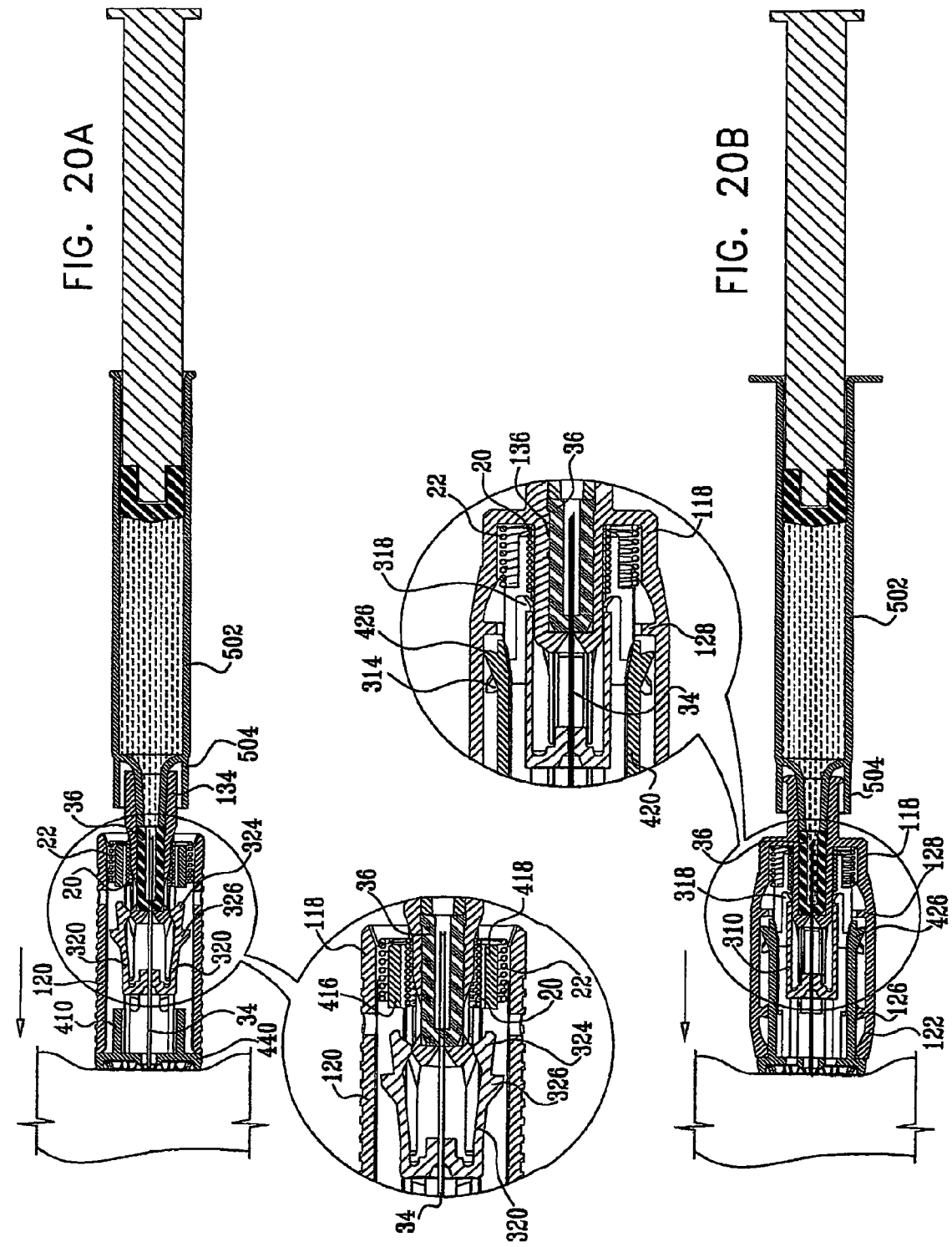

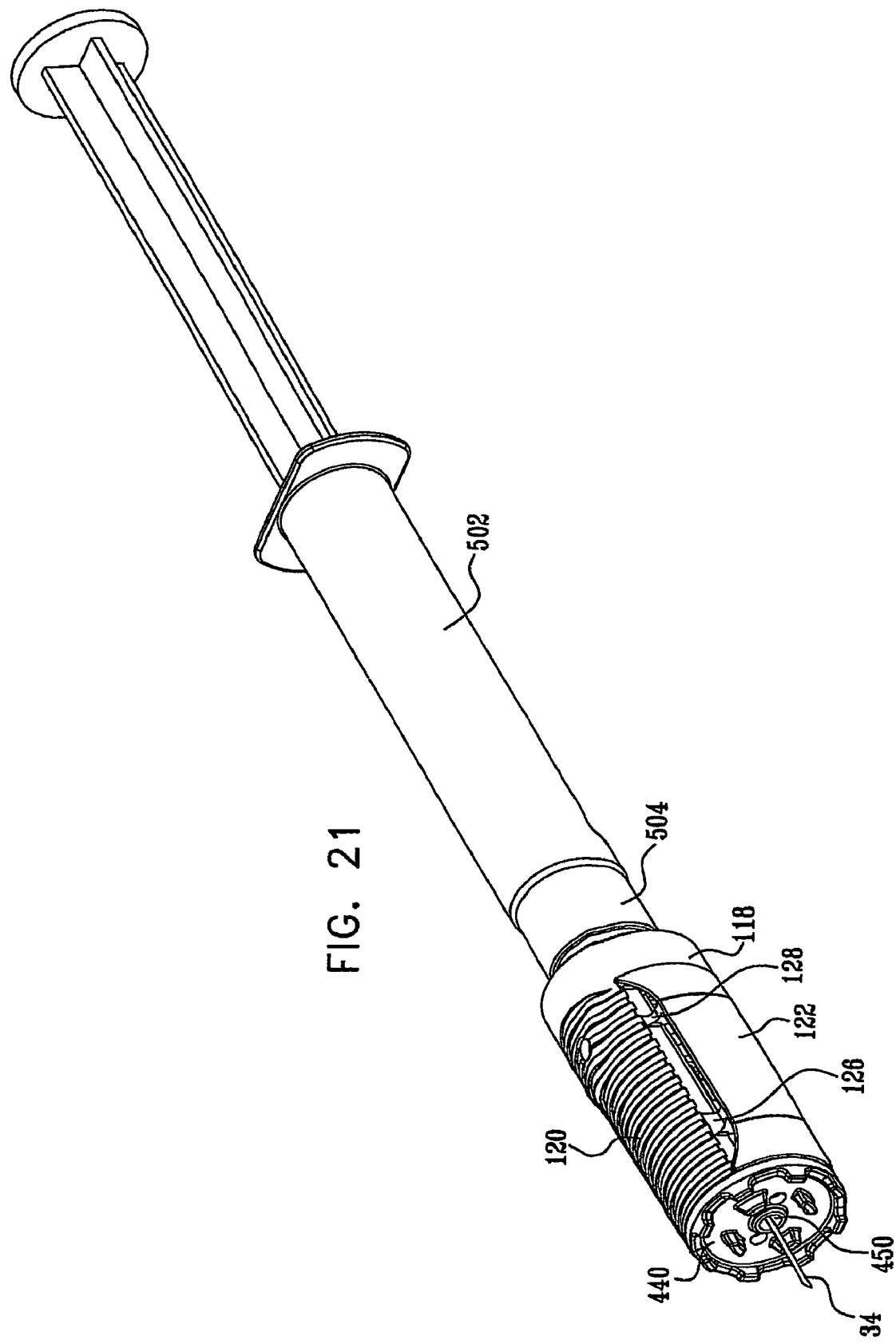

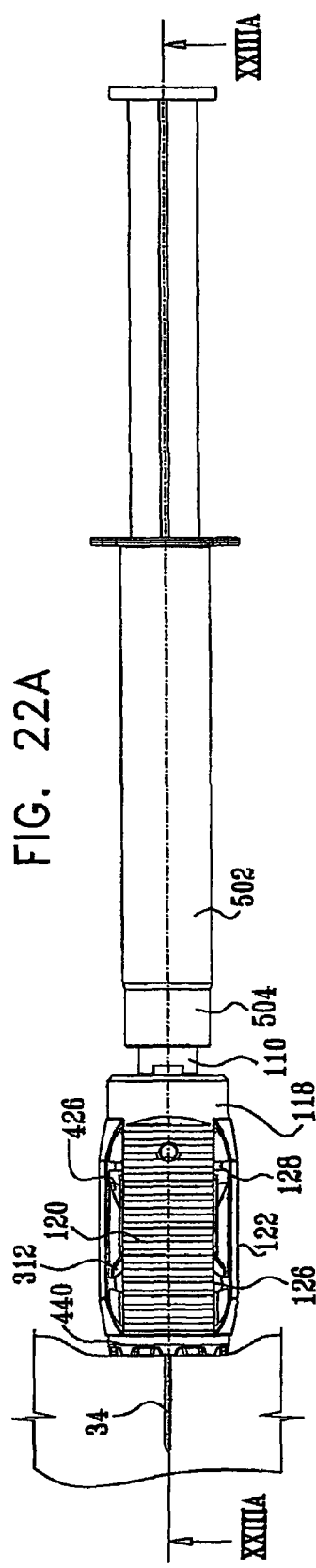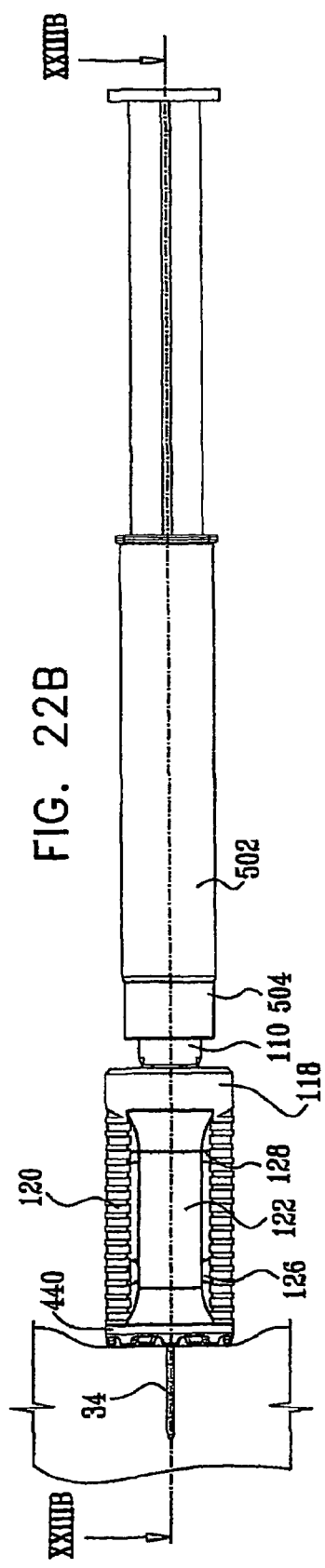

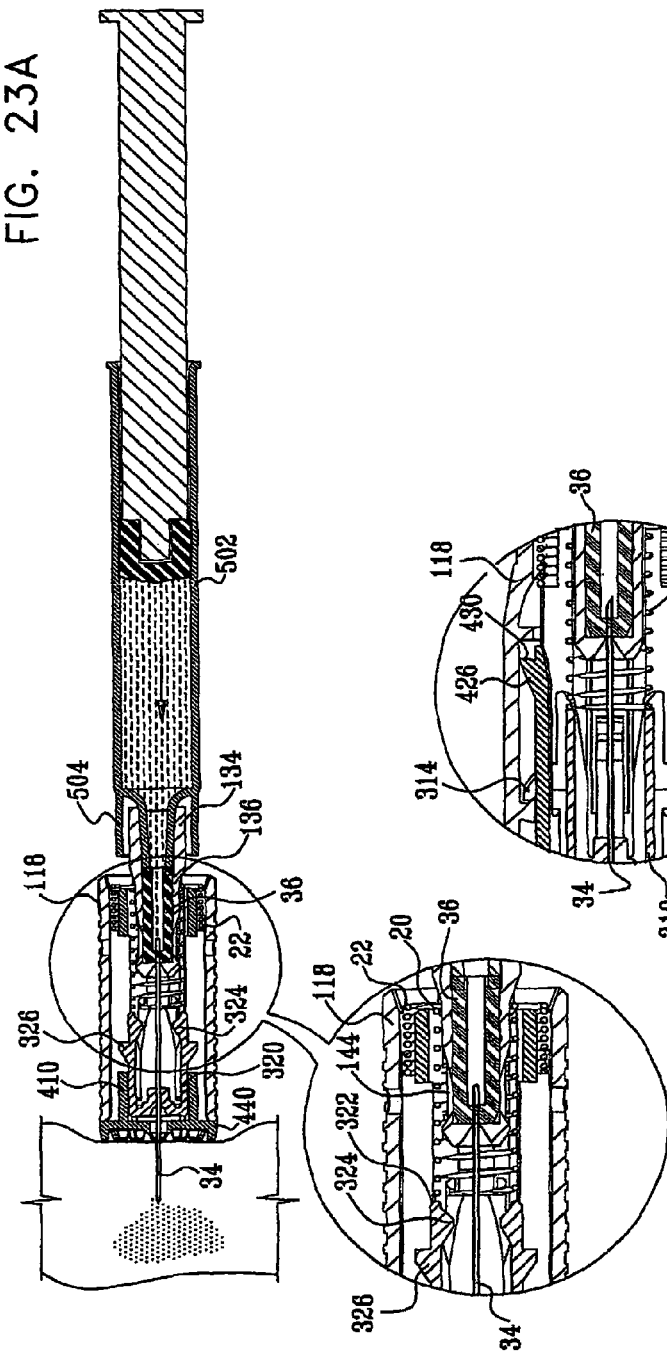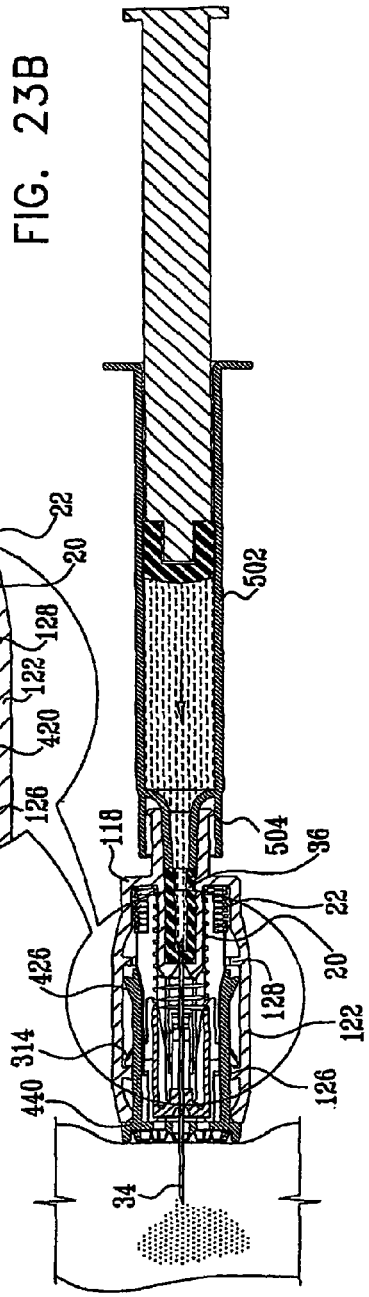

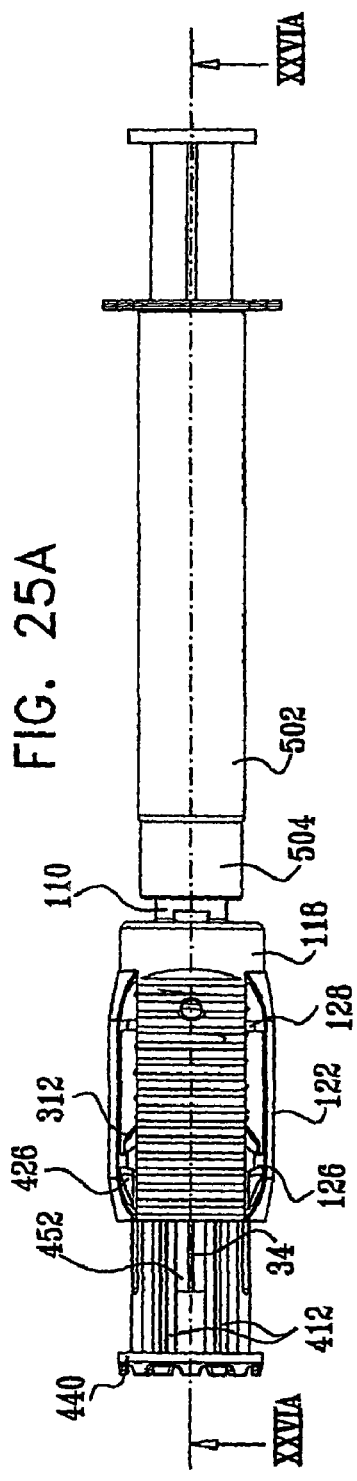
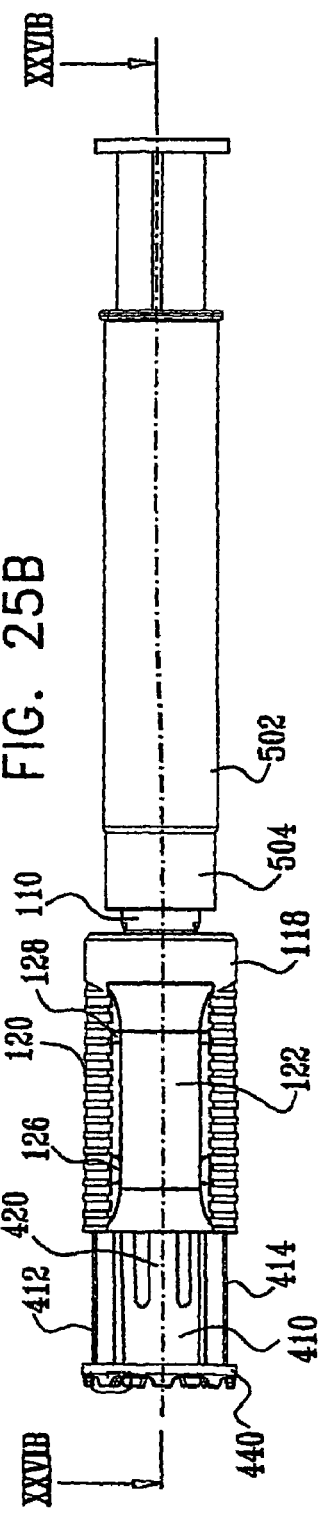
FIG. 25A
FIG. 25B

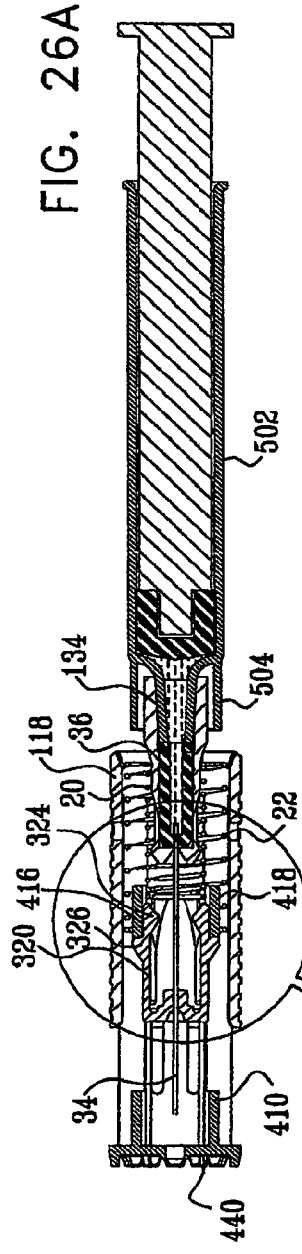
FIG. 26A
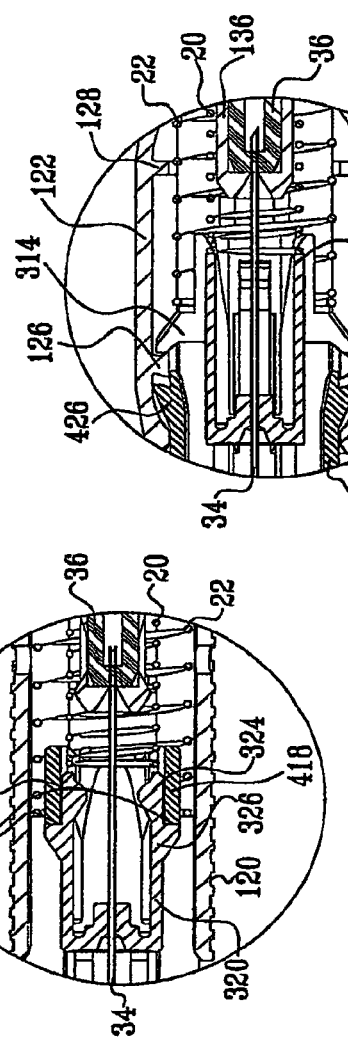
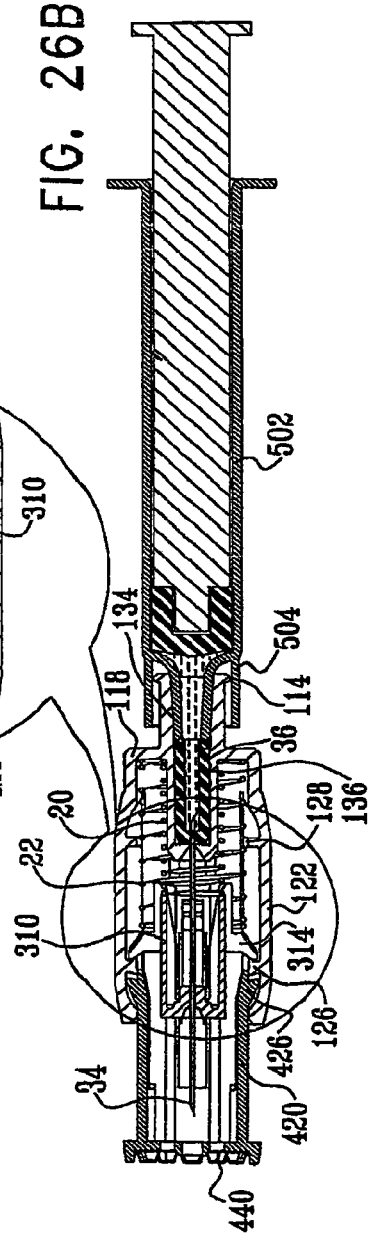
FIG. 26B

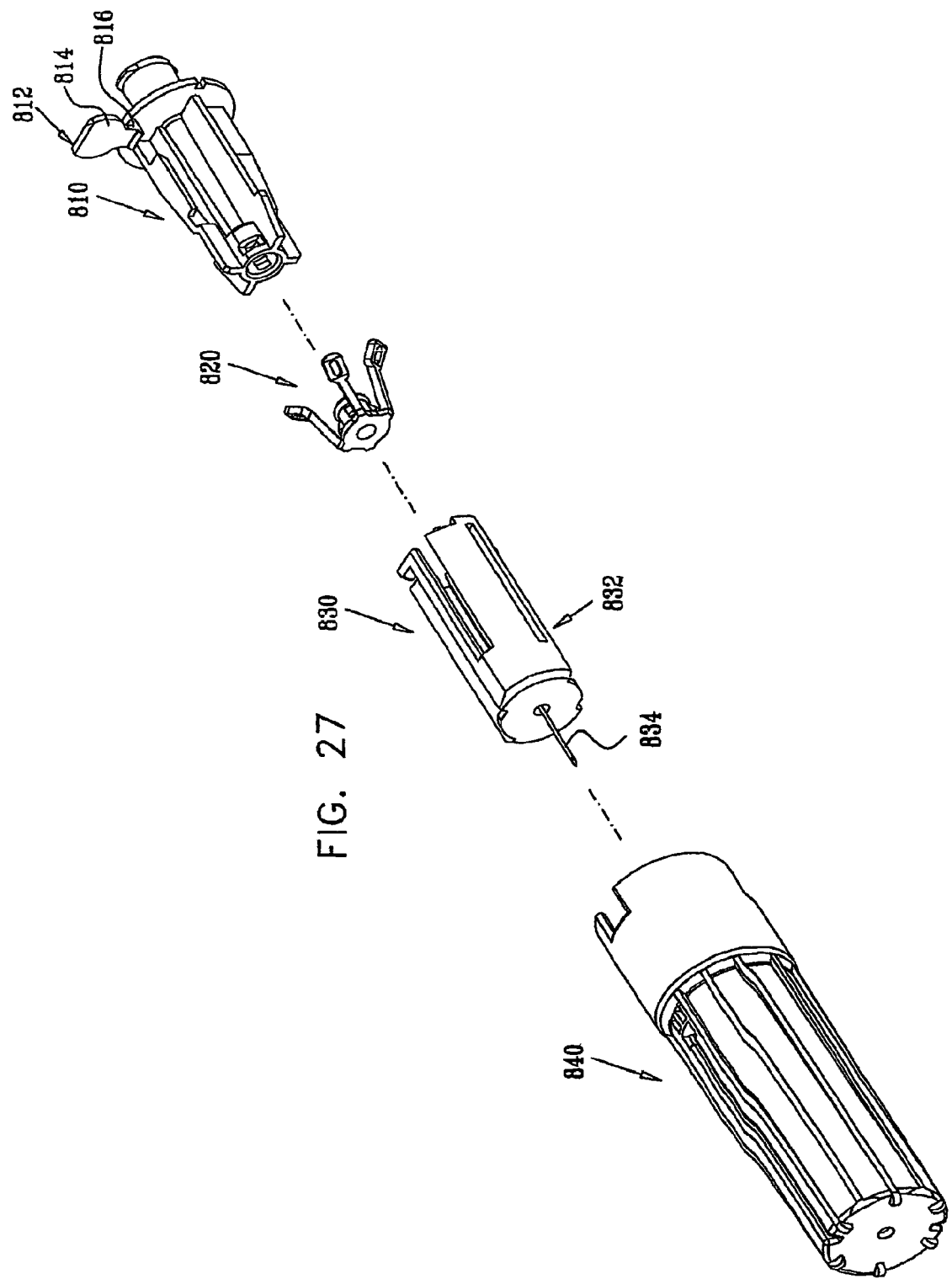

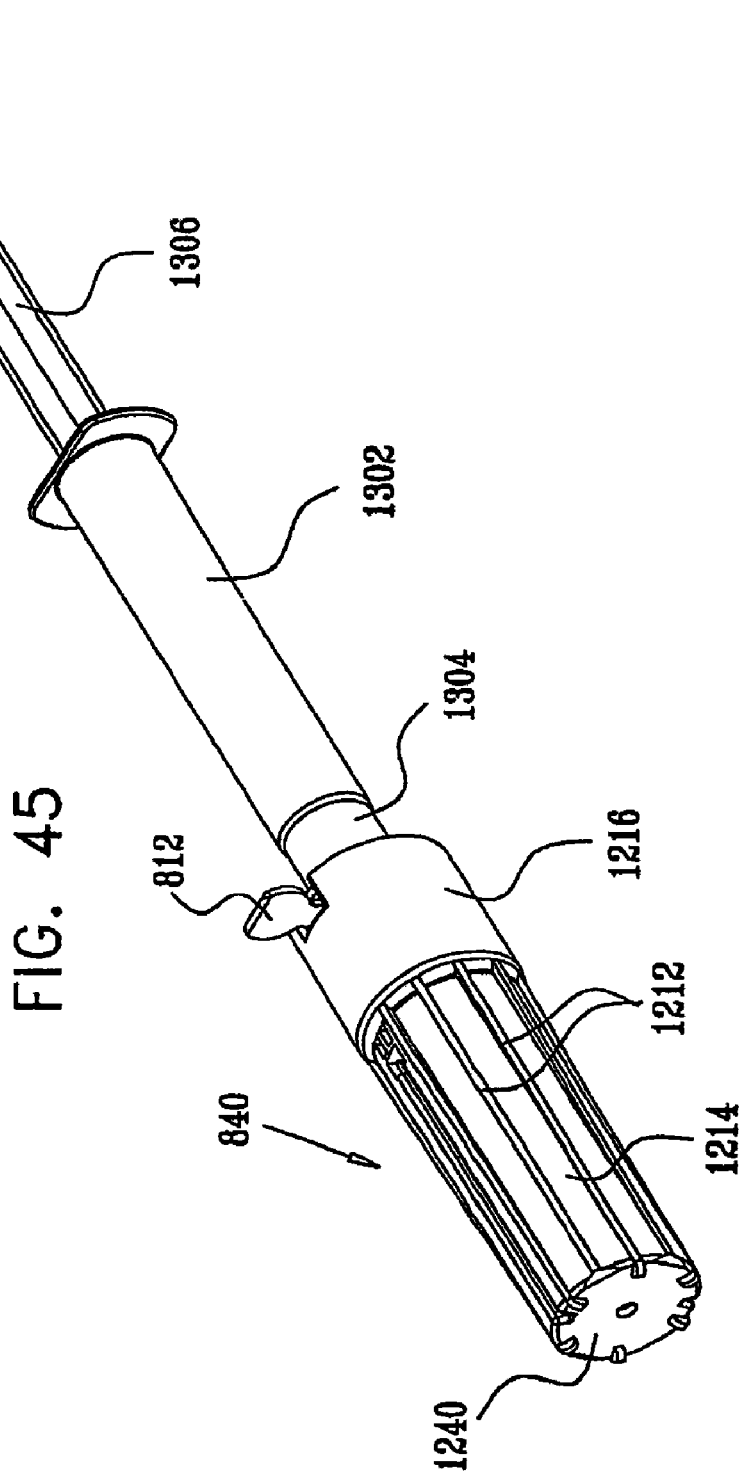

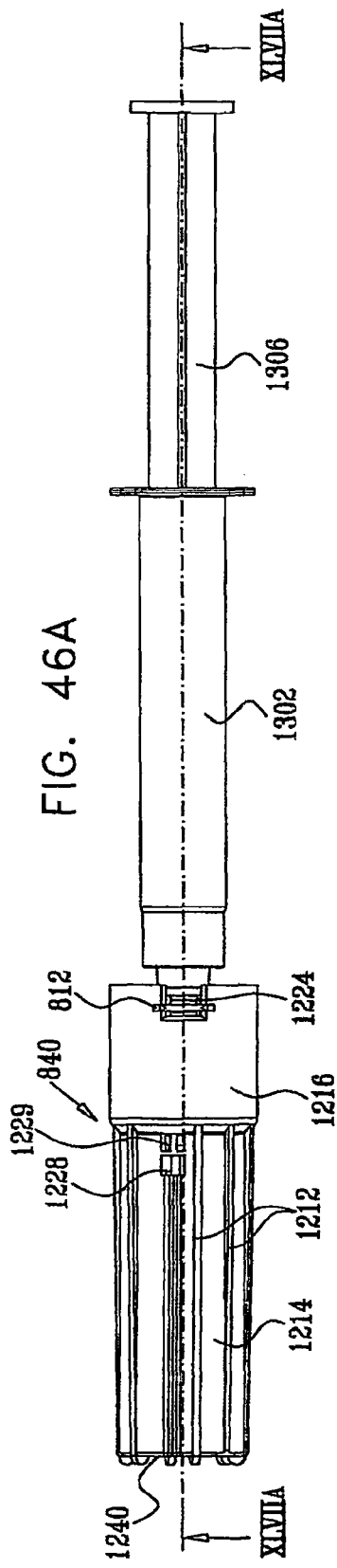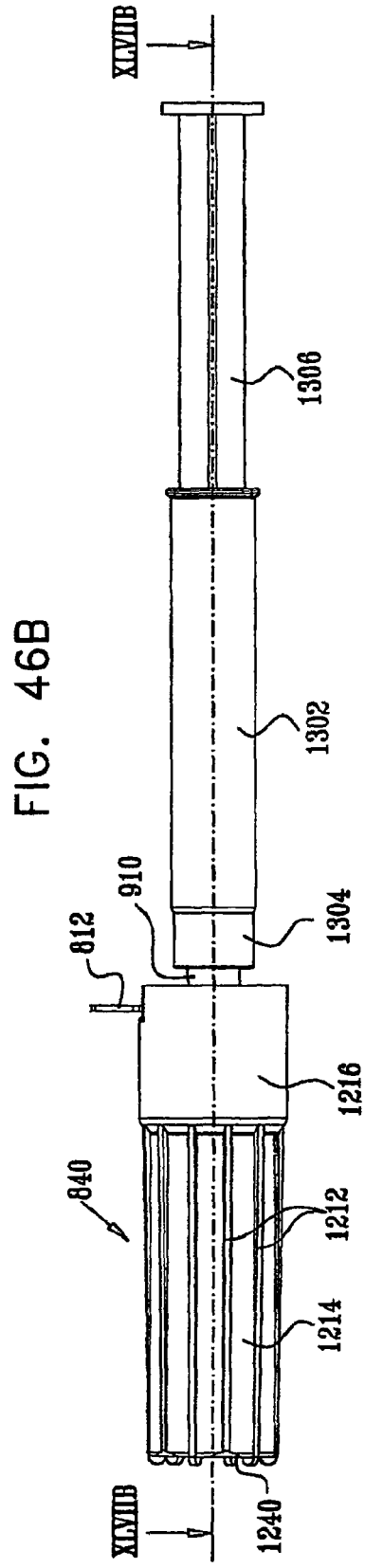

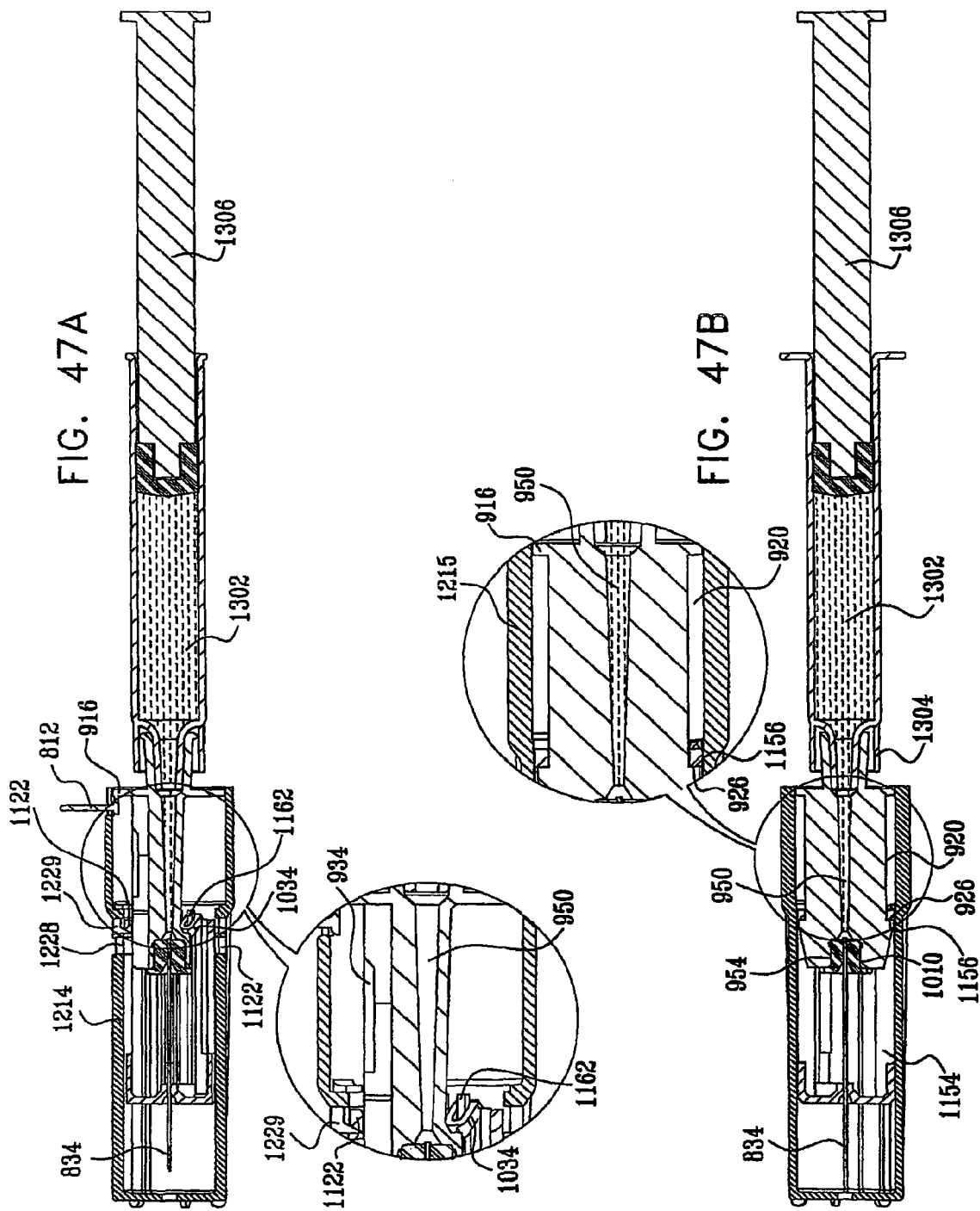

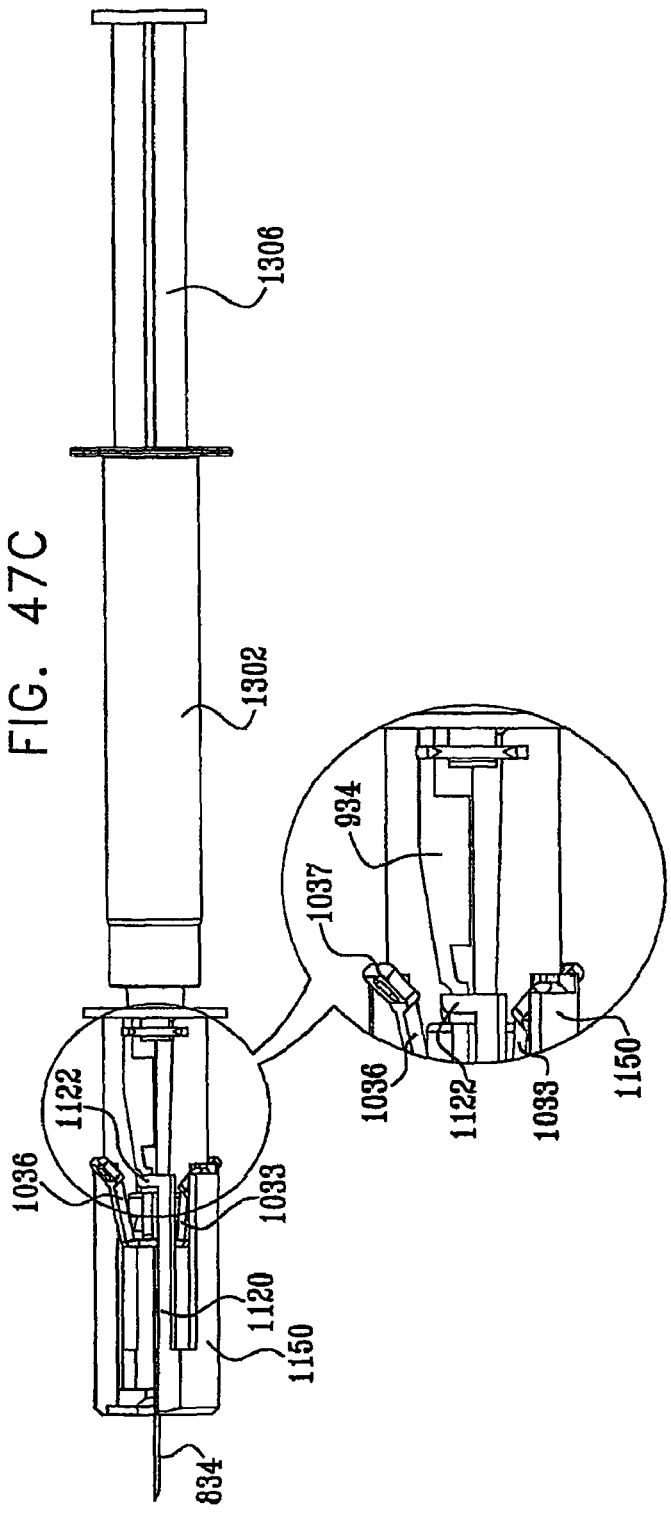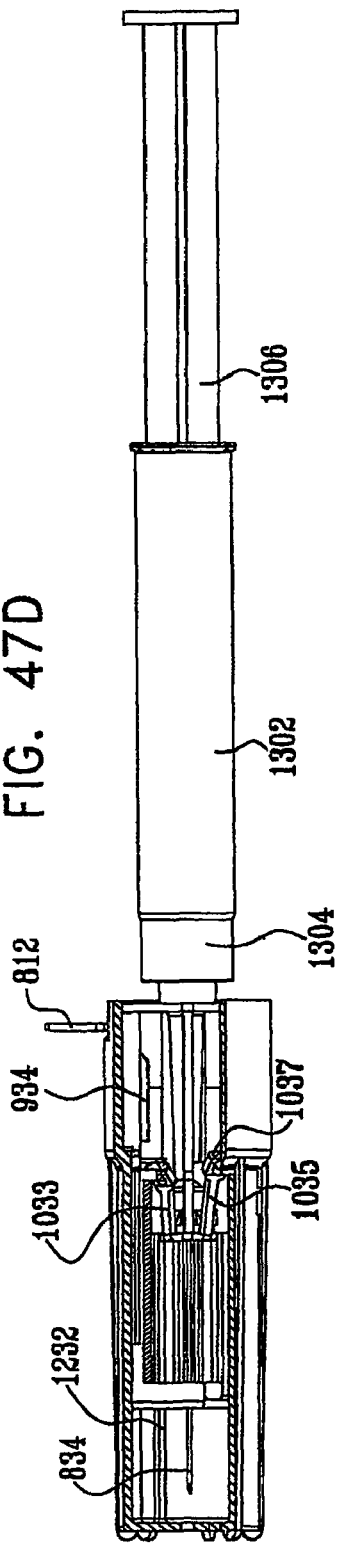

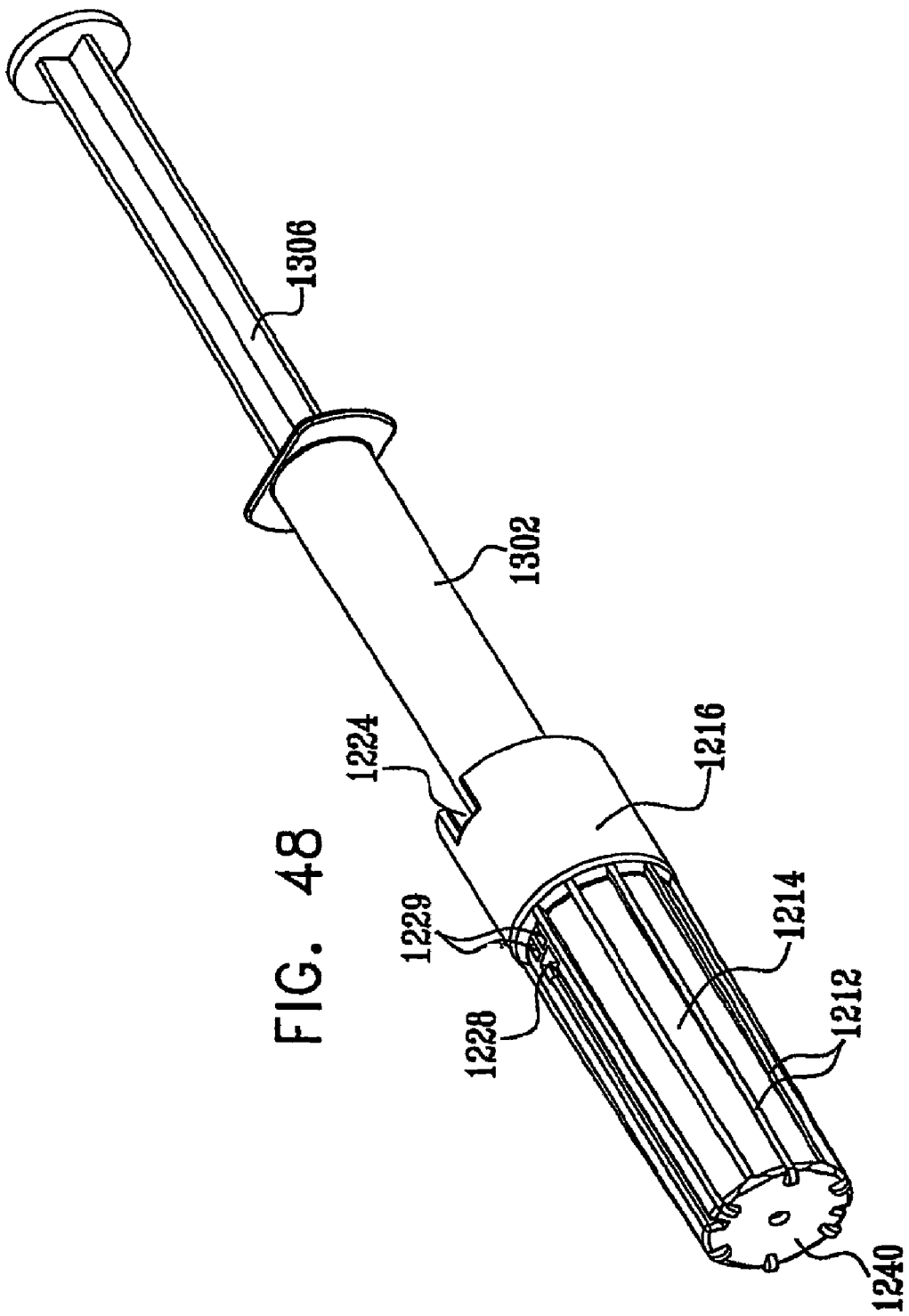

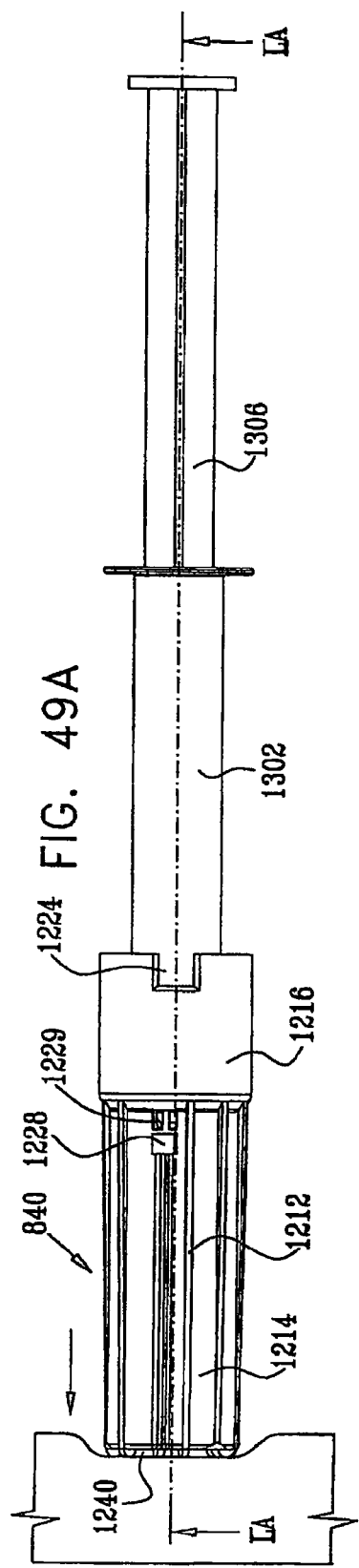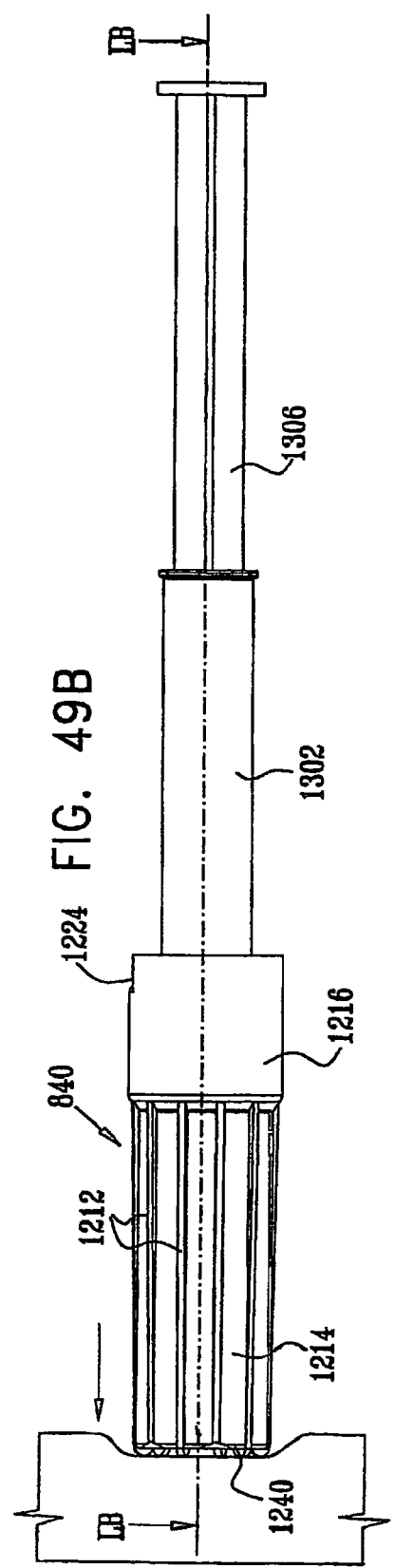

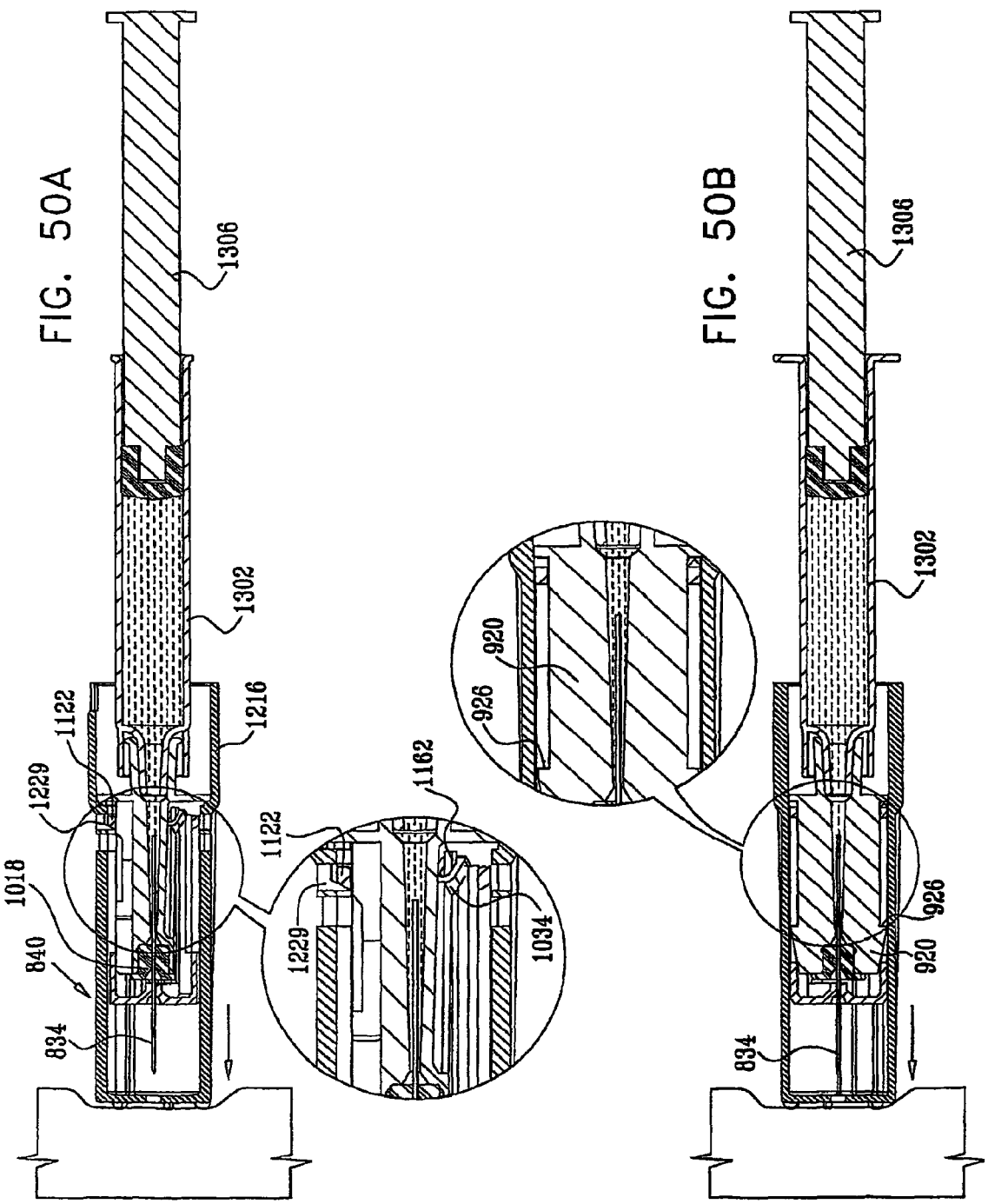

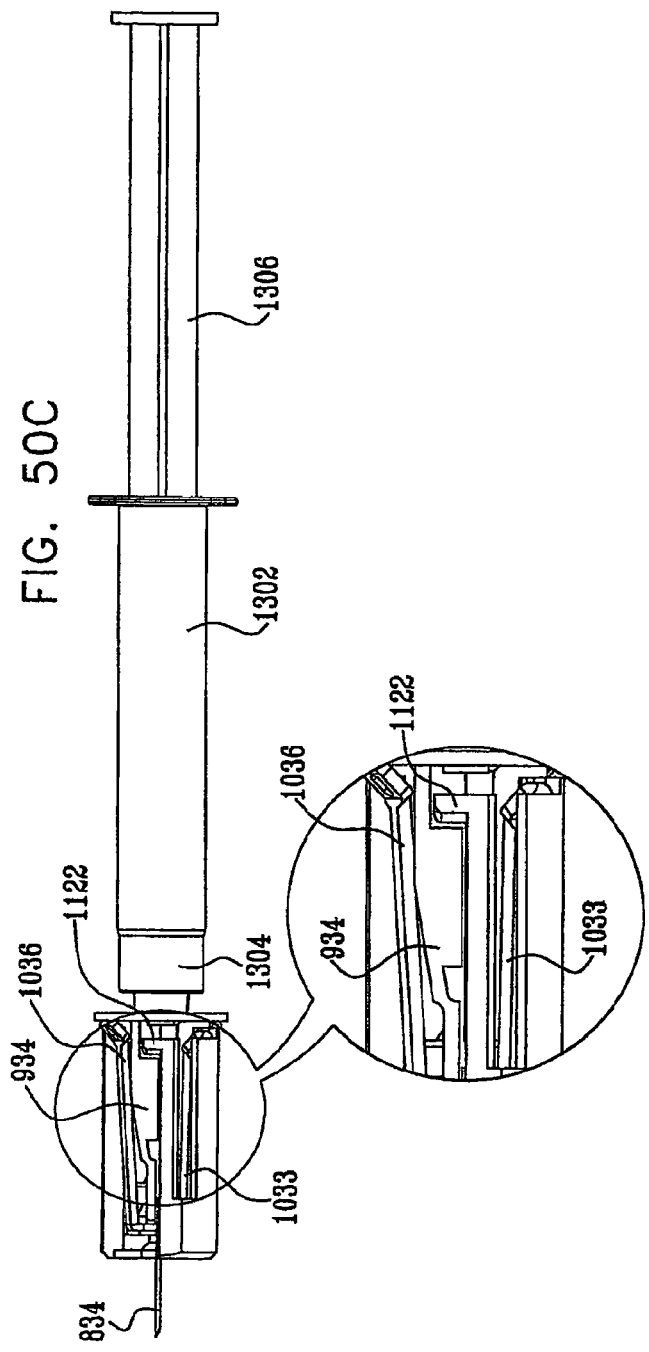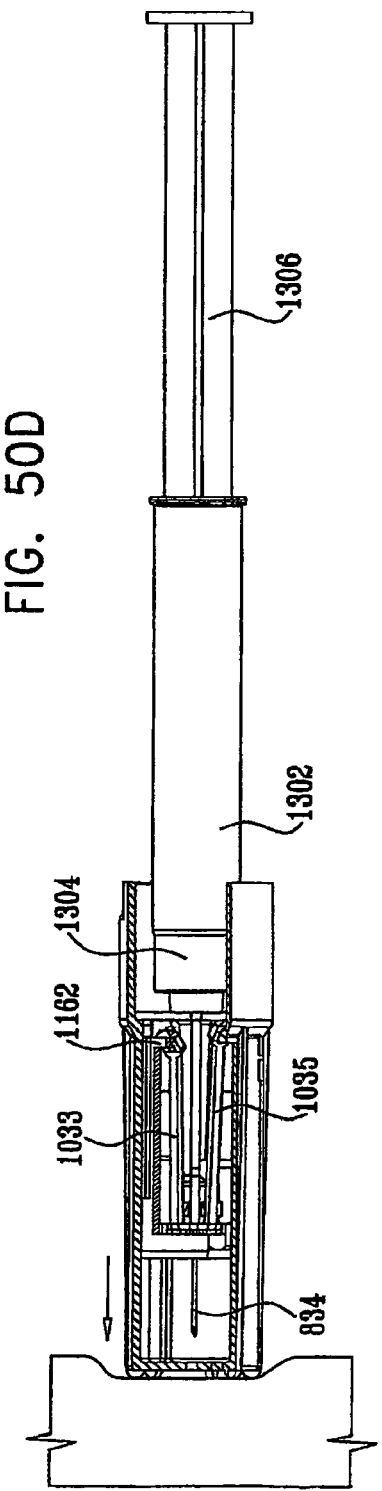

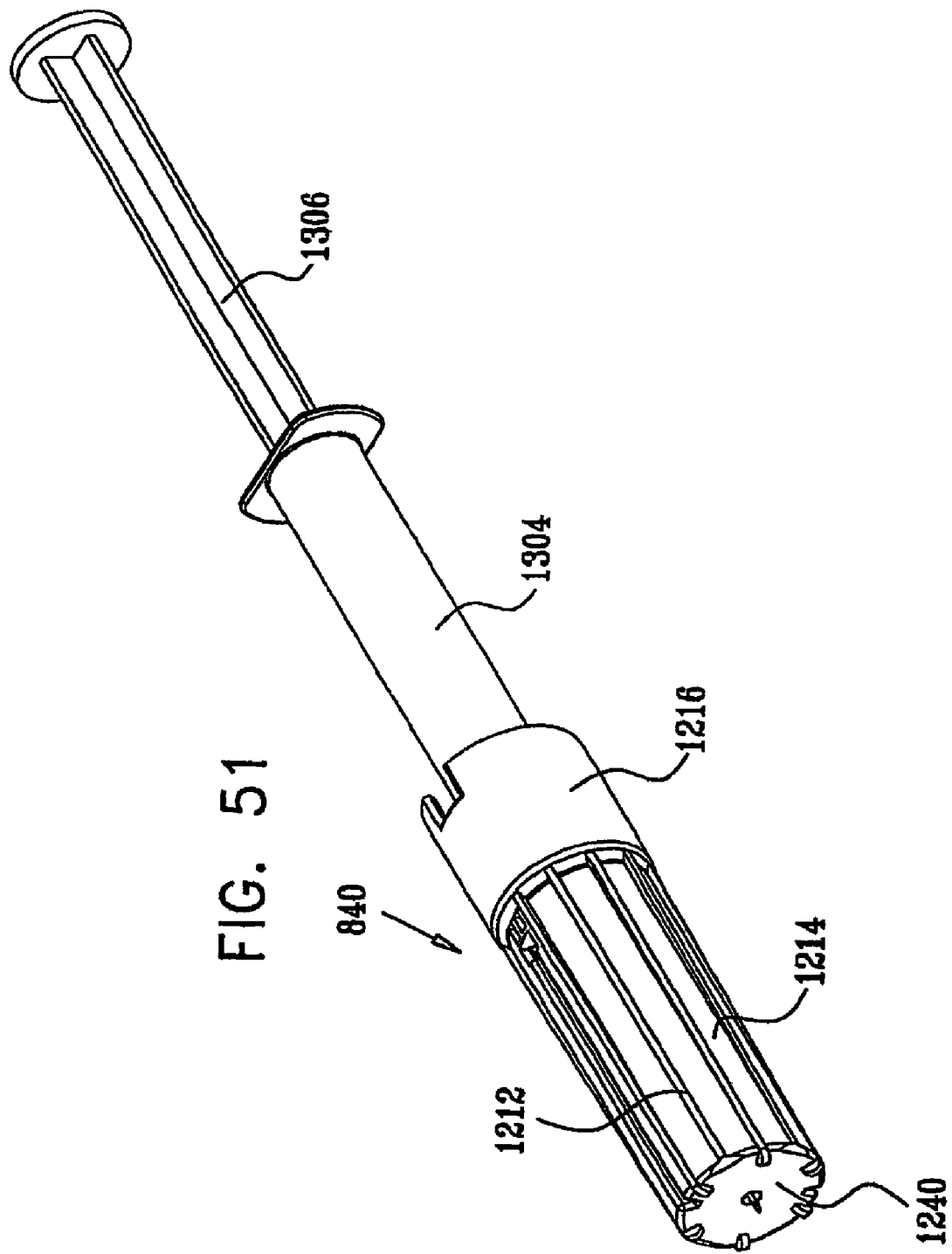

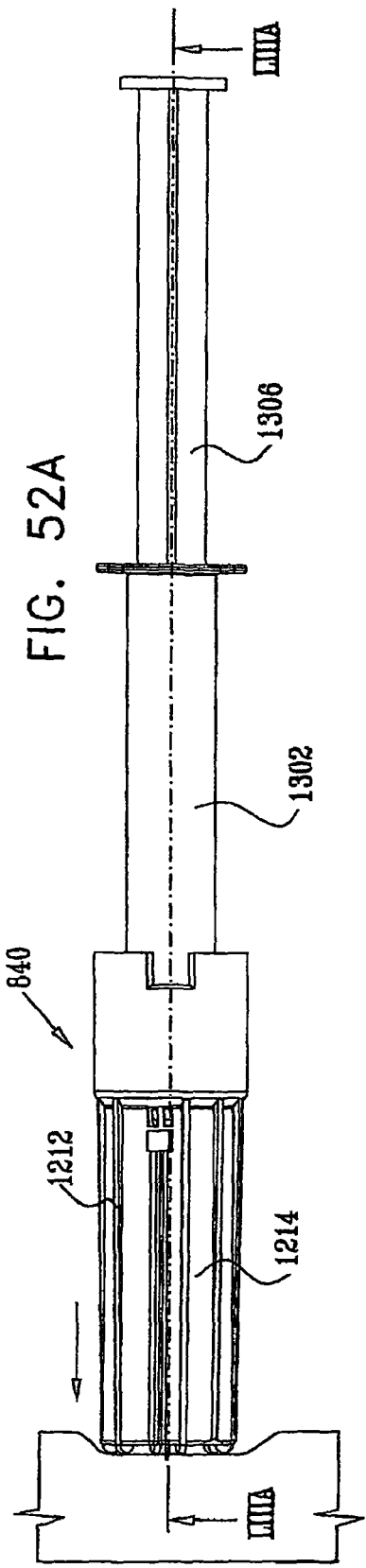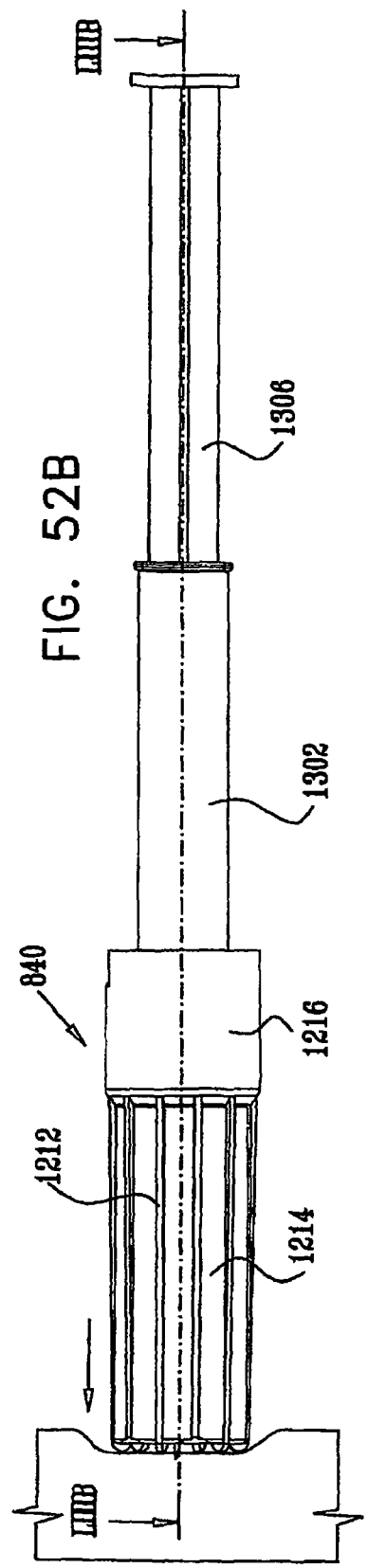

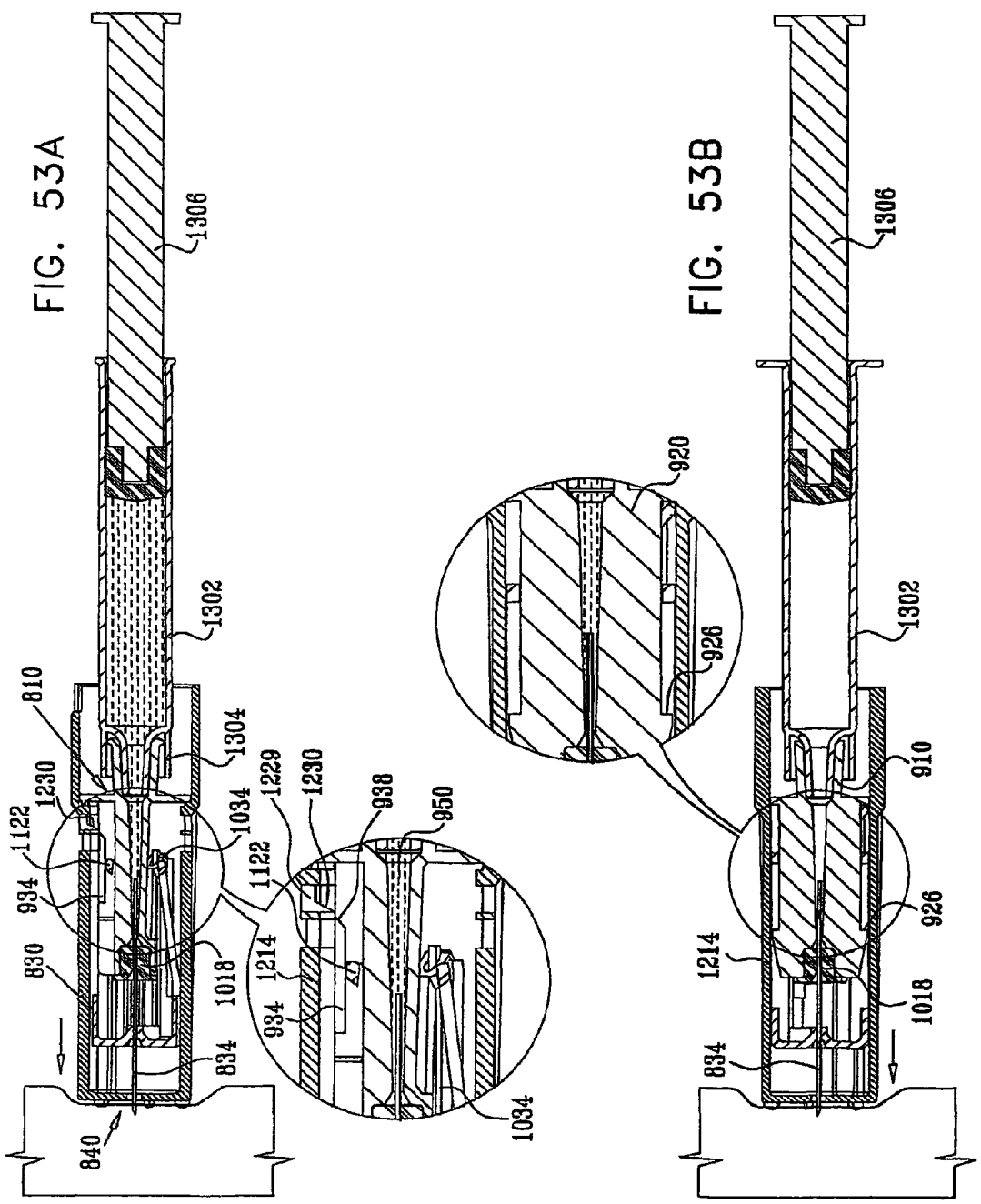

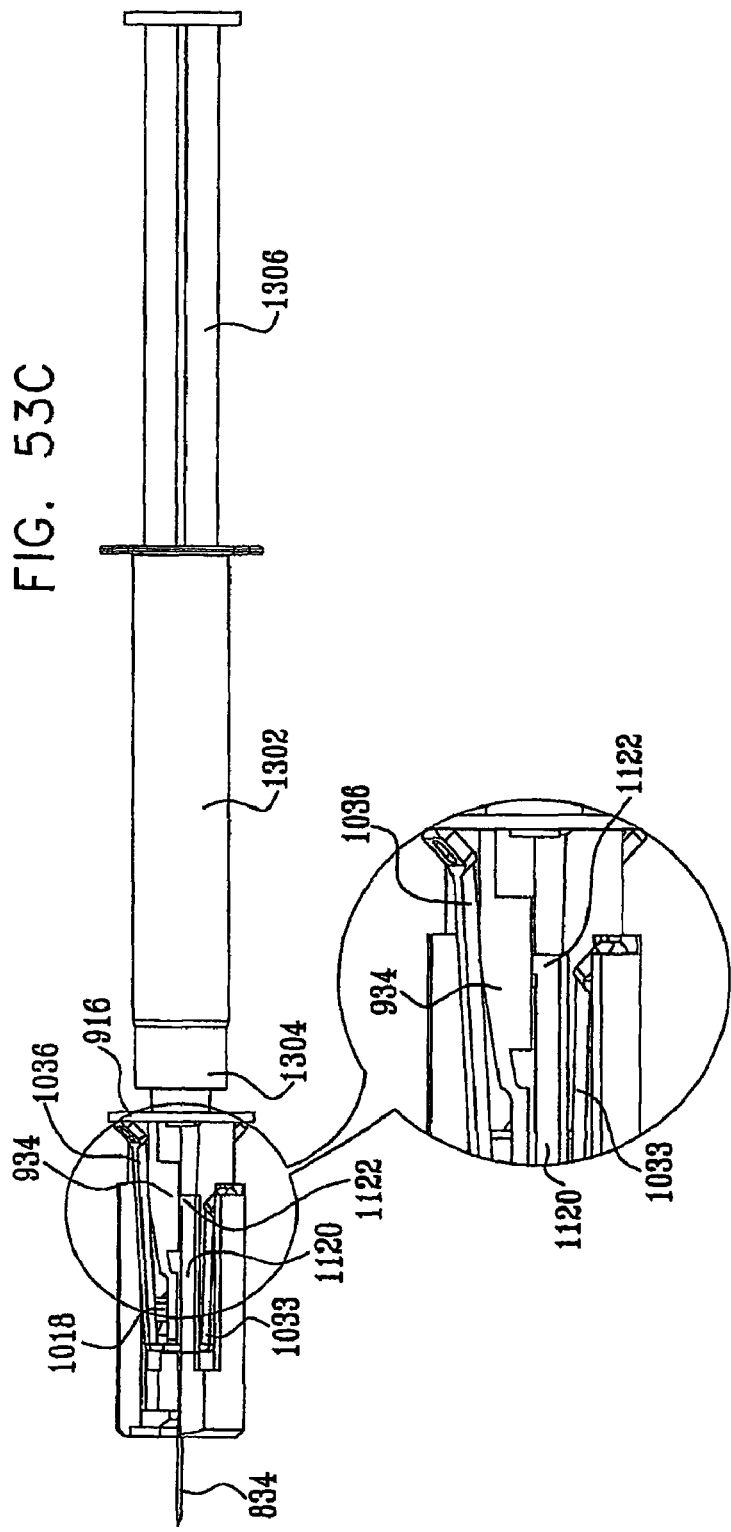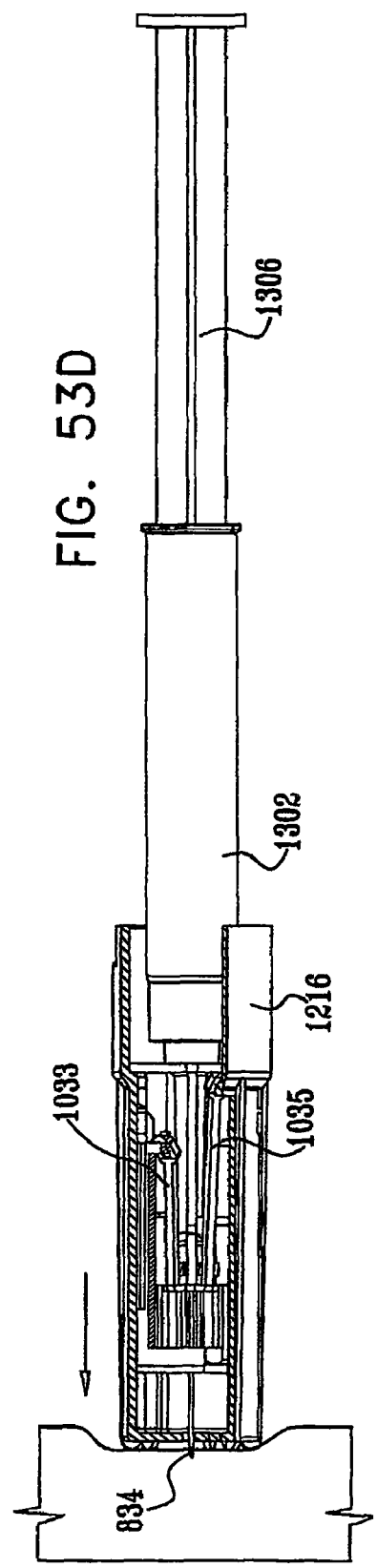

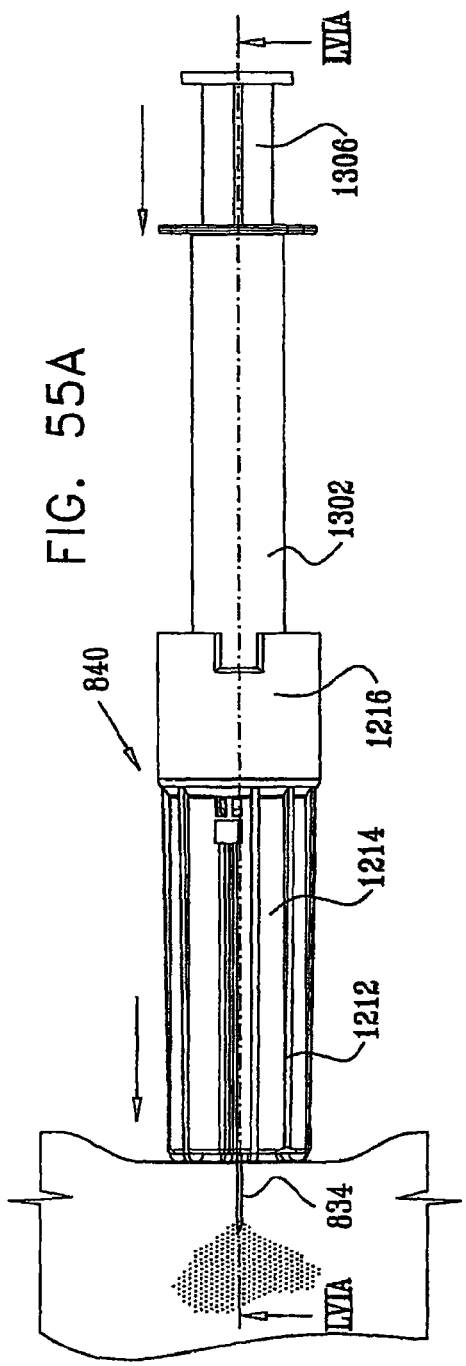
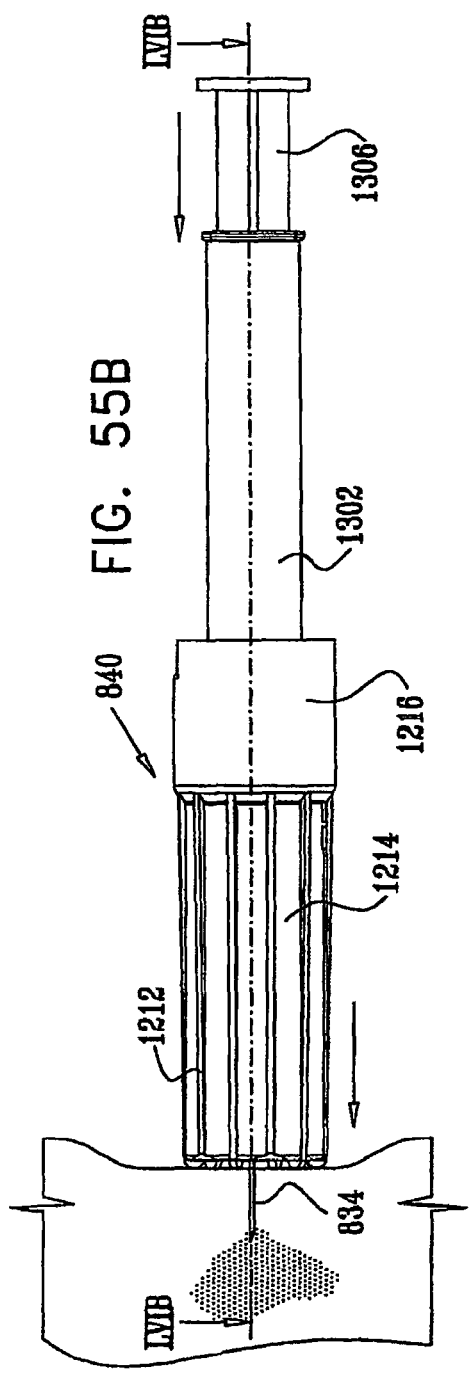
FIG. 55A
FIG. 55B

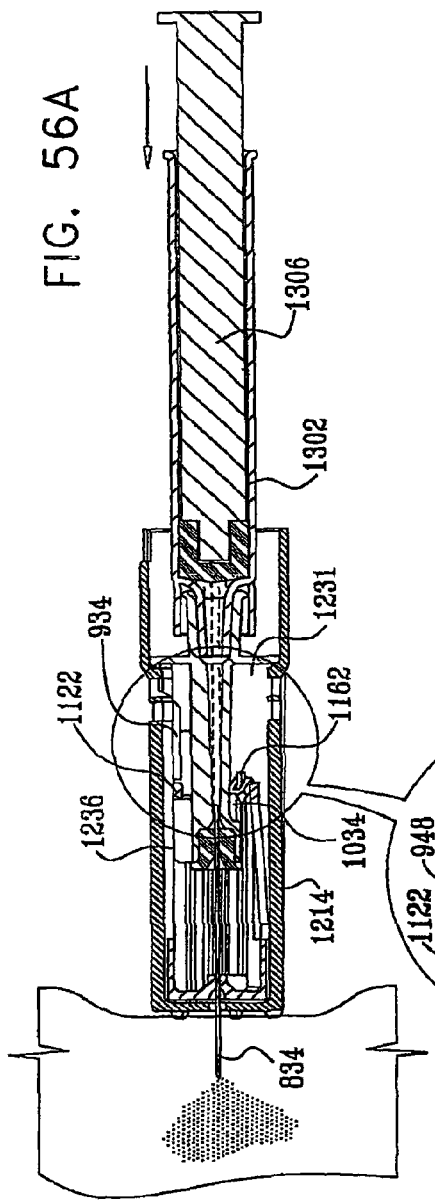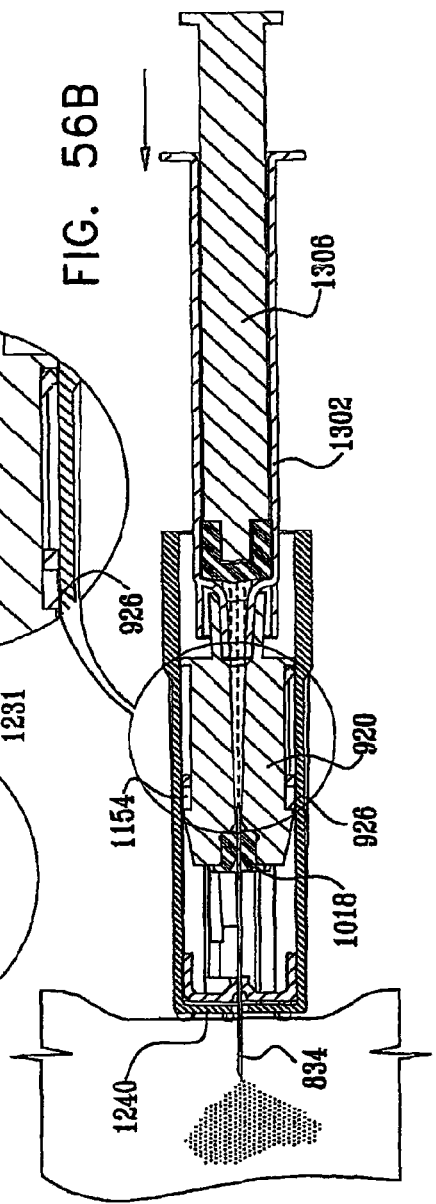

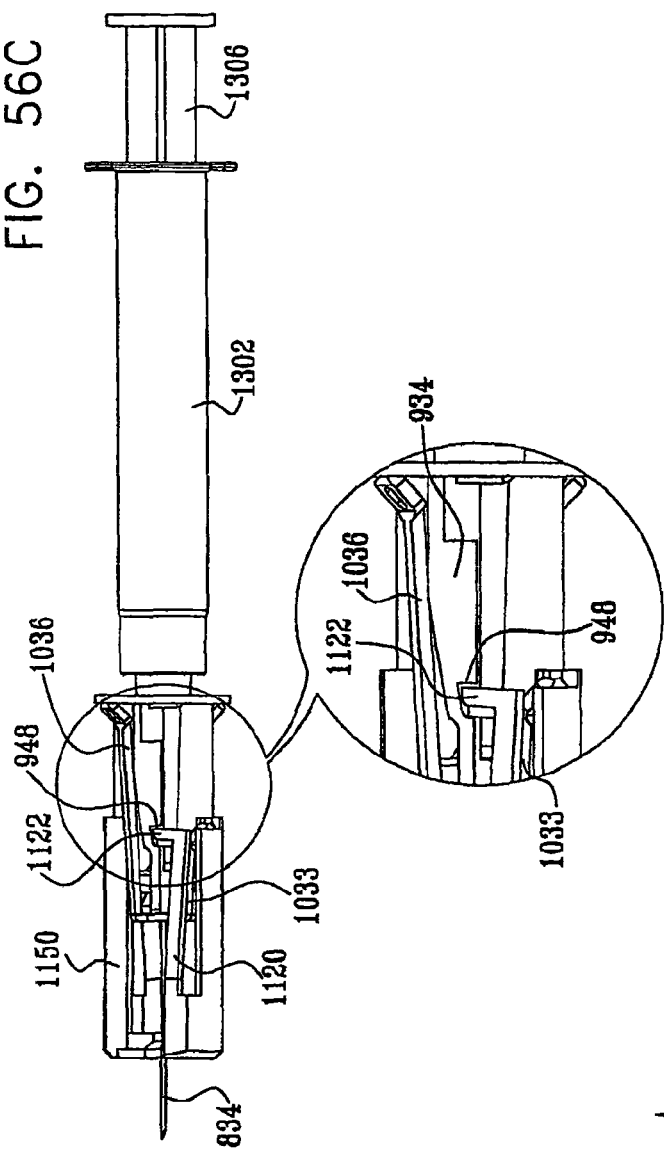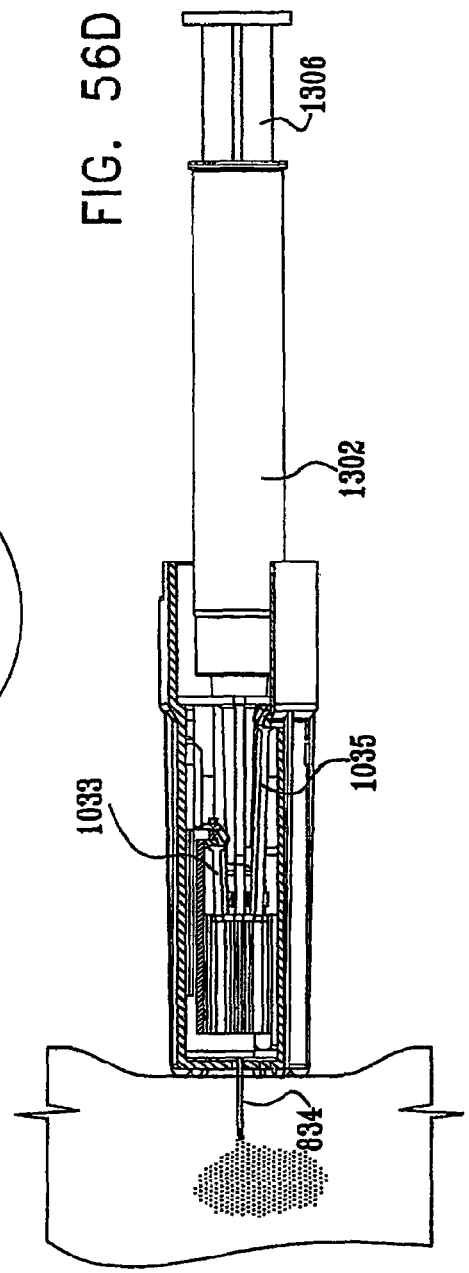

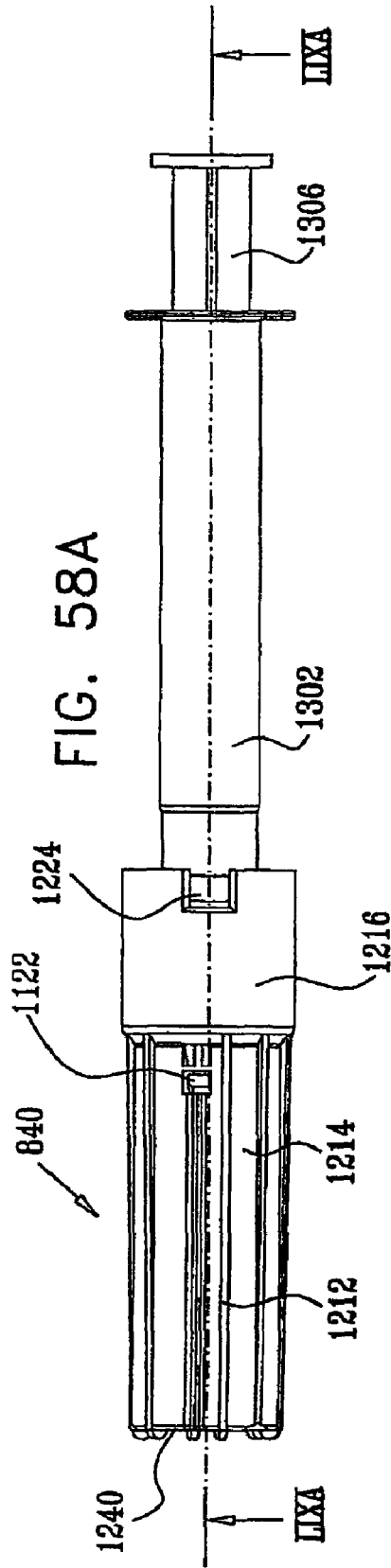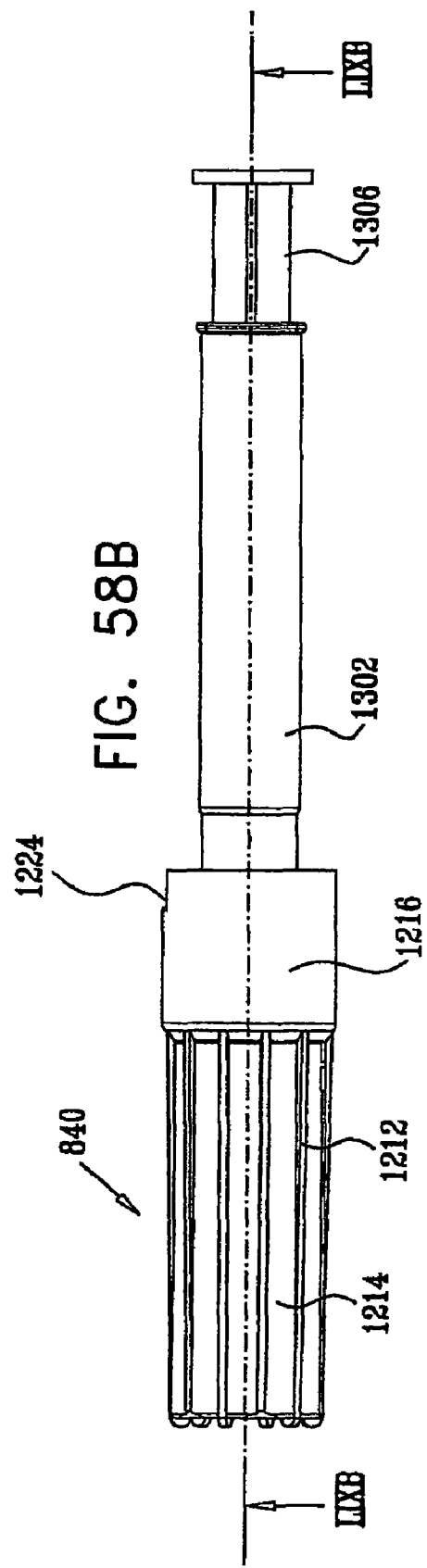

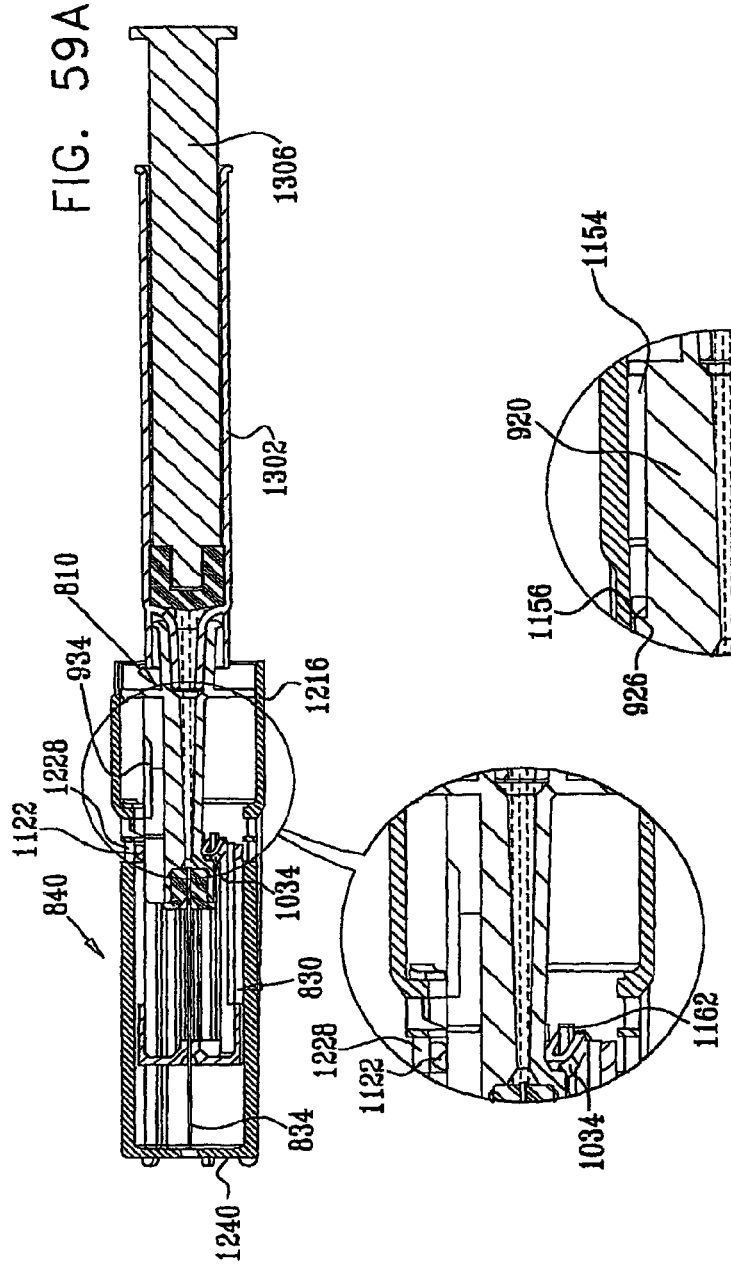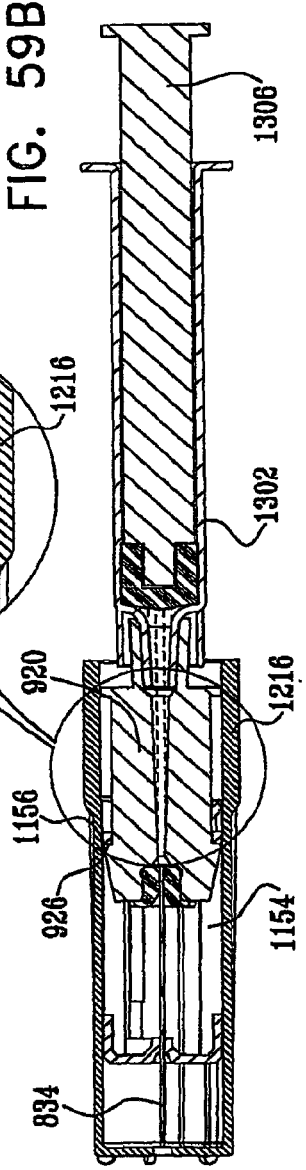

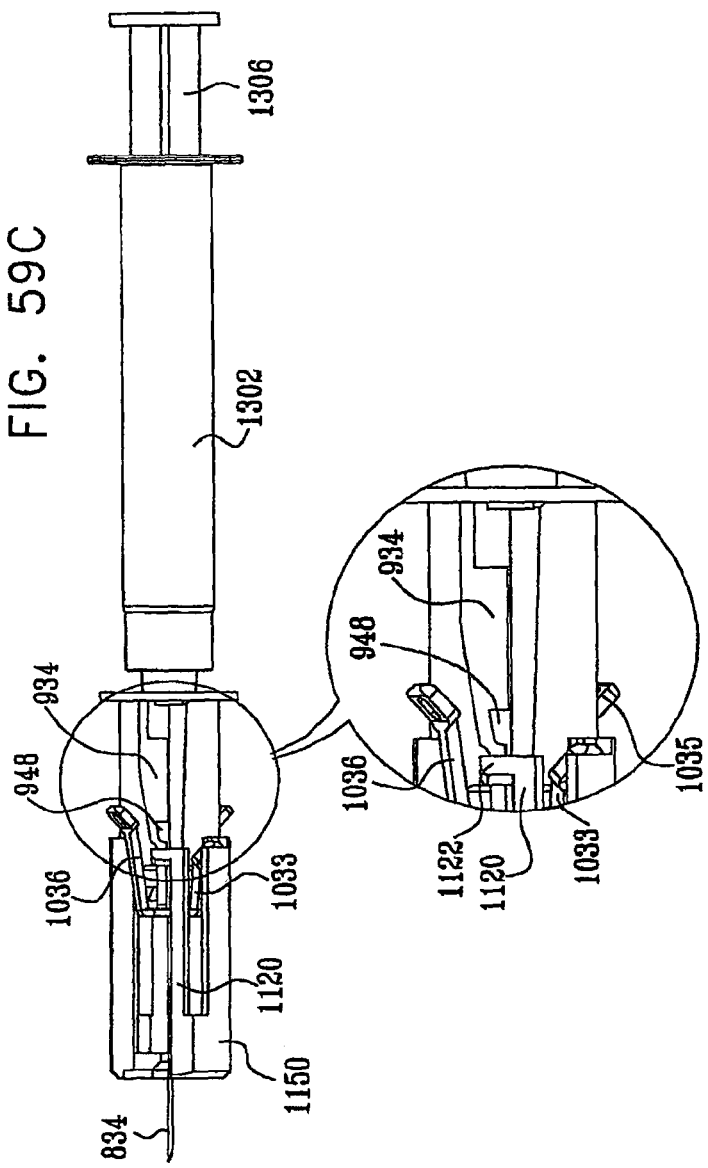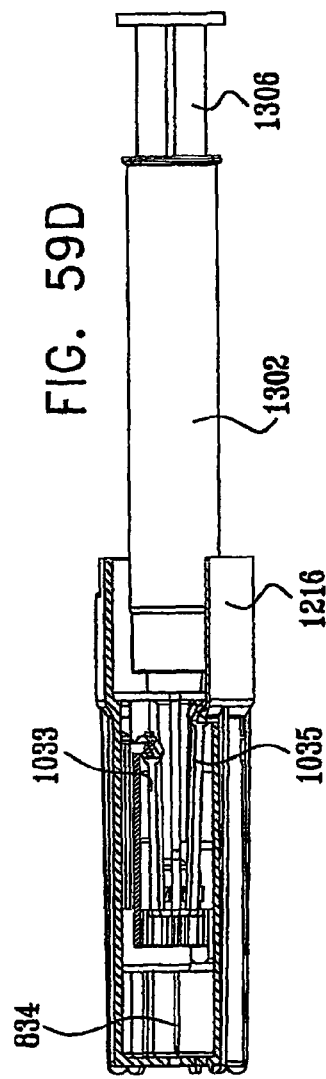

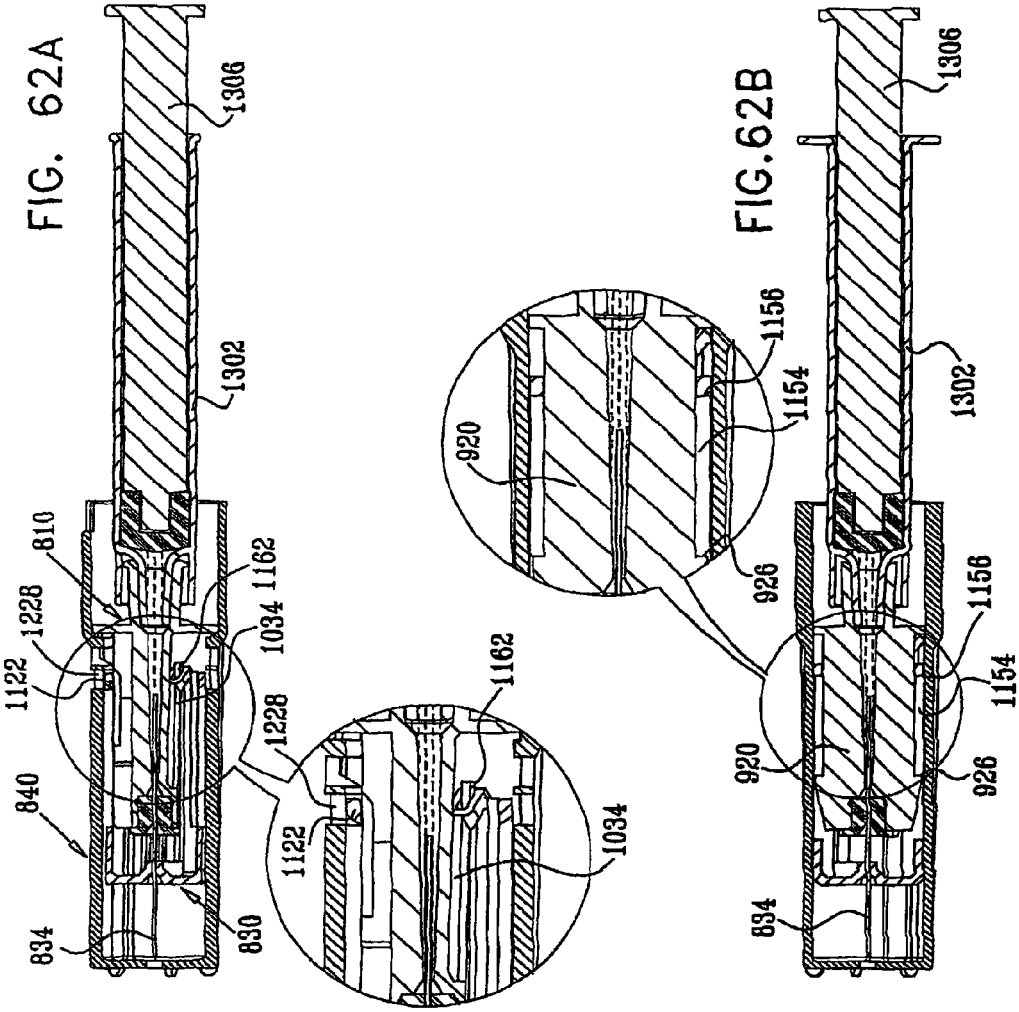

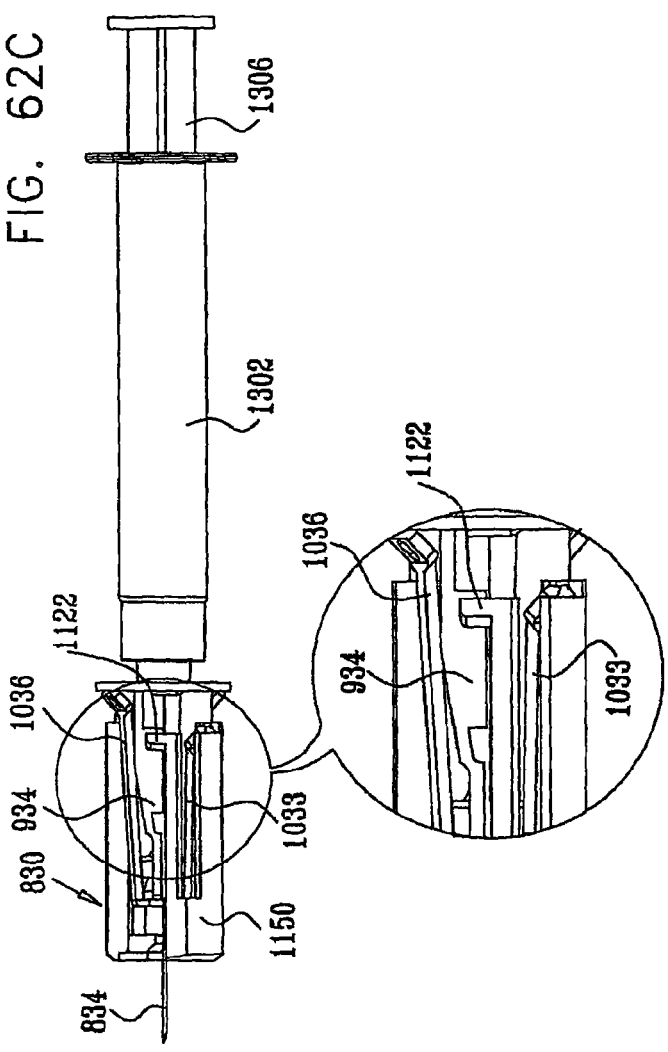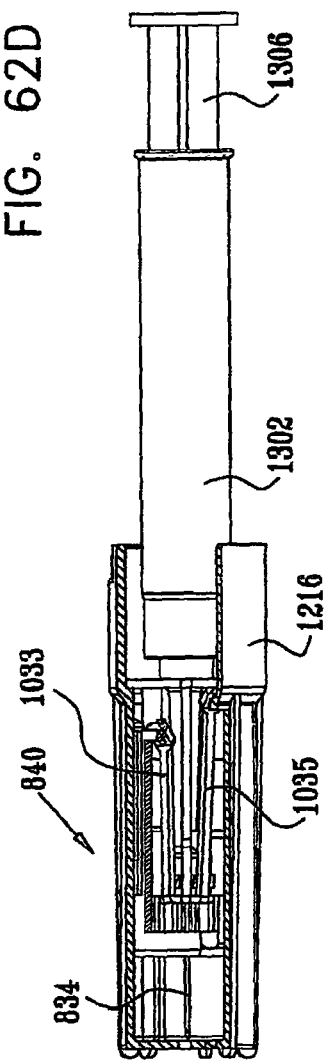

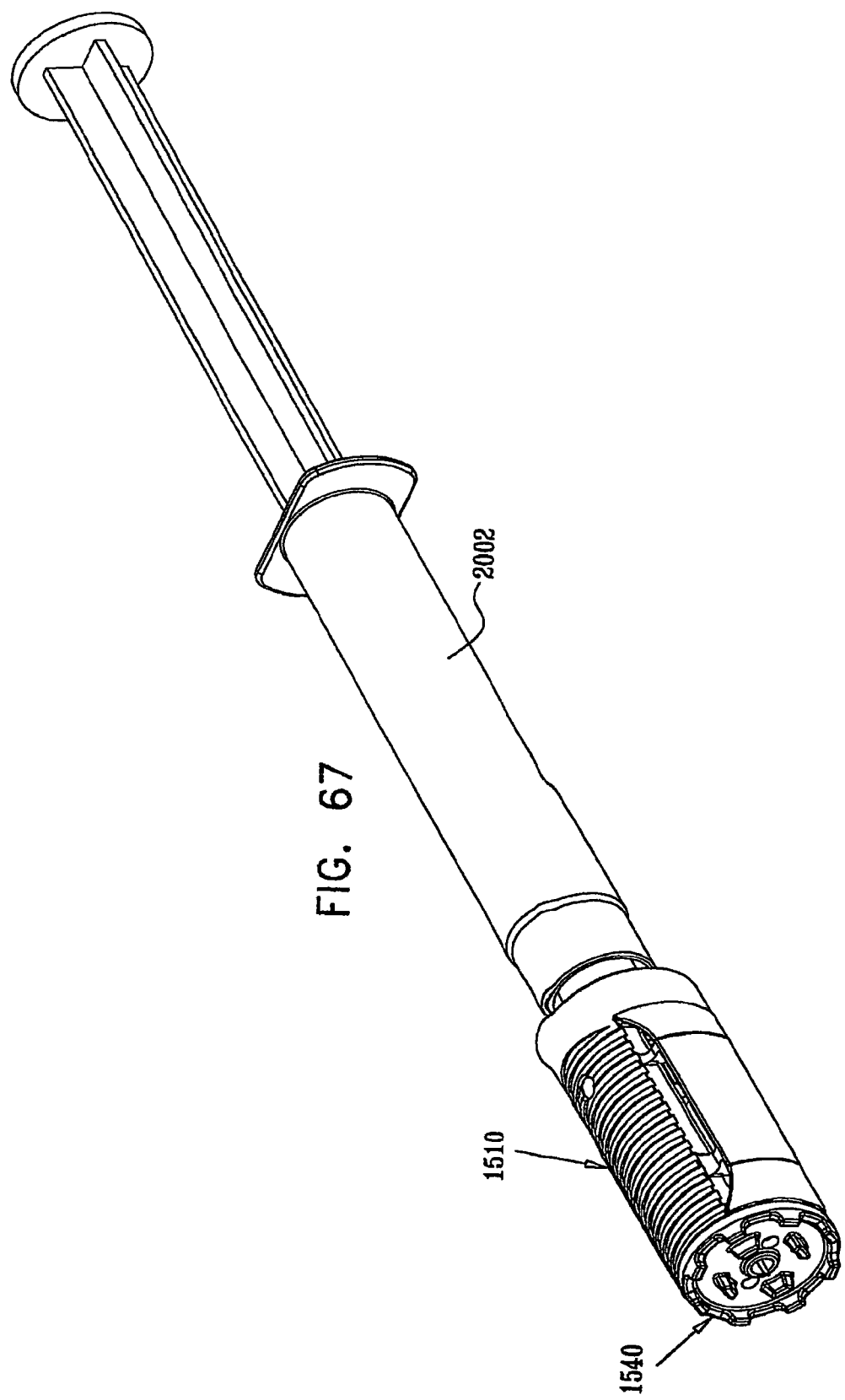

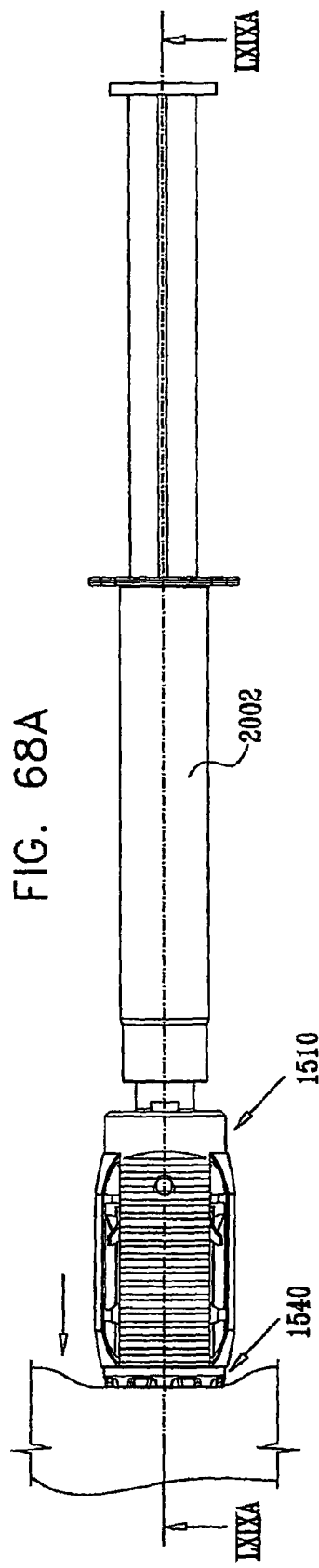
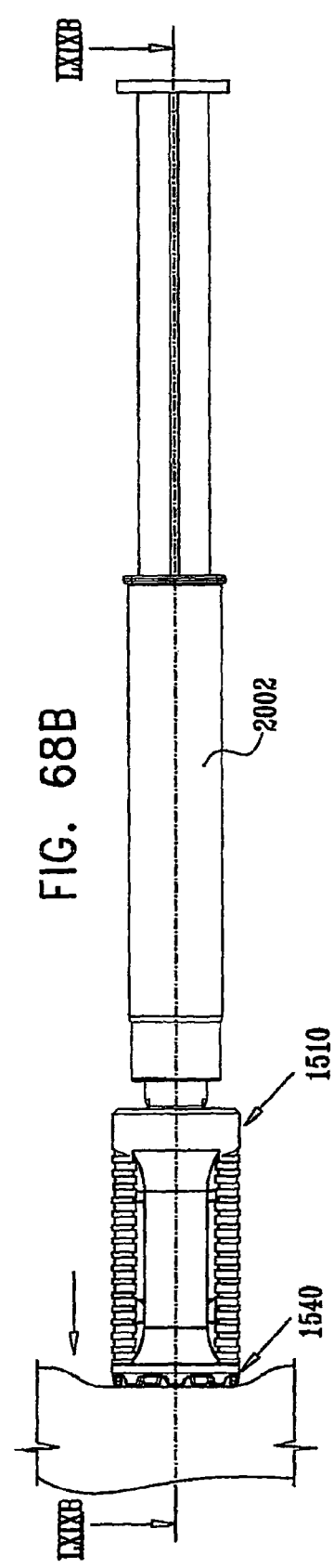

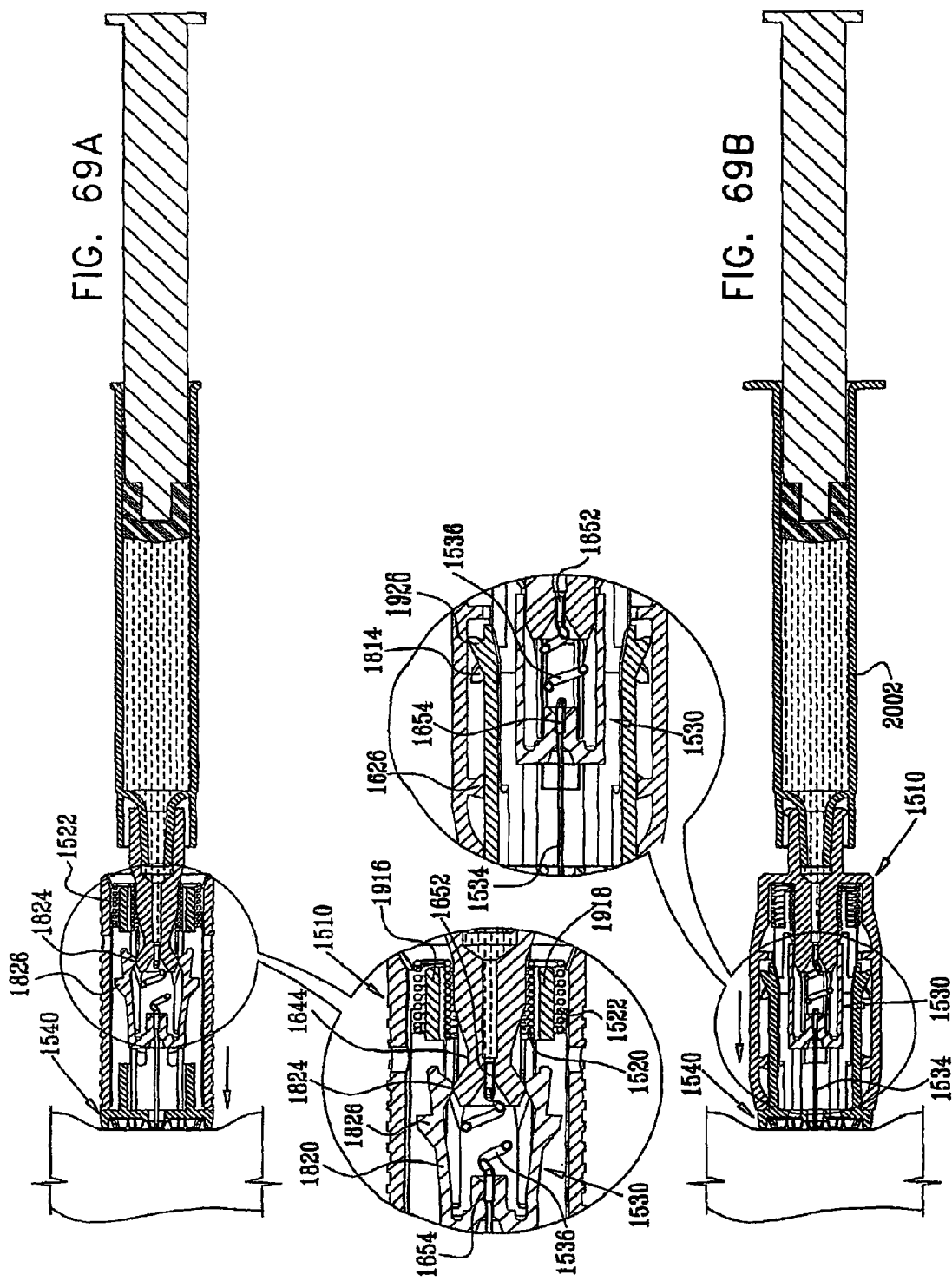

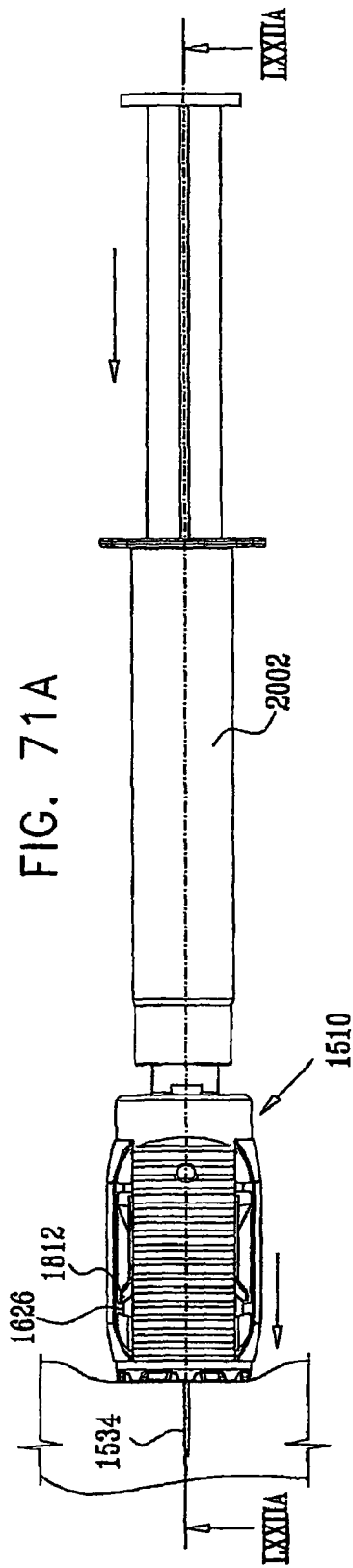
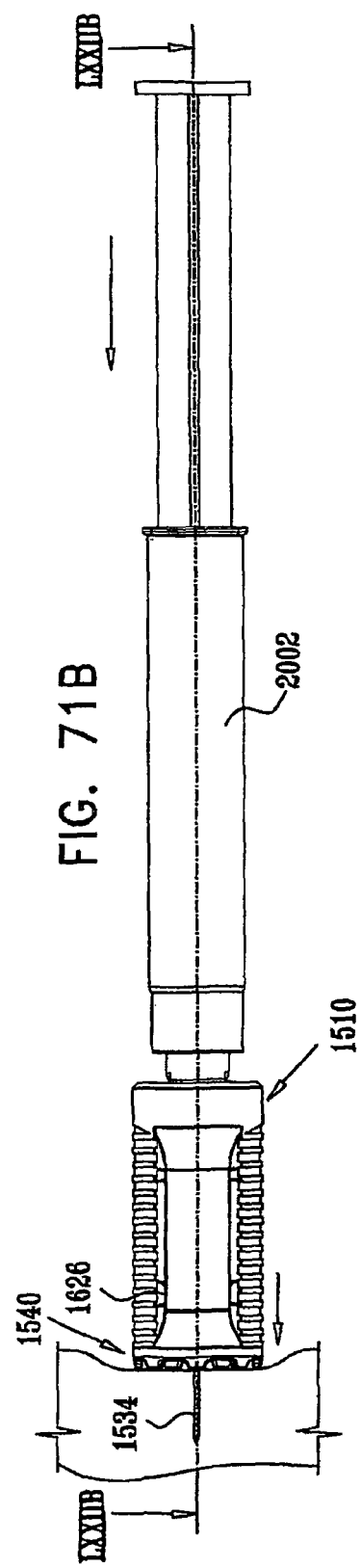

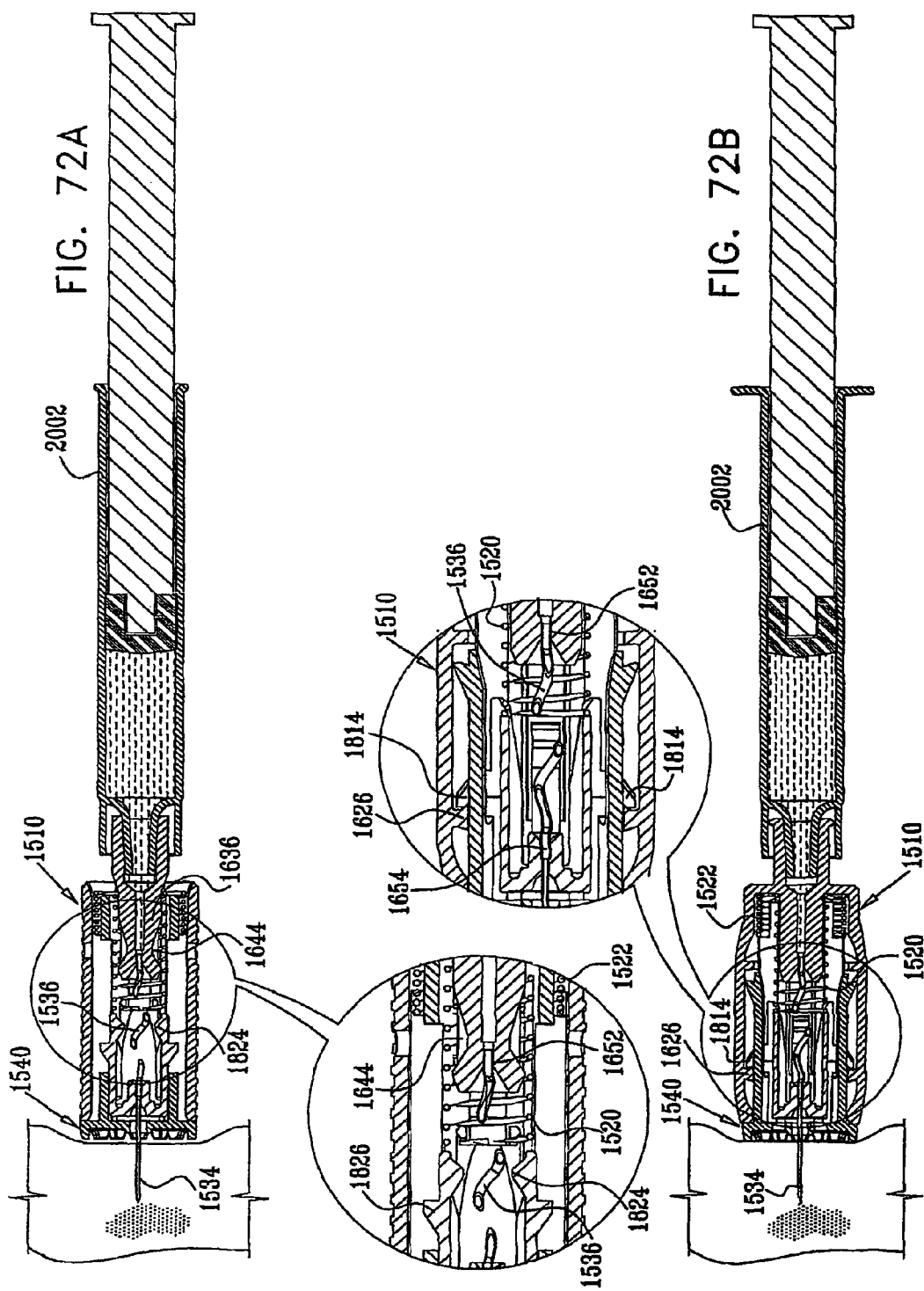

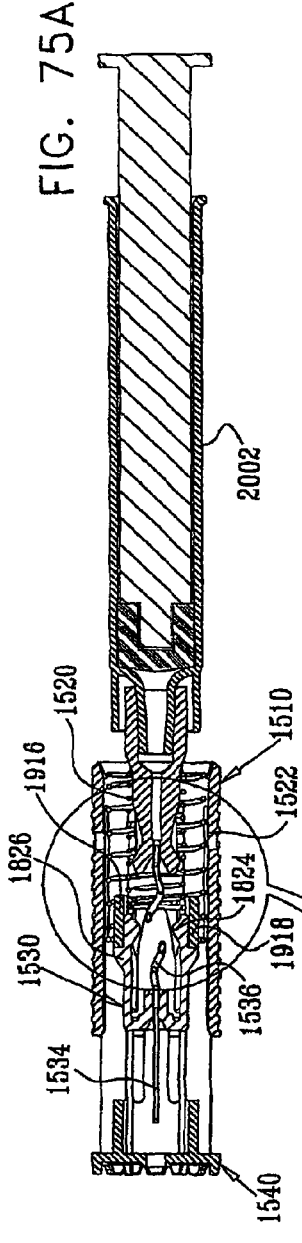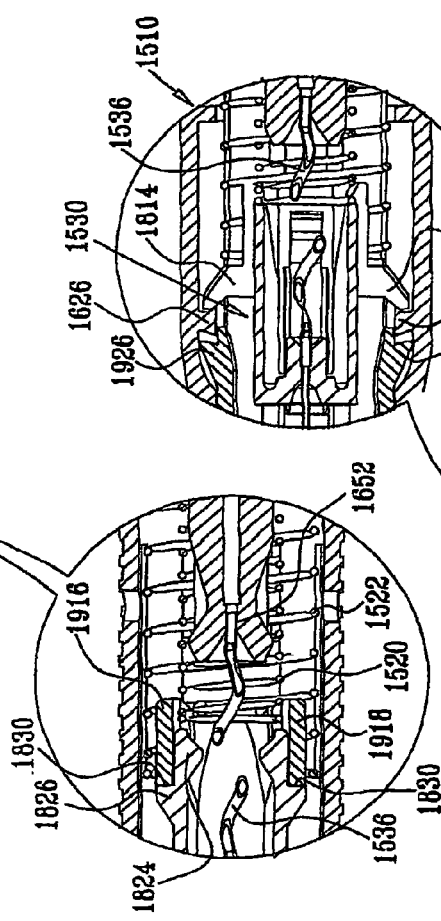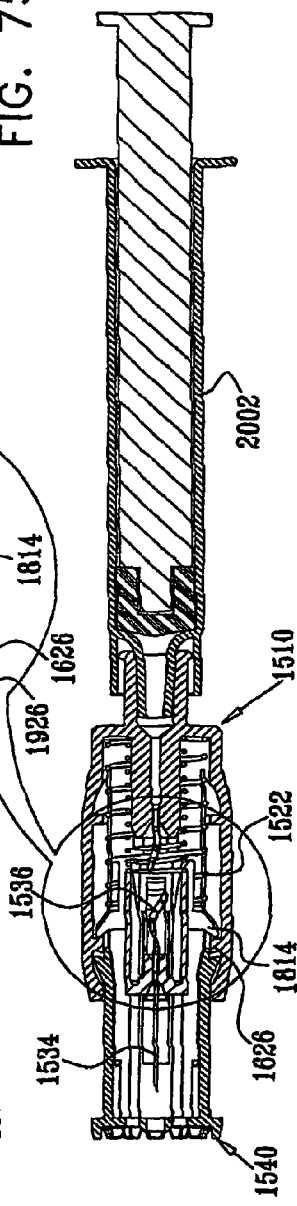

AUTOMATIC NEEDLE DEVICE

REFERENCE TO CO-PENDING APPLICATIONS

This application is a continuation of U.S. patent application Ser. No. 10/572,215, filed Sep. 8, 2006, which is the U.S. National Phase of PCT/IL2004/000852, filed Sep. 15, 2004 and claims the priority of Israel Patent Application No. 157984, filed Sep. 17, 2003, all of which are incorporated by reference.

FIELD OF THE INVENTION

The present invention relates to automatic needle devices for hypodermic syringes generally.

BACKGROUND OF THE INVENTION

The following U.S. patents are believed to represent the current state of the art: U.S. Pat. Nos. 4,474,572; 4,475,906; 4,484,910; 4,487,602; 4,505,710; 4,512,767; 4,515,590; 4,518,387; 4,529,401; 4,529,403; 4,530,695; 4,534,759; 4,547,189; 4,553,962; 4,573,970; 4,573,976; 4,578,061; 4,578,064; 4,580,561; 4,592,744; 4,594,073; 4,596,558; 4,597,753; 4,600,403; 4,601,708; 4,613,328; 4,620,540; 4,620,847; 4,624,660; 4,650,468; 4,658,830; 4,659,326; 4,664,651; 4,664,654; 4,666,436; 4,672,967; 4,681,565; 4,687,465; 4,687,467; 4,689,042; 4,699,614; 4,710,170; 4,723,937; 4,735,618; 4,738,663; 4,743,234; 4,744,955; 4,745,907; 4,747,829; 4,747,831; 4,753,636; 4,755,169; 4,758,227; 4,758,230; 4,758,231; 4,766,908; 4,767,407; 4,767,413; 4,770,655; 4,781,683; 4,781,685; 4,781,688; 4,784,640; 4,787,384; 4,787,893; 4,790,823; 4,790,827; 4,795,432; 4,795,433; 4,798,587; 4,799,921; 4,804,370; 4,808,169; 4,813,937; 4,813,940; 4,820,275; 4,820,286; 4,826,484; 4,826,489; 4,826,490; 4,828,548; 4,832,682; 4,832,693; 4,834,704; 4,834,718; 4,842,598; 4,846,811; 4,850,961; 4,850,968; 4,850,971; 4,850,976; 4,850,977; 4,850,994; 4,861,338; 4,863,427; 4,863,435; 4,863,436; 4,865,592; 4,874,372; 4,874,382; 4,883,466; 4,883,472; 4,886,499; 4,887,998; 4,892,107; 4,892,523; 4,894,054; 4,894,055; 4,898,589; 4,900,303; 4,900,307; 4,900,311; 4,902,279; 4,904,242; 4,906,236; 4,908,022; 4,909,794; 4,909,795; 4,911,706; 4,913,702; 4,915,702; 4,917,672; 4,919,146; 4,919,657; 4,923,443; 4,923,445; 4,927,414; 4,929,237; 4,929,241; 4,931,040; 4,932,944; 4,932,946; 4,932,947; 4,935,013; 4,935,014; 4,936,830; 4,941,879; 4,944,723; 4,944,725; 4,946,441; 4,950,240; 4,950,241; 4,950,250; 4,950,252; 4,955,866; 4,955,868; 4,955,869; 4,955,870; 4,961,728; 4,966,589; 4,966,592; 4,966,593; 4,973,310; 4,973,317; 4,976,704; 4,988,335; 4,988,339; 4,994,045; 4,998,921; 4,998,922; 5,000,736; 5,000,737; 5,002,548; 5,007,903; 5,011,475; 5,015,240; 5,017,187; 5,019,043; 5,019,044; 5,019,047; 5,019,048; 5,021,059; 5,024,665; 5,026,349; 5,030,208; 5,034,003; 5,037,306; 5,037,382; 5,037,393; 5,037,400; 5,041,094; 5,042,977; 5,045,066; 5,047,016; 5,049,133; 5,049,136; 5,053,010; 5,053,018; 5,055,102; 5,057,086; 5,057,089; 5,059,180; 5,059,185; 5,061,249; 5,061,251; 5,064,419; 5,067,490; 5,067,948; 5,071,353; 5,080,104; 5,084,027; 5,084,029; 5,084,030; 5,085,640; 5,085,641; 5,085,642; 5,088,986; 5,088,988; 5,092,843; 5,092,851; 5,092,852; 5,092,853; 5,098,382; 5,098,400; 5,098,401; 5,102,393; 5,102,397; 5,104,378; 5,104,380; 5,104,384; 5,104,385; 5,106,370; 5,106,372; 5,106,379; 5,108,378; 5,108,379; 5,112,307; 5,112,316; 5,114,404; 5,120,310; 5,120,314; 5,120,321; 5,122,118; 5,122,124; 5,125,898; 5,125,899; 5,127,910; 5,135,507; 5,135,510; 5,137,515; 5,137,516; 5,141,496; 5,143,414; 5,147,311; 5,147,326; 5,147,327; 5,149,323; 5,152,751; 5,156,599; 5,160,326; 5,163,916; 5,163,917; 5,163,918; 5,167,632; 5,167,641; 5,169,389; 5,169,392; 5,176,641; 5,176,655; 5,176,656; 5,176,657; 5,183,468; 5,183,469; 5,188,614; 5,190,526; 5,193,552; 5,195,982; 5,195,983; 5,195,985; 5,199,952; 5,201,708; 5,201,710; 5,205,826; 5,205,827; 5,207,646; 5,207,699; 5,209,739; 5,211,628; 5,211,629; 5,215,524; 5,215,533; 5,215,534; 5,215,535; 5,215,536; 5,217,437; 5,219,338; 5,221,262; 5,222,943; 5,222,947; 5,222,974; 5,224,936; 5,226,882; 5,228,883; 5,232,457; 5,232,458; 5,238,654; 5,242,388; 5,242,401; 5,242,416; 5,242,420; 5,246,428; 5,250,031; 5,256,152; 5,257,976; 5,261,894; 5,263,933; 5,267,961; 5,267,963; 5,269,761; 5,269,762; 5,269,766; 5,273,532; 5,273,538; 5,273,539; 5,273,541; 5,273,544; 5,279,554; 5,279,566; 5,279,577; 5,279,579; 5,279,581; 5,279,582; 5,279,583; 5,279,590; 5,282,793; 5,282,822; 5,282,827; 5,284,479; 5,290,233; 5,290,239; 5,290,240; 5,290,254; 5,292,314; 5,295,963; 5,295,965; 5,295,972; 5,295,973; 5,295,974; 5,295,975; 5,300,029; 5,300,030; 5,300,040; 5,300,045; 5,304,137; 5,304,138; 5,306,251; 5,306,258; 5,308,332; 5,311,841; 5,312,353; 5,312,366; 5,312,368; 5,312,370; 5,312,371; 5,312,372; 5,314,503; 5,318,538; 5,320,609; 5,322,517; 5,324,265; 5,328,475; 5,328,482; 5,328,484; 5,330,430; 5,334,149; 5,334,158; 5,334,173; 5,336,180; 5,336,187; 5,336,199; 5,338,303; 5,338,311; 5,342,310; 5,342,320; 5,344,407; 5,344,408; 5,346,475; 5,346,480; 5,346,481; 5,348,544; 5,352,200; 5,352,202; 5,352,203; 5,354,287; 5,356,387; 5,358,489; 5,360,410; 5,364,362; 5,364,370; 5,366,447; 5,368,568; 5,368,570; 5,368,571; 5,370,619; 5,370,626; 5,374,250; 5,378,240; 5,383,857; 5,385,550; 5,385,551; 5,385,557; 5,389,076; 5,389,085; 5,391,151; 5,391,183; 5,395,317; 5,395,337; 5,399,163; 5,401,246; 5,401,249; 5,401,251; 5,403,286; 5,403,287; 5,405,326; 5,405,327; 5,407,436; 5,409,466; 5,411,487; 5,415,638; 5,415,645; 5,415,648; 5,419,766; 5,419,773; 5,423,746; 5,425,715; 5,425,722; 5,429,611; 5,429,612; 5,429,613; 5,431,631; 5,431,632; 5,433,712; 5,445,618; 5,445,620; 5,451,210; 5,458,576; 5,458,580; 5,460,611; 5,462,531; 5,466,223; 5,468,227; 5,474,687; 5,478,314; 5,478,316; 5,478,328; 5,480,385; 5,480,387; 5,480,390; 5,482,039; 5,484,414; 5,486,163; 5,486,164; 5,487,732; 5,487,733; 5,487,734; 5,489,272; 5,492,536; 5,496,278; 5,501,672; 5,512,048; 5,512,050; 5,514,097; 5,514,107; 5,520,639; 5,520,649; 5,522,797; 5,522,812; 5,527,283; 5,527,284; 5,527,307; 5,529,189; 5,531,691; 5,531,692; 5,531,694; 5,531,704; 5,531,706; 5,533,975; 5,533,984; 5,536,243; 5,536,253; 5,536,257; 5,538,506; 5,538,508; 5,540,664; 5,540,666; 5,542,920; 5,542,927; 5,549,558; 5,549,568; 5,549,570; 5,549,572; 5,549,708; 5,558,648; 5,562,623; 5,562,624; 5,562,626; 5,562,631; 5,569,202; 5,569,203; 5,573,513; 5,575,770; 5,578,011; 5,578,014; 5,578,015; 5,582,591; 5,586,976; 5,591,133; 5,591,134; 5,591,138; 5,593,387; 5,593,390; 5,599,309; 5,599,313; 5,599,316; 5,599,318; 5,601,532; 5,601,535; 5,605,544; 5,609,577; 5,611,781; 5,611,782; 5,613,500; 5,613,951; 5,613,952; 5,615,771; 5,616,123; 5,616,132; 5,616,134; 5,616,135; 5,620,422; 5,620,425; 5,624,401; 5,624,405; 5,628,765; 5,630,803; 5,632,730; 5,632,733; 5,634,906; 5,634,909; 5,634,937; 5,637,092; 5,637,094; 5,643,220; 5,643,222; 5,647,851; 5,649,622; 5,651,774; 5,653,687; 5,653,688; 5,653,693; 5,656,031; 5,658,256; 5,658,257; 5,658,258; 5,658,259; 5,662,610; 5,662,617; 5,665,071; 5,665,075; 5,669,889; 5,672,155; 5,672,161; 5,681,291; 5,681,295; 5,688,240; 5,688,251; 5,693,016; 5,693,022; 5,693,023; 5,695,472; 5,704,911; 5,704,921;

5,707,393; 5,709,662; 5,709,667; 5,709,668; 5,713,866; 5,713,871; 5,713,872; 5,720,727; 5,725,498; 5,738,655; 5,741,223; 5,743,879; 5,743,887; 5,743,888; 5,743,891; 5,746,718; 5,749,854; 5,749,860; 5,755,692; 5,769,822; 5,769,827; 5,779,675; 5,779,677; 5,779,684; 5,788,677; 5,788,713; 5,792,107; 5,792,121; 5,792,122; 5,795,336; 5,797,885; 5,800,403; 5,807,334; 5,807,345; 5,807,352; 5,810,775; 5,810,784; 5,817,054; 5,817,070; 5,820,602; 5,823,997; 5,823,998; 5,827,293; 5,830,130; 5,836,911; 5,836,920; 5,843,036; 5,843,047; 5,848,990; 5,851,197; 5,853,390; 5,853,393; 5,855,839; 5,858,000; 5,865,227; 5,865,804; 5,868,711; 5,879,337; 5,882,342; 5,885,257; 5,891,052; 5,891,092; 5,891,097; 5,891,105; 5,897,508; 5,899,885; 5,899,886; 5,908,404; 5,908,408; 5,910,131; 5,911,706; 5,919,166; 5,921,959; 5,921,960; 5,921,961; 5,921,963; 5,921,964; 5,925,019; 5,928,188; 5,928,194; 5,928,205; 5,931,813; 5,938,638; 5,938,639; 5,941,850; 5,944,692; 5,944,693; 5,951,522; 5,954,699; 5,957,892; 5,957,895; 5,957,897; 5,960,797; 5,961,491; 5,971,953; 5,976,111; 5,980,487; 5,980,488; 5,980,491; 5,980,494; 5,984,899; 5,984,900; 5,989,219; 5,989,221; 5,993,417; 5,993,418; 5,997,500; 5,997,511; 5,997,513; 6,001,080; 6,007,474; 6,010,486; 6,010,487; 6,015,396; 6,015,438; 6,017,325; 6,022,337; 6,033,386; 6,033,387; 6,036,674; 6,039,713; 6,050,974; 6,050,977; 6,056,716; 6,056,724; 6,056,734; 6,063,040; 6,063,053; 6,066,115; 6,068,616; 6,074,360; 6,074,369; 6,074,370; 6,077,245; 6,080,135; 6,083,199; 6,083,200; 6,086,562; 6,086,569; 6,090,077; 6,090,078; 6,090,080; 6,093,172; 6,099,500; 6,099,503; 6,099,504; 6,102,844; 6,113,574; 6,117,112; 6,117,113; 6,126,637; 6,129,710; 6,142,972; 6,149,626; 6,149,629; 6,156,008; 6,156,010; 6,156,013; 6,156,015; 6,159,161; 6,159,181; 6,159,185; 6,171,284; 6,179,812; 6,183,444; 6,183,446; 6,186,980; 6,192,891; 6,193,695; 6,206,856; 6,206,857; 6,210,369; 6,217,550; 6,217,559; 6,221,044; 6,221,051; 6,221,052; 6,224,576; 6,228,054; 6,228,055; 6,235,006; 6,241,707; 6,241,708; 6,254,575; 6,254,580; 6,258,056; 6,261,264; 6,261,265; 6,267,748; 6,270,472; 6,270,481; 6,273,870; 6,280,399; 6,280,420; 6,280,421; 6,283,941; 6,293,925; 6,299,601; 6,309,374; 6,309,375; 6,312,409; 6,315,113; 6,319,233; 6,319,234; 6,322,536; 6,325,781; 6,325,789; 6,331,173; 6,332,875; 6,344,031; 6,356,783; 6,361,525; 6,368,303; 6,371,938; 6,379,336; 6,387,078; 6,402,716; 6,409,701; 6,409,703; 6,409,706; 6,412,490; 6,413,236; 6,413,237; 6,416,323; 6,416,497; 6,419,658; 6,428,463; 6,428,517; 6,432,035; 6,432,082; 6,432,087; 6,436,068; 6,440,098; 6,443,929; 6,447,480; 6,454,743; 6,458,105; 6,461,331; 6,461,333; 6,468,247; 6,475,194; 6,478,780; 6,482,176; 6,485,469; 6,485,474; 6,494,863; 6,500,155; 6,508,755; 6,511,454; 6,514,230; 6,517,516; 6,517,517; 6,524,278; 6,527,734; 6,527,742; 6,530,896; 6,530,904; 6,537,249; 6,537,252; 6,544,234; 6,547,764; 6,551,275; 6,551,276; 6,551,278; 6,554,798; 6,558,351; 6,558,357; 6,565,533; 6,565,538; 6,569,115; 6,572,584; 6,572,585; 6,575,939; 6,579,256; 6,582,405; 6,584,910; 6,585,690; 6,585,693; 6,585,702; 6,589,158; 6,592,508; 6,592,555; 6,592,556; 6,595,962; 6,599,268; 6,599,269; 6,599,272; 6,605,058; 6,605,067; 6,605,073; 6,607,508; 6,607,509; 6,613,019; 6,613,022; 6,616,630; 6,616,638; 6,616,639; 6,620,136; 6,620,137; 6,620,138; 6,623,455; 6,623,458; 6,623,459; 6,626,864; 6,629,957; 6,629,959; 6,632,198; 6,637,587; 6,638,248; 6,638,255; 6,641,561; 6,645,181; 6,652,482; 6,656,164; 6,659,975; 6,659,982; 6,663,593; 6,669,666; 6,673,034; 6,673,044; 6,673,049; 6,678,550; 6,679,863; 6,679,864; 6,685,676; 6,685,677; 6,689,091; 6,689,106; 6,689,107; 6,689,108; 6,692,470; 6,692,471; 6,699,218; 6,702,784; 6,706,011; 6,706,015; 6,706,019; 6,709,416; 6,712,787; 6,712,788; 6,716,191; 6,716,197; 6,716,198; 6,719,721; 6,719,728; 6,719,730; 6,723,068; 6,723,072; 6,726,655; 6,726,658; 6,726,661; 6,726,662; 6,730,059; 6,736,800; 6,740,059; 6,743,203; 6,749,833; 6,752,782; 6,752,784; 6,752,798; 6,761,706; 6,767,336; RE 33,585; RE 34,335; RE 34,936; RE36,398; RE 36,447; RE 37,110; RE 37,252 and RE 37,487.

SUMMARY OF THE INVENTION

The present invention seeks to provide an improved automatic needle device. There is thus provided in accordance with a preferred embodiment of the present invention an automatic needle device including a housing element, at least one resilient element arranged to be located within the housing element, at least one needle bearing element adapted, when actuated, to be displaced by the at least one resilient element with respect to the housing element from a non-penetration position to a penetration position and a needle guard adapted for positioning with respect to the housing element and wherein displacement of the needle guard is operative to actuate displacement of the at least one needle bearing element from the non-penetration position to the penetration position.

In accordance with another preferred embodiment of the present invention rearward displacement of the needle guard is operative to actuate displacement of the at least one needle bearing element from the non-penetration position to the penetration position.

In accordance with another preferred embodiment of the present invention the automatic needle device also includes a safety element adapted to prevent inadvertent actuation of displacement of the at least one needle bearing element. Additionally, the safety element prevents inadvertent rearward displacement of the needle guard.

In accordance with yet another preferred embodiment of the present invention the at least one resilient element includes a unitary resilient element. Alternatively, the at least one resilient element includes first and second coil springs.

In accordance with still another preferred embodiment of the present invention the housing element includes an injection device engagement portion. Additionally, the housing element and the at least one needle bearing element together define a fluid pathway from the injection device engagement portion through the needle at least when the needle bearing element is in both the non-penetration position and the penetration position.

In accordance with another preferred embodiment of the present invention the needle guard is displaceable by the at least one resilient element.

In accordance with a further preferred embodiment of the present invention the at least one resilient element includes first and second compression springs which provide selectable forward displacement to the at least one needle bearing element.

In accordance with yet another preferred embodiment of the present invention the needle bearing element includes a hub portion and a needle adhered thereto and extending through a septum.

In accordance with still another preferred embodiment of the present invention the automatic needle device also includes a safety tab operative for disabling actuation of the automatic needle device. In accordance with yet another preferred embodiment of the present invention, the safety tab includes a spacer portion and a tab portion.

There is also provided in accordance with another preferred embodiment of the present invention an automatic needle device including a housing element, at least one needle bearing element adapted, when actuated, to be displaced with respect to the housing element from a non-penetration position to a penetration position and a needle guard adapted for positioning with respect to the at least one needle bearing element in a mutually locked needle guarding orientation, whereby displacement of the needle guard relative to the housing requires corresponding displacement of the at least one needle bearing element.

There is further provided in accordance with yet another preferred embodiment of the present invention an automatic needle device including a housing element, at least one needle bearing element adapted, when actuated, to be displaced with respect to the housing element from a non-penetration position to a penetration position and a needle guard adapted for positioning with respect to the at least one needle bearing element and with respect to the housing element in a mutually locked needle guarding orientation, whereby displacement of the needle guard in a first direction relative to the housing is prevented by engagement of the needle guard with the at least one needle bearing element and displacement of the needle guard in a second direction relative to the housing, opposite to the first direction, is prevented by engagement of the needle guard with the housing element.

There is even further provided in accordance with still another preferred embodiment of the present invention an automatic needle device including a housing element adapted to be connected to an external injection device, at least one needle bearing element adapted, when actuated, to be displaced with respect to the housing element from a non-penetration position to a penetration position and a needle guard adapted for positioning with respect to at least one of the at least one needle bearing element and the housing element in a needle guarding orientation.

There is still further provided in accordance with another preferred embodiment of the present invention an injection device including a housing element, a unitary resilient element arranged to be located within the housing element, the unitary resilient element including a septum portion and at least one displacement actuating portion, and at least one needle bearing element including a needle sealingly engaging the septum portion, the at least one needle bearing element adapted, when actuated, to be displaced by the at least one displacement actuating portion of the unitary resilient element with respect to the housing element from a non-penetration position to a penetration position.

In accordance with another preferred embodiment of the present invention the housing element is an integrally formed element having a generally cylindrical configuration and is generally top-to-bottom and side-to-side symmetric about a longitudinal axis. Alternatively or additionally, the housing element includes a rearward generally tubular portion which terminates in an open back and defines forwardly thereof a generally cylindrical portion, whose outer configuration includes top and bottom grip regions. Additionally or alternatively, the housing element includes first and second forwardly and rearwardly tapered side protrusions.

In accordance with another preferred embodiment of the present invention the automatic needle device also includes, at an inner surface of the generally cylindrical portion, forward and rearward inwardly extending transverse ribs and a plurality of inwardly extending longitudinal slots.

In accordance with yet another preferred embodiment of the present invention the automatic needle device also includes, at an interior of the generally tubular portion, a generally cylindrical bore which communicates via a tapered interface with a forward bore, disposed interiorly of the cylindrical portion, the cylindrical bore being arranged to receive a septum.

In accordance with another preferred embodiment of the present invention apertures are formed in cylindrical walls of the cylindrical bore in alignment along a line extending transversely to a longitudinal axis of the housing element.

In accordance with still another preferred embodiment of the present invention a forward-facing back wall surface of the generally cylindrical portion defines a seat for the at least one resilient element.

In accordance with a further preferred embodiment of the present invention the housing element is formed with a pair of side-to-side symmetric windows, to allow viewing the tip of a needle held by the needle bearing element.

In accordance with another preferred embodiment of the present invention the needle bearing element includes a needle hub and a needle. Additionally, the needle bearing element has a generally cylindrical configuration and is top-to-bottom and side-to-side symmetric about a longitudinal axis. Additionally or alternatively, the needle bearing element defines a generally tubular body having formed thereon a pair of up-down mutually spaced, forwardly facing, outwardly extending hook protrusions. In accordance with another preferred embodiment of the present invention the protrusions are each associated with a rearward facing rib.

In accordance with yet another preferred embodiment of the present invention a rearwardly extending arm is formed at both a top and a bottom of the tubular body, each arm including, adjacent an extreme rearwardly facing end thereof, a tapered inwardly facing tooth and forwardly thereof an outwardly facing tooth, having a transversely extending rearwardly facing surface.

In accordance with a further preferred embodiment of the present invention top and bottom pairs of outwardly facing ribs are formed on the tubular portion, adjacent respective rearward facing ribs, the outwardly facing ribs being operative to slidably locate the needle bearing element within the needle guard.

In accordance with yet a further preferred embodiment of the present invention the tubular body defines a generally open back and a forward facing wall portion adjacent in which is formed a recess, which communicates with a narrow axial bore, arranged to receive the needle, which extends therethrough.

In accordance with another preferred embodiment of the present invention a rearward facing external wall portion, located at a rearward end of the tubular body, defines a seat for the at least one resilient element.

In accordance with yet a further preferred embodiment of the present invention the needle guard has a generally cylindrical configuration and is top-to-bottom and side-to-side symmetric about a longitudinal axis. Additionally or alternatively, the needle guard defines a generally tubular body having formed thereon a plurality of circumferentially spaced, longitudinally extending, outward facing ribs, having rearward facing ends, the outward facing ribs being adapted to slidably locate the needle guard within inwardly extending longitudinal slots of the housing element.

In accordance with still another preferred embodiment of the present invention extending rearwardly of the outwardly facing ribs there is provided a curved rearward facing portion having a pair of inwardly facing ribs formed therein, and, extending rearwardly of the ribs, there is formed a symmetrically curved rearward facing portion having a pair of ribs formed therein. Additionally or alternatively, the curved rearward facing portions together with the rearward facing ends define a seat for a spring forming part of the at least one resilient element.

In accordance with yet another preferred embodiment of the present invention the inwardly facing ribs are operative to slidably locate the needle bearing element within the needle guard, by allowing the outwardly facing ribs to slide therein.

In accordance with still a further preferred embodiment of the present invention a rearwardly extending arm is formed at each side of the tubular body, each of the arms including adjacent an extreme rearwardly facing end thereof, an outwardly facing tooth, having an inclined forward surface and a transversely extending rearwardly facing surface. Additionally or alternatively, the tubular body defines a generally open back and a forward facing wall portion, defining an injection site engagement surface.

In accordance with yet another preferred embodiment of the present invention the injection site engagement surface includes a pair of mutually concentric circles of mutually spaced forwardly extending protrusions and the forward facing wall portion is formed with an axial bore, arranged to allow a needle to extend therethrough.

In accordance with even a further preferred embodiment of the present invention the needle guard is formed with a pair of side-to-side symmetric windows, to allow viewing of the tip of a needle.

In accordance with still another preferred embodiment of the present invention, in a pre-use operative orientation suitable for storage, the housing element is joined to the needle bearing element by snap fit engagement of inner facing teeth formed on the needle bearing element into apertures formed in cylindrical walls of the housing element.

In accordance with a further preferred embodiment of the present invention the at least one resilient element includes first and second compression springs, the first compression spring being maintained under compression between forward-facing back wall surface of a generally cylindrical portion of the housing element and a rearward facing wall portion of the needle bearing element and the second compression spring being maintained under compression between the forward facing back wall surface and rearward facing ends of the needle guard, which is slidably retained against disassembly forward movement by the positioning of curved rearward facing portions thereof immediately rearward of the inner facing teeth of the needle bearing element In accordance with another preferred embodiment of the present invention the needle bearing element is retained in its place by engagement of rearwardly outwardly facing surfaces of the inner facing teeth with curved rearward facing portions of the needle guard, thus preventing rearwardly extending arms of the needle bearing element from bending outwardly and releasing the snap fit engagement of the inner facing teeth and apertures formed in the cylindrical walls of the cylindrical bore of the housing element. Additionally or alternatively, due to engagement of the needle guard with an injection site on a body, the needle guard is forced, against the urging of the at least one resilient element, to move axially in a rearward direction with respect to the remainder of the automatic needle device, thus sliding the curved rearward facing portions thereof further rearward of the outwardly facing teeth of the needle bearing element, thus allowing the arms of the needle bearing element to cantilever outwardly.

In accordance with yet another preferred embodiment of the present invention at all times the needle sealingly and slidably engages a septum.

BRIEF DESCRIPTION OF THE DRAWINGS

The present invention will be understood and appreciated more fully from the following detailed description, taken in conjunction with the drawings in which:

FIGS. 7A and 7B are respective top and side view simplified planar illustrations of the needle hub assembly of FIGS. 6A and 6B;

FIGS. 8A and 8B are sectional illustrations taken along respective section lines and directions VIIIA-VIIIA and VIIIB-VIIIB in FIGS. 7A and 7B;

FIGS. 9A and 9B are pictorial sectional illustrations taken along respective section lines and directions IXA-IXA and IXB-IXB in FIG. 6A;

FIGS. 15A and 15B are simplified assembled view illustrations of the automatic needle device of FIGS. 1 and 14A in a pre-use operative orientation;

FIGS. 17A and 17B are sectional illustrations taken along respective section lines and directions XVIIA-XVIIA and XVIIB-XVIIB in FIGS. 16A and 16B;

FIG. 18 is a simplified pictorial illustration of the automatic needle device of FIGS. 1 and 14B in an injection site engagement operative orientation coupled to a syringe;

FIGS. 19A and 19B are respective top and side view simplified planar illustrations of the automatic needle device of FIG. 18 coupled to a syringe FIGS. 20A and 20B are sectional illustrations taken along respective section lines and directions XXA-XXA and XXB-XXB in FIGS. 19A and 19B;

FIG. 21 is a simplified pictorial illustration of the automatic needle device of FIGS. 1 and 14C in a needle actuated operational orientation;

FIGS. 22A and 22B are respective top and side view simplified planar illustrations of the automatic needle device of FIG. 21;

FIGS. 23A and 23B are sectional illustrations taken along respective section lines and directions XXIIIA-XXIIIA and XXIIIB-XXIIIB in FIGS. 22A and 22B;

FIGS. 25A and 25B are respective top and side view simplified planar illustrations of the automatic needle device of FIG. 24;

FIGS. 26A and 26B are sectional illustrations taken along respective section lines and directions XXVIA-XXVIA and XXVIB-XXVIB in FIGS. 25A and 25B;

FIG. 27 is a simplified exploded view illustration of an automatic needle device constructed and operative in accordance with another preferred embodiment of the present invention;

FIG. 45 is a simplified assembled view pictorial illustration of the automatic needle device of FIGS. 27 and 44A in a pre-use operative orientation, coupled to a syringe and prior to removal of a safety tab;

FIGS. 46A and 46B are respective top and side view simplified planar illustrations of the automatic needle device of FIG. 45;

FIGS. 47A and 47B are sectional illustrations taken along respective section lines and directions XLVIIA-XLVIIA and XLVIIB-XLVIIB in FIGS. 46A and 46B;

FIG. 47C is simplified illustration corresponding to FIG. 46A with the needle guard element hidden;

FIG. 47D is a partially cut-away illustration of the needle guard element and the needle hub assembly of FIG. 46B;

FIG. 48 is a simplified pictorial illustration of the automatic needle device of FIGS. 27 and 44B in an injection site engagement operative orientation following removal of the safety tab;

FIGS. 49A and 49B are respective top and side view simplified planar illustrations of the automatic needle device of FIG. 48;

FIGS. 50A and 50B are sectional illustrations taken along respective section lines and directions LA-LA and LB-LB in FIGS. 49A and 49B;

FIG. 50C is simplified illustration corresponding to FIG. 49A with the needle guard element hidden;

FIG. 50D is a partially cut-away illustration of the needle guard element and the needle hub assembly of FIG. 49B;

FIG. 51 is a simplified pictorial illustration of the automatic needle device of FIGS. 27 and 44C in a needle actuated operational orientation;

FIGS. 52A and 52B are respective top and side view simplified planar illustrations of the automatic needle device of FIG. 51;

FIGS. 53A and 53B are sectional illustrations taken along respective section lines and directions LIIIA-LIIIA and LIIIB-LIIIB in FIGS. 52A and 52B;

FIG. 53C is a simplified illustration of FIG. 52A with the needle guard element hidden;

FIG. 53D, is a partially cut-away illustration corresponding to the needle guard element and the needle hub assembly of FIG. 52B;

FIGS. 55A and 55B are respective top and side view simplified planar illustrations of the automatic needle device of FIG. 54;

FIGS. 56A and 56B are sectional illustrations taken along respective section lines and directions LVIA-LVIA and LVIB-LVIB in FIGS. 55A and 55B;

FIG. 56C is a simplified illustration corresponding to FIG. 55A with the needle guard element hidden;

FIG. 56D is a partially cut-away illustration of the needle guard element and the needle hub assembly of FIG. 55B;

FIGS. 58A and 58B are respective top and side view simplified planar illustrations of the automatic needle device of FIG. 57;

FIGS. 59A and 59B are sectional illustrations taken along respective section lines and directions LIXA-LIXA and LIXB-LIXB in FIGS. 58A and 58B;

FIG. 59C is a simplified illustration corresponding to FIG. 58A with the needle guard element hidden;

FIG. 59D is a partially cut-away illustration of the needle guard element and the needle hub assembly of FIG. 58B;

FIGS. 62A and 62B are sectional illustrations taken along respective section lines and directions LXIIA-LXIIA and LXIIB-LXIIB in FIGS. 61A and 61B;

FIG. 62C is simplified illustration corresponding to FIG. 61A with the needle guard element hidden;

FIG. 62D is a partially cut-away of the needle guard element and the needle hub assembly of FIG. 61B;

FIG. 67 is a simplified pictorial illustration of the automatic needle device of FIG. 63 in an injection site engagement operative orientation coupled to a syringe;

FIGS. 68A and 68B are respective top and side view simplified planar illustrations of the automatic needle device of FIG. 67 coupled to a syringe FIGS. 69A and 69B are sectional illustrations taken along respective section lines and directions LXIXA-LXIXA and LXIXB-LXIXB in FIGS. 68A and 68B;

FIGS. 71A and 71B are respective top and side view simplified planar illustrations of the automatic needle device of FIG. 70;

FIGS. 72A and 72B are sectional illustrations taken along respective section lines and directions LXXIIA-LXXIIA and LXXIIB-LXXIIB in FIGS. 71A and 71B;

FIGS. 75A and 75B are sectional illustrations taken along respective section lines and directions LXXVA-LXXVA and LXXVB-LXXVB in FIGS. 74A and 74B.

DETAILED DESCRIPTION OF PREFERRED EMBODIMENTS

Reference is now made to FIGS. 1-13B, which illustrate the constituent elements of an automatic needle device constructed and operative in accordance with a preferred embodiment of the present invention.

Figure 1:
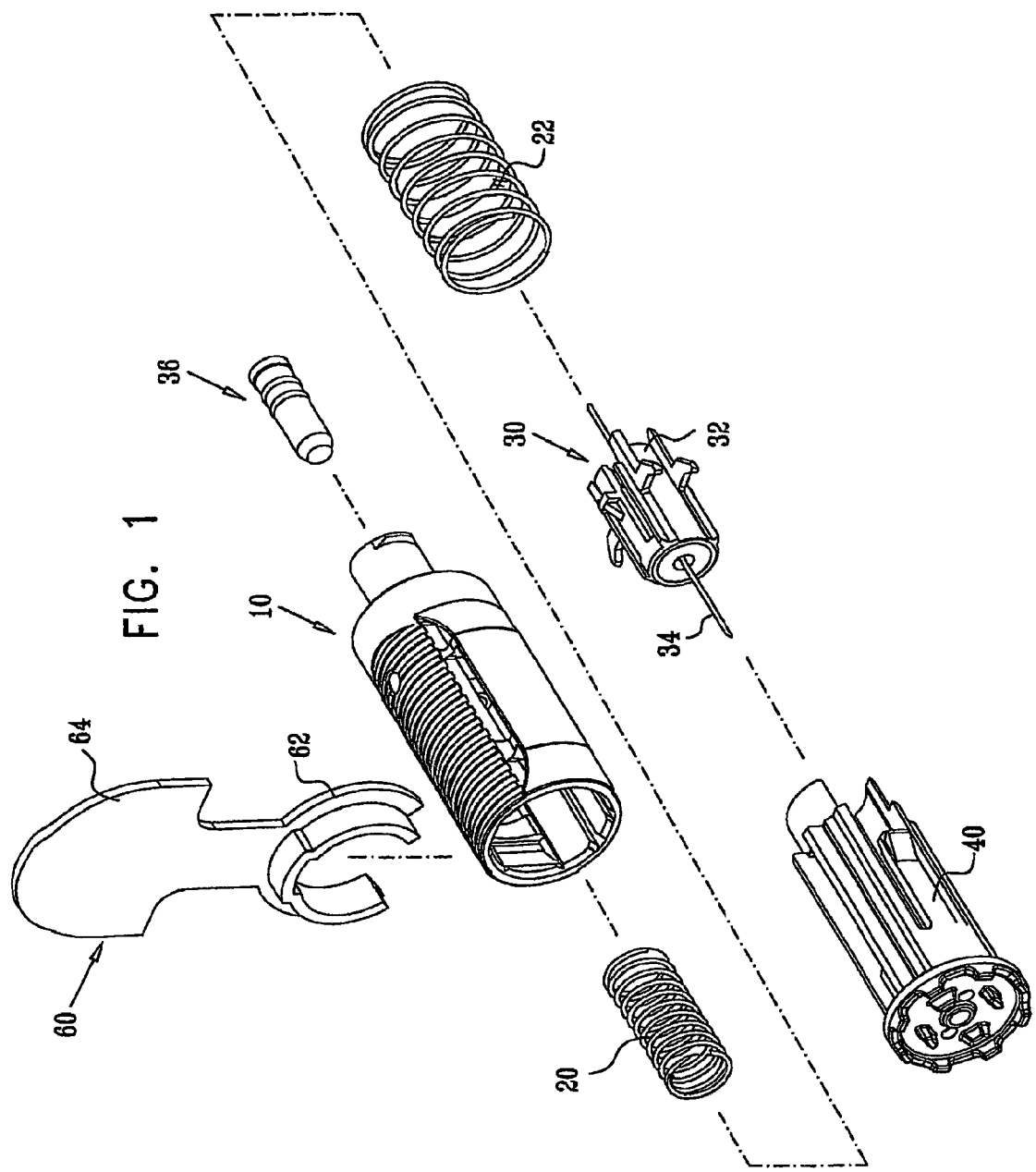
FIG. 1 is a simplified exploded view illustration of an automatic needle device constructed and operative in accordance with a preferred embodiment of the present invention.

As seen with particular clarity in FIG. 1, the automatic needle device comprises a housing element 10 into which are generally coaxially seated respective first and second compression springs 20 and 22, which provide selectable forward displacement to a needle hub assembly 30, which includes a hub portion 32 and a needle 34 adhesively adhered thereto and extending rearwardly through a septum 36, and to a needle guard element 40. Alternatively, needle hub portion 32 may be injected onto the needle, by a method such as insert molding.

A safety tab 60 including a tubular portion 62 and a tab portion 64 is preferably mounted onto the forward section of housing element 10, thus disabling actuation of the automatic needle device. The automatic needle device is only functional once the safety tab is removed, as described hereinbelow.

It will be appreciated by persons skilled in the art that safety tab 60 can be formed of any suitable material, for example such as polypropylene, and may designed in many different shapes, such as a portion which is inserted into a slot between the needle guard element 40 and the housing element 10, as a stand alone injection molded part, or as an integral part of any suitable part of the automatic needle device such as the housing element 10 as described e.g. hereinabelow with reference to FIGS. 27-62D, the needle guard element 40 or the needle hub 32.

It will additionally be appreciated by those skilled in the art that compression springs 20 and 22 may be replaced with a resilient element as described hereinbelow with reference to FIGS. 27-62D. Alternatively, compression springs 20 and 22 may be replaced by tension springs, elastomeric compression springs or plastic springs which may be integrated into housing element 10, into needle hub portion 32 or into needle guard element 40.

Figure 2A:
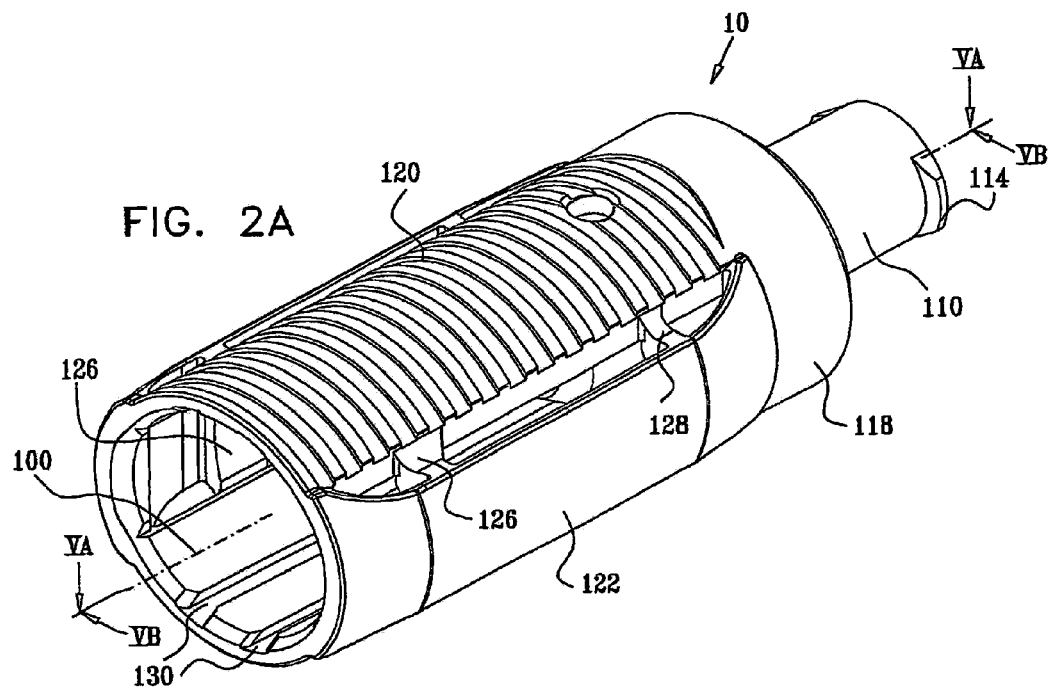
FIGS. 2A and 2B are simplified pictorial illustrations of a housing element which forms part of the automatic needle device of FIG. 1.
Figure 2B:
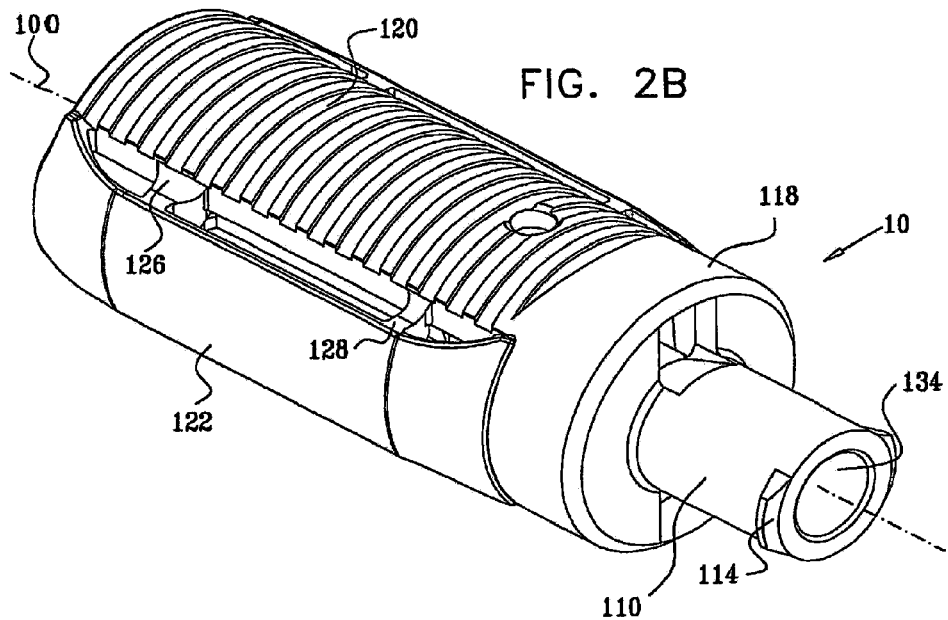
Figure 3A:
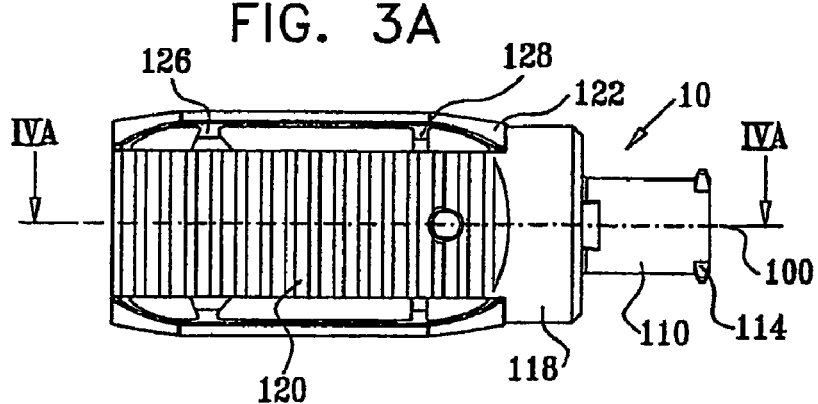
FIGS. 3A and 3B are respective top and side view simplified planar illustrations of the housing element of FIGS. 2A and 2B.
Figure 3B:
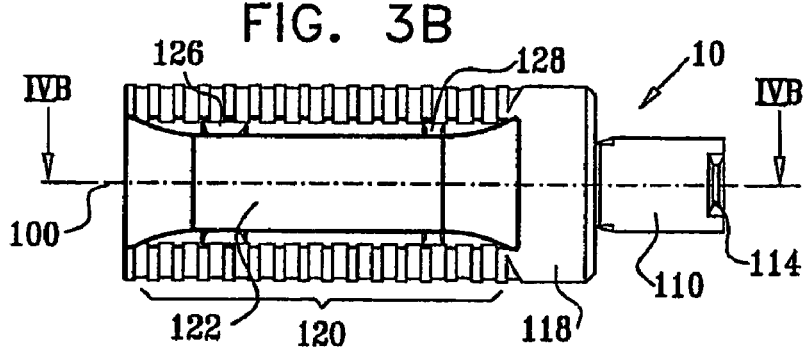
Figure 4A:
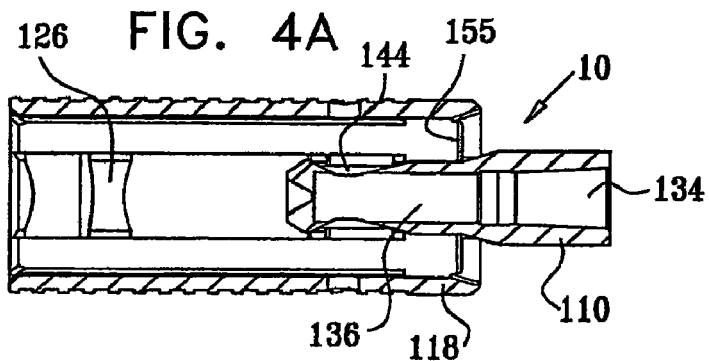
FIGS. 4A, 4B are sectional illustrations taken along respective section lines and directions IVA-IVA and IVB-IVB in FIGS. 3A and 3B.
Figure 4B:
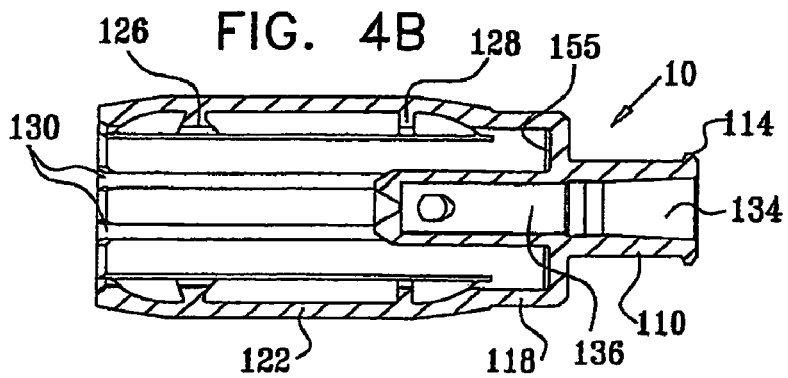
Figure 5A:
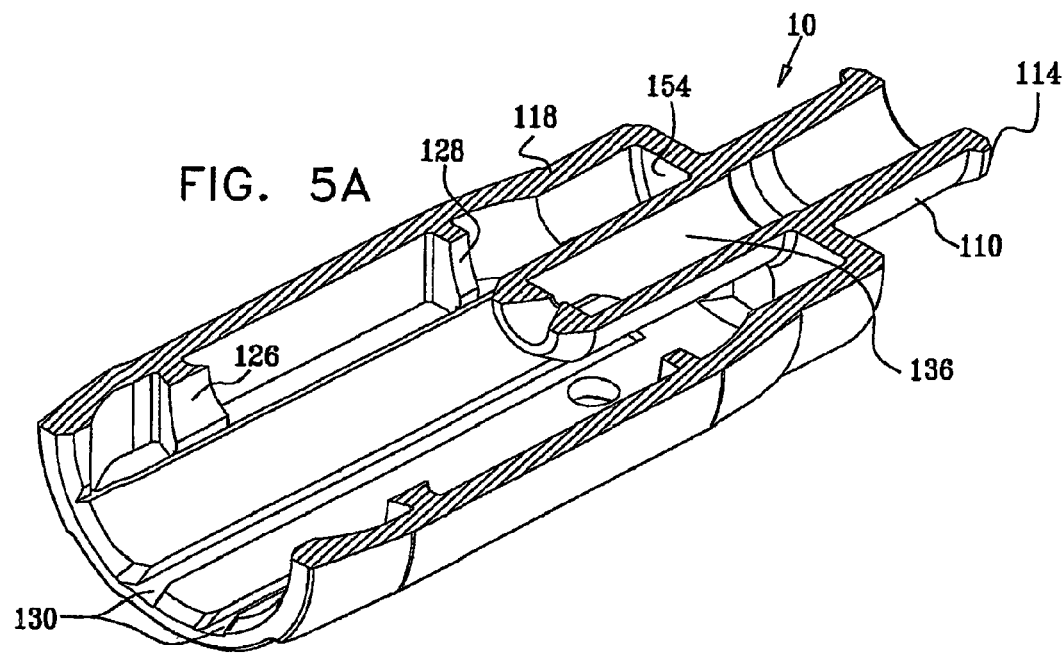
FIGS. 5A and 5B are pictorial sectional illustrations taken along respective section lines and directions VA-VA and VB-VB in FIG. 2A.
Figure 5B:
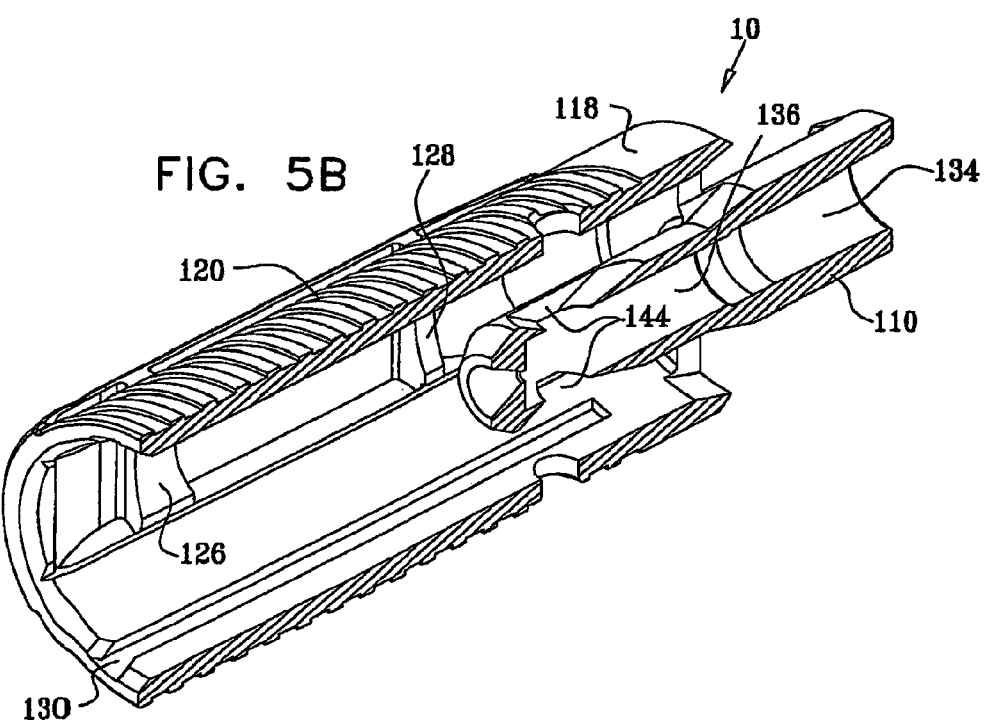

Reference is now made to FIGS. 2A and 2B, which are simplified pictorial illustrations of a preferred housing element 10 which forms part of the automatic needle device of FIG. 1, to FIGS. 3A and 3B are respective top and side view simplified planar illustrations thereof, to FIGS. 4A and 4B which are sectional illustrations taken along respective section lines and directions IVA-IVA and IVB-IVB in FIGS. 3A and 3B and to FIGS. 5A and 5B which are pictorial sectional illustrations taken along respective section lines and directions VA-VA and VB-VB in FIG. 2A.

As seen in FIGS. 2A-5B, the housing element 10 preferably is an integrally formed element, preferably injection molded of plastic. Housing element 10 preferably has a generally cylindrical configuration and is preferably top-to-bottom and side-to-side symmetric about a longitudinal axis 100.

Housing element 10 preferably includes a rearward generally tubular portion 110, which terminates in an open back and defines generally symmetric side-facing tabs 114. Forward of rearward generally tubular portion 110 there is provided a generally cylindrical portion 118, whose outer configuration preferably includes top and bottom grip regions 120, which are ribbed in a direction transverse to longitudinal axis 100 and first and second forwardly and rearwardly tapered side protrusions 122.

At an inner surface of generally cylindrical portion 118 there are provided forward and rearward inwardly extending transverse ribs 126 and 128 and a plurality of inwardly extending longitudinal slots 130. The interior of tubular portion 110 defines a generally cylindrical bore 134. Bore 134 communicates via a tapered interface with a forward bore 136, disposed interiorly of cylindrical portion 118, which is arranged to receive septum 36. Bore 136 has a circular cross section which is slightly smaller than that of bore 134.

Apertures 144 are formed in the cylindrical walls of bore 136 in alignment along a line extending transversely to longitudinal axis 100. A forward-facing back wall surface 154 of generally cylindrical portion 118 defines a spring seat for springs 20 and 22.

The housing element 10 may optionally be formed with a pair of side-to-side symmetric windows, to allow viewing of the tip of the needle 34, for example, when purging air bubbles from syringe 50. Alternatively, housing element 10 may be formed of a transparent material.

Figure 6A:
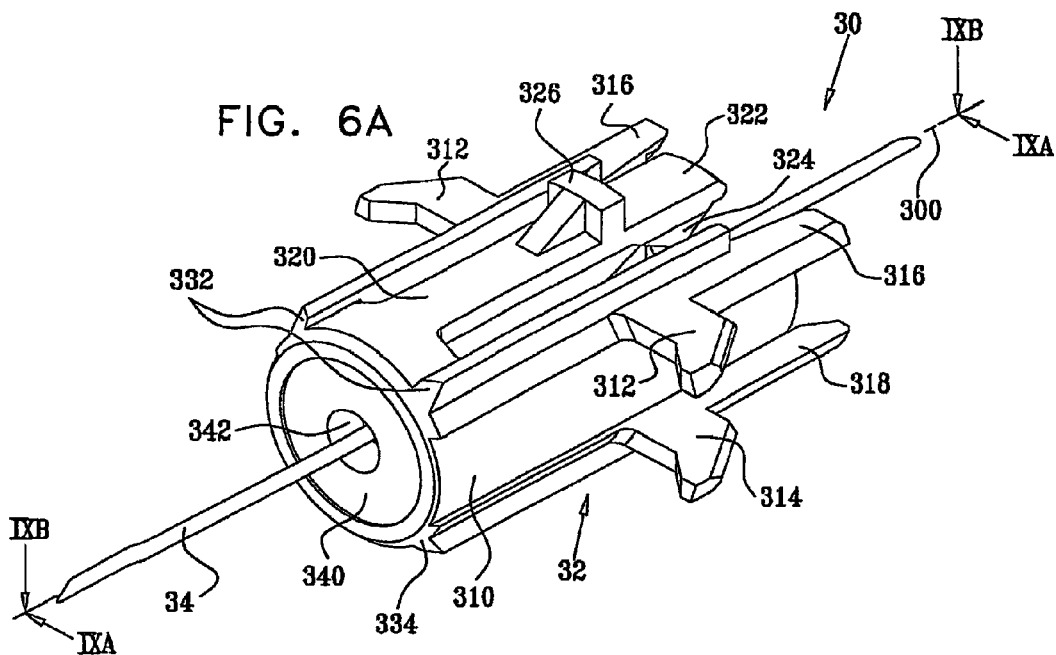
FIGS. 6A and 6B are simplified pictorial illustrations of a needle hub assembly which forms part of the automatic needle device of FIG. 1.
Figure 6B:
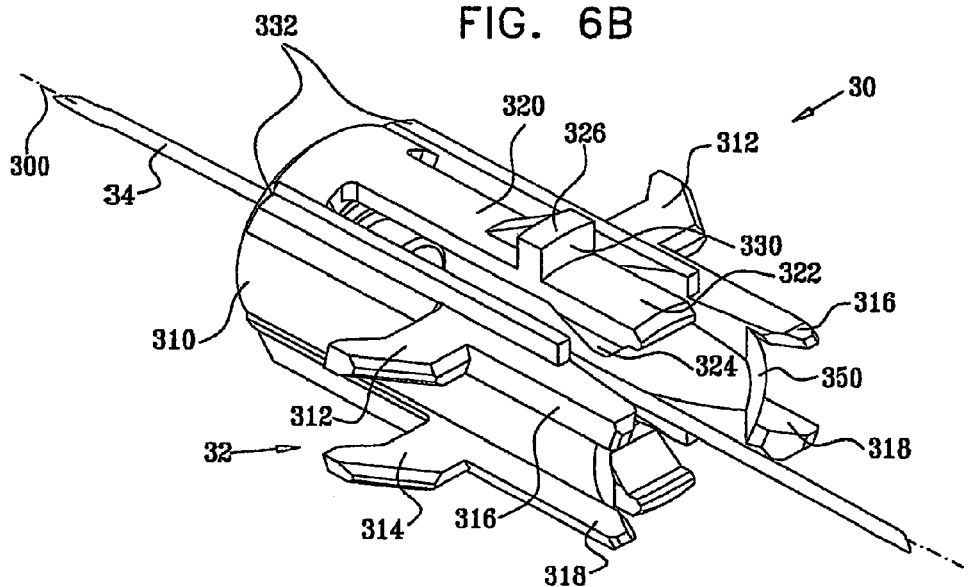

Reference is now made to FIGS. 6A and 6B, which are simplified pictorial illustrations of a needle hub assembly 30 which forms part of the automatic needle device of FIG. 1, to FIGS. 7A and 7B, which are respective top and side view simplified planar illustrations of the needle hub assembly of FIGS. 6A and 6B, to FIGS. 8A and 8B, which are sectional illustrations taken along respective section lines and directions VIIIA-VIIIA and VIIIB-VIIIB in FIGS. 7A and 7B and to FIGS. 9A and 9B, which are pictorial sectional illustrations taken along respective section lines and directions IXA-IXA and IXB-IXB in FIG. 6A.

As seen in FIGS. 6A-9B, the needle hub assembly 30 preferably comprises a needle hub 32, which is an integrally formed element, preferably injection molded of plastic, and a needle 34. Needle hub assembly 30 preferably has a generally cylindrical configuration and is preferably top-to-bottom and side-to-side symmetric about a longitudinal axis 300, which, when assembled together with housing element 10, is coaxial with longitudinal axis 100 (FIGS. 2A-5B).

Needle hub assembly 30 preferably defines a generally tubular body 310. A pair of up-down mutually spaced, forwardly facing, outwardly extending hook protrusions 312 and 314 is formed on each side of tubular portion 310. Protrusions 312 and 314 are each associated with a rearward facing rib, here designated 316 and 318 respectively.

A rearwardly extending arm 320 is formed at both the top and the bottom of tubular body 310. Each arm includes, adjacent an extreme rearwardly facing end 322 thereof, a tapered inwardly facing tooth 324 and forwardly thereof an outwardly facing tooth 326, having a transversely extending rearwardly facing surface 330.

Top and bottom pairs of outwardly facing ribs 332 and 334 are preferably formed on tubular portion 310, adjacent rearward facing ribs 316 and 318 respectively. Outwardly facing ribs 332 and 334 are operative to slidably locate needle hub assembly 30 within needle guard element 40. Tubular body 310 defines a generally open back and a forward facing wall portion 340 adjacent in which is formed a recess 342, which communicates with a narrow axial bore 344, arranged to receive needle 34, which extends therethrough and is held in place, preferably by an adhesive, which is located in recess 342. A rearward facing external wall portion 350, located at the rearward end of tubular body 310, defines a spring seat for spring 20, which is partially surrounded by rearward facing ends of ribs 316 and 318.

Figure 10A:
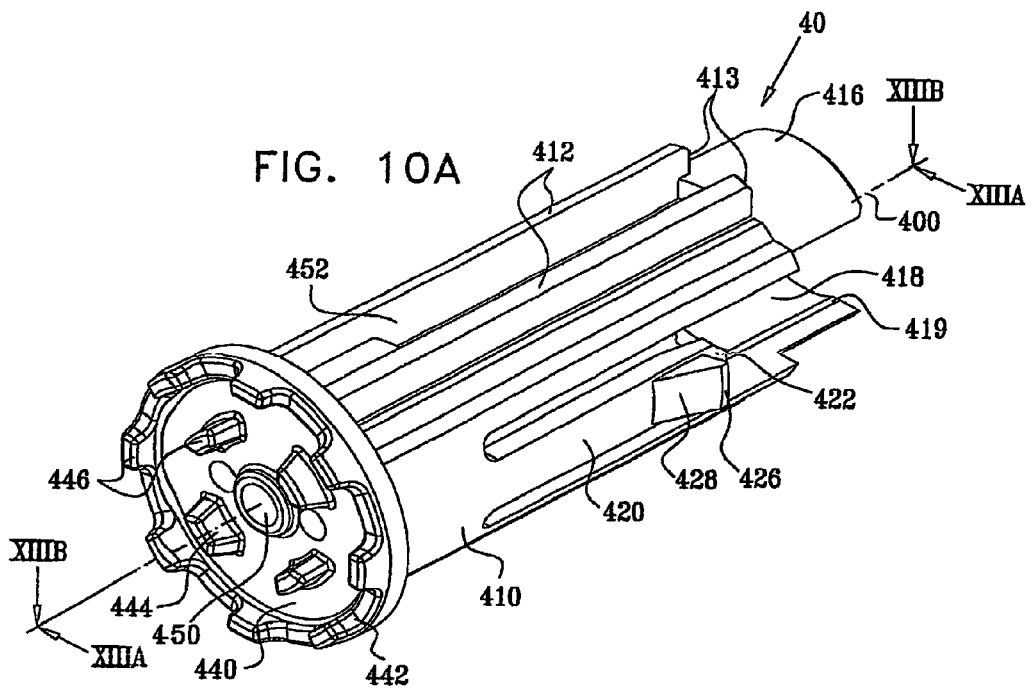
FIGS. 10A and 10B are simplified pictorial illustrations of a needle guard element which forms part of the automatic needle device of FIG. 1.
Figure 10B:
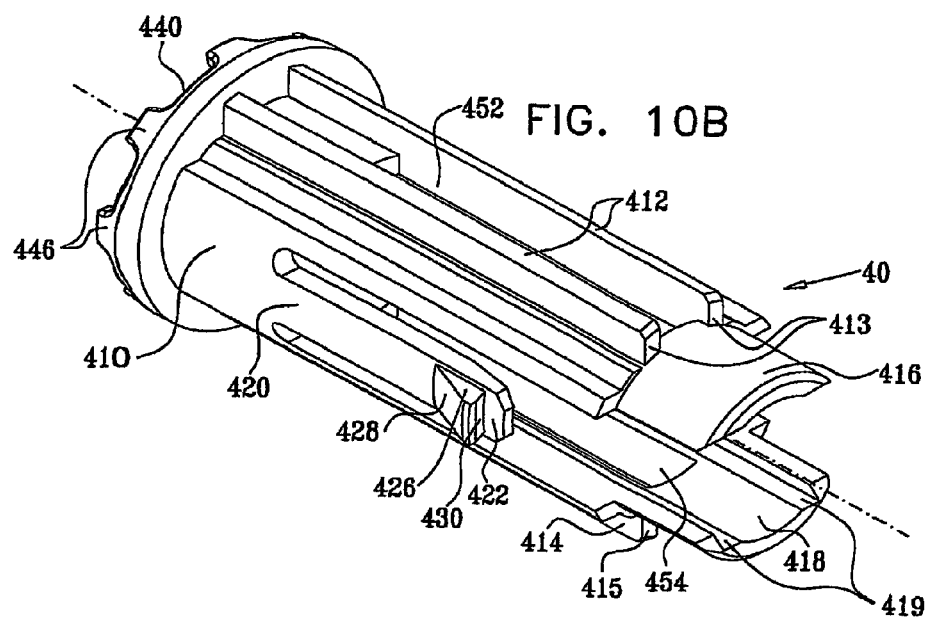
Figure 11A:
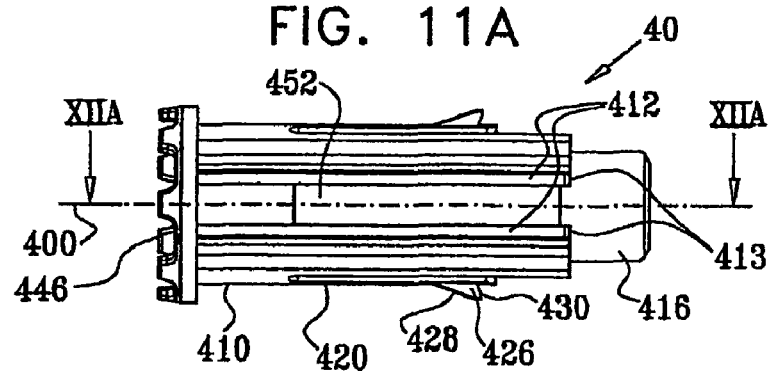
FIGS. 11A and 11B are respective top and side view simplified planar illustrations of the needle guard element of FIGS. 10A and 10B.
Figure 11B:
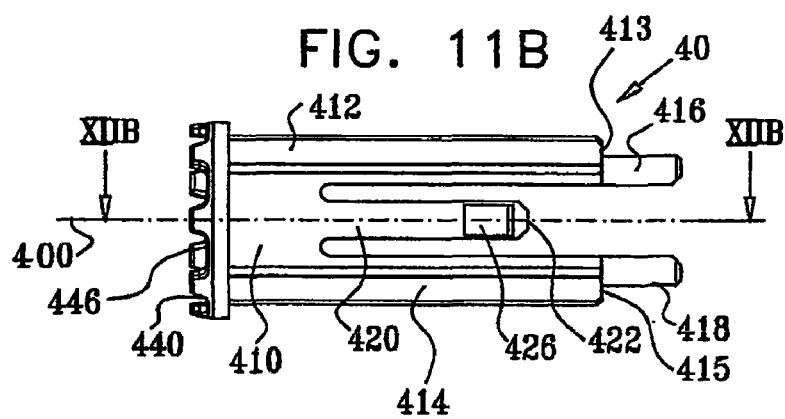
Figure 12A:
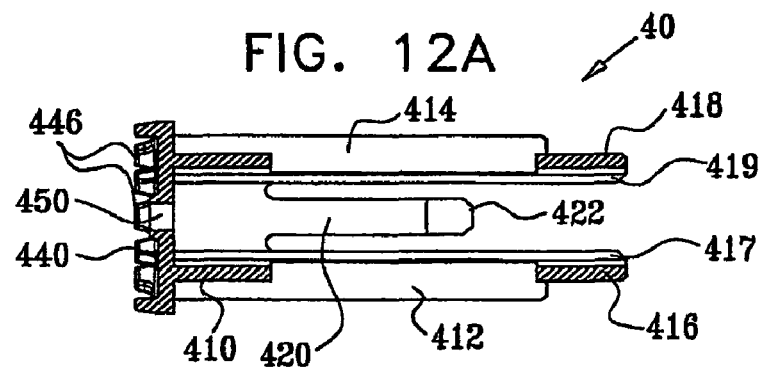
FIGS. 12A and 12B are sectional illustrations taken along respective section lines and directions XIIA-XIIA and XIIB-XIIB in FIGS. 11A and 11B.
Figure 12B:
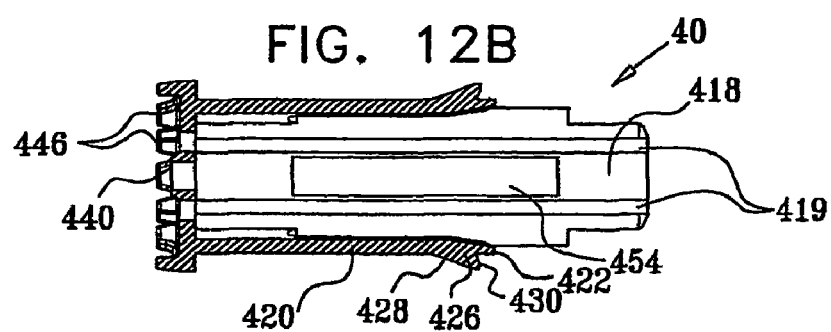
Figure 13A:
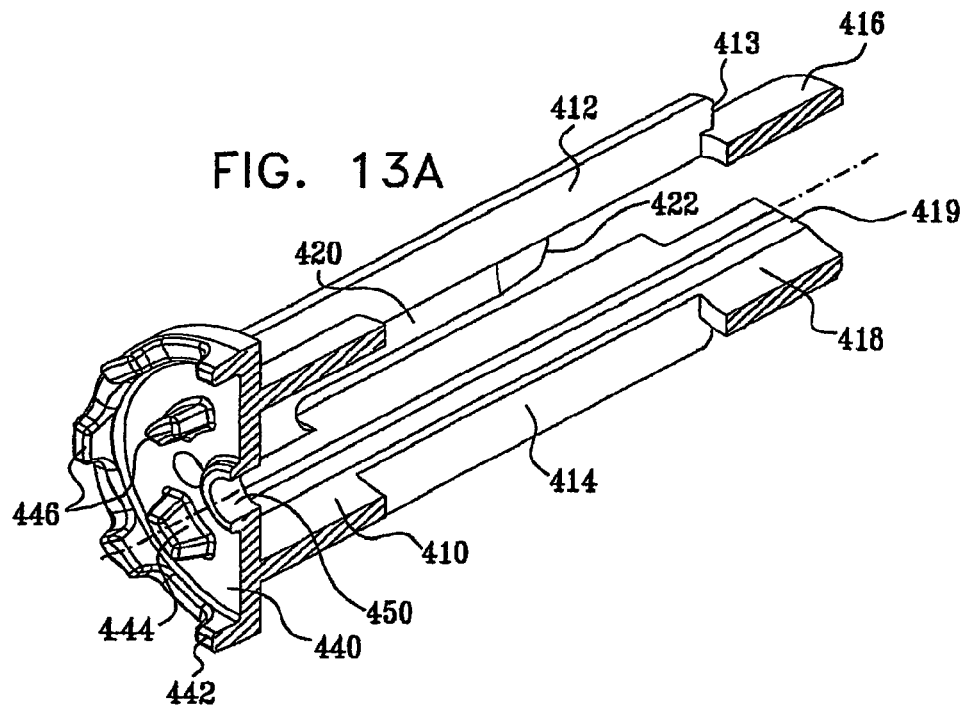
FIGS. 13A and 13B are pictorial sectional illustrations taken along respective section lines and directions XIIIA-XIIIA and XIIIB-XIIIB in FIG. 10A.
Figure 13B:
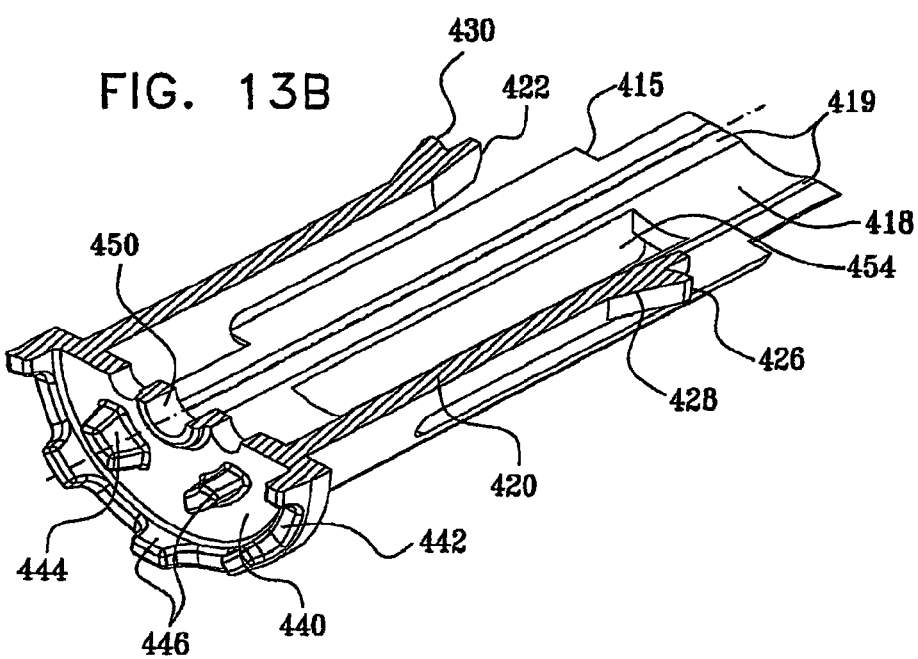

Reference is now made to FIGS. 10A and 10B, which are simplified pictorial illustrations of a needle guard element 40 which forms part of the automatic needle device of FIG. 1, to FIGS. 11A and 11B, which are respective top and side view simplified planar illustrations of the needle guard element of FIGS. 10A and 10B, to FIGS. 12A and 12B, which are sectional illustrations taken along respective section lines and directions XIIA-XIIA and XIIB-XIIB in FIGS. 11A and 11B and to FIGS. 13A and 13B which are pictorial sectional illustrations taken along respective section lines and directions XIIIA-XIIIA and XIIIB-XIIIB in FIG. 10A.

As seen in FIGS. 10A-13B, the needle guard element 40 preferably is an integrally formed element, preferably injection molded of plastic. Needle guard 40 preferably has a generally cylindrical configuration and is preferably top-to-bottom and side-to-side symmetric about a longitudinal axis 400, which, when assembled together with housing element 10 and needle hub assembly 30 is coaxial with longitudinal axis 100 (FIGS. 2A-5B) and longitudinal axis 300 (FIGS. 6A-9B).

Needle guard element 40 preferably defines a generally tubular body 410. Four mutually circumferentially spaced, longitudinally extending, outward facing ribs 412 and 414, having rearward facing ends 413 and 415 respectively, are formed on both the top and the bottom of generally tubular body 410. Outward facing ribs 412 and 414 are adapted to slidably locate the needle guard element 40 within the inwardly extending longitudinal slots 130 of the housing element 10. Extending rearwardly of ribs 412 is a curved rearward facing portion 416 having a pair of ribs 417 formed therein, and extending rearwardly of ribs 414 is a similar and symmetrically curved rearward facing portion 418 having a pair of ribs 419 formed therein.

Curved rearward facing portions 416 and 418 together with rearward facing ends 413 and 415 define the seat for spring 22. Ribs 417 and 419 are operative to slidably locate needle hub assembly 30 within needle guard element 40, by allowing outwardly facing ribs 332 and 334 to slide therein. A rearwardly extending arm 420 is formed at each side of tubular body 410. Each arm includes adjacent an extreme rearwardly facing end 422 thereof, an outwardly facing tooth 426, having an inclined forward surface 428 and a transversely extending rearwardly facing surface 430.

Tubular body 410 defines a generally open back and a forward facing wall portion 440, defining an injection site engagement surface characterized in that it has a pair of mutually concentric circles 442 and 444 of mutually spaced forwardly extending protrusions 446. Forward facing wall portion 440 is formed with an axial bore 450, arranged to allow needle 34 to extend therethrough.

Top and bottom windows 452 and 454 are defined between respective pairs of ribs 412 and 414.

The needle guard element 40 may optionally be formed with a pair of side-to-side symmetric windows, to allow viewing of the tip of the needle 34, for example when purging air bubbles from syringe 50. Alternatively, needle guard element 40 may be formed of a transparent material.

Figure 14A:
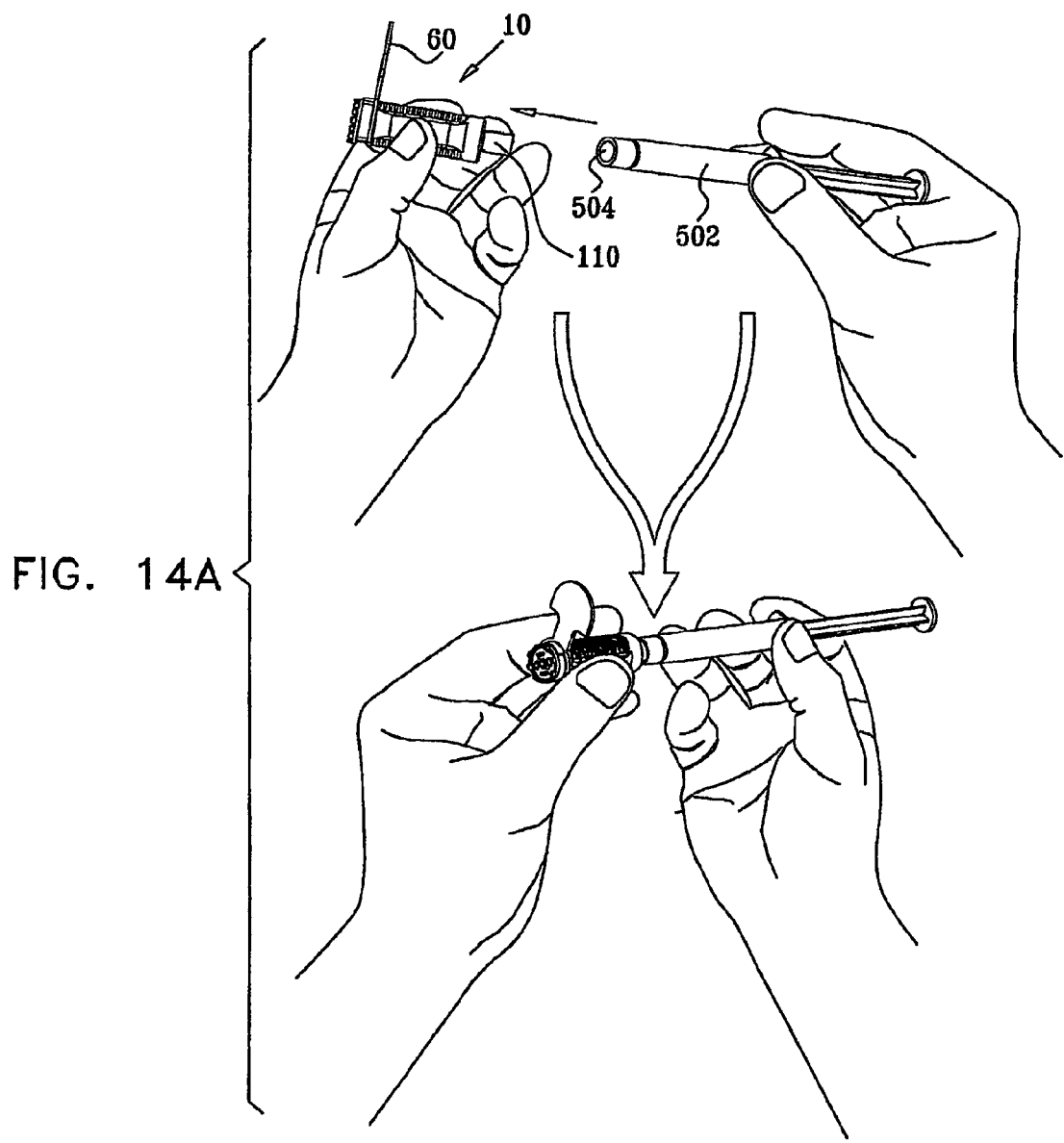
FIGS. 14A, 14B, 14C and 14D are simplified pictorial illustration of typical use of the automatic needle device of FIG. 1.

Reference is now made to FIGS. 14A, 14B, 14C and 14D which when taken together form a simplified pictorial illustration of various stages of typical use of the automatic needle device of FIG. 1. As seen in FIG. 14A the automatic needle device of FIG. 1 is stored prior to use in a pre-use operative orientation, described hereinbelow with reference to FIGS. 15-17B. When ready for use, the user attaches a syringe 502, containing a drug and ready for injection, to the automatic needle device of FIG. 1, by inserting a forward end 504 of the syringe 502 into generally tubular portion 110 of housing element 10.

Figure 14B:
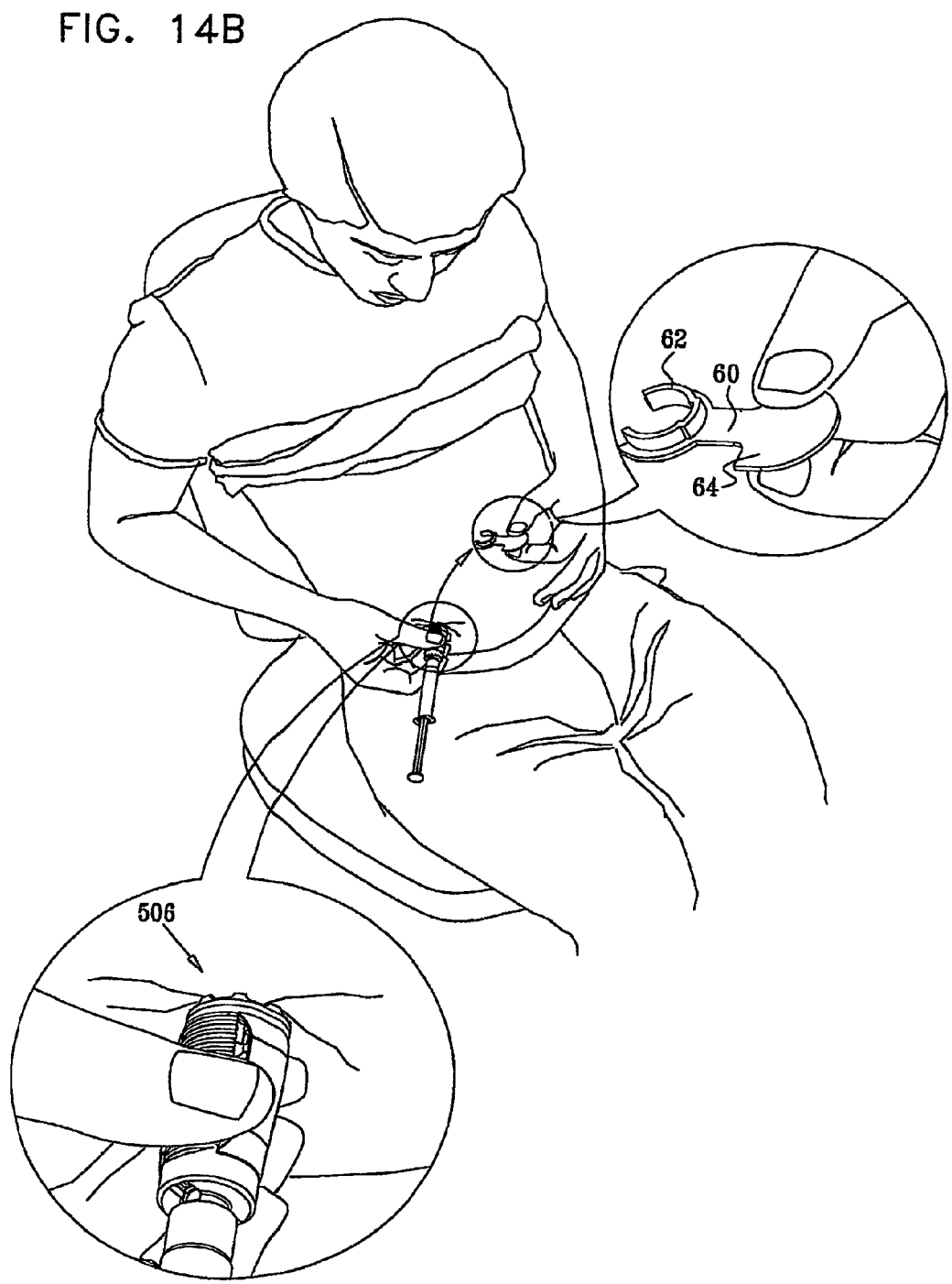

As shown in FIG. 14B, the user may then pull on tab portion 64 of safety tab 60 (FIG. 1), thereby disengaging the tubular portion 62 from the automatic needle device and allowing activation of the automatic needle device.

Figure 14C:
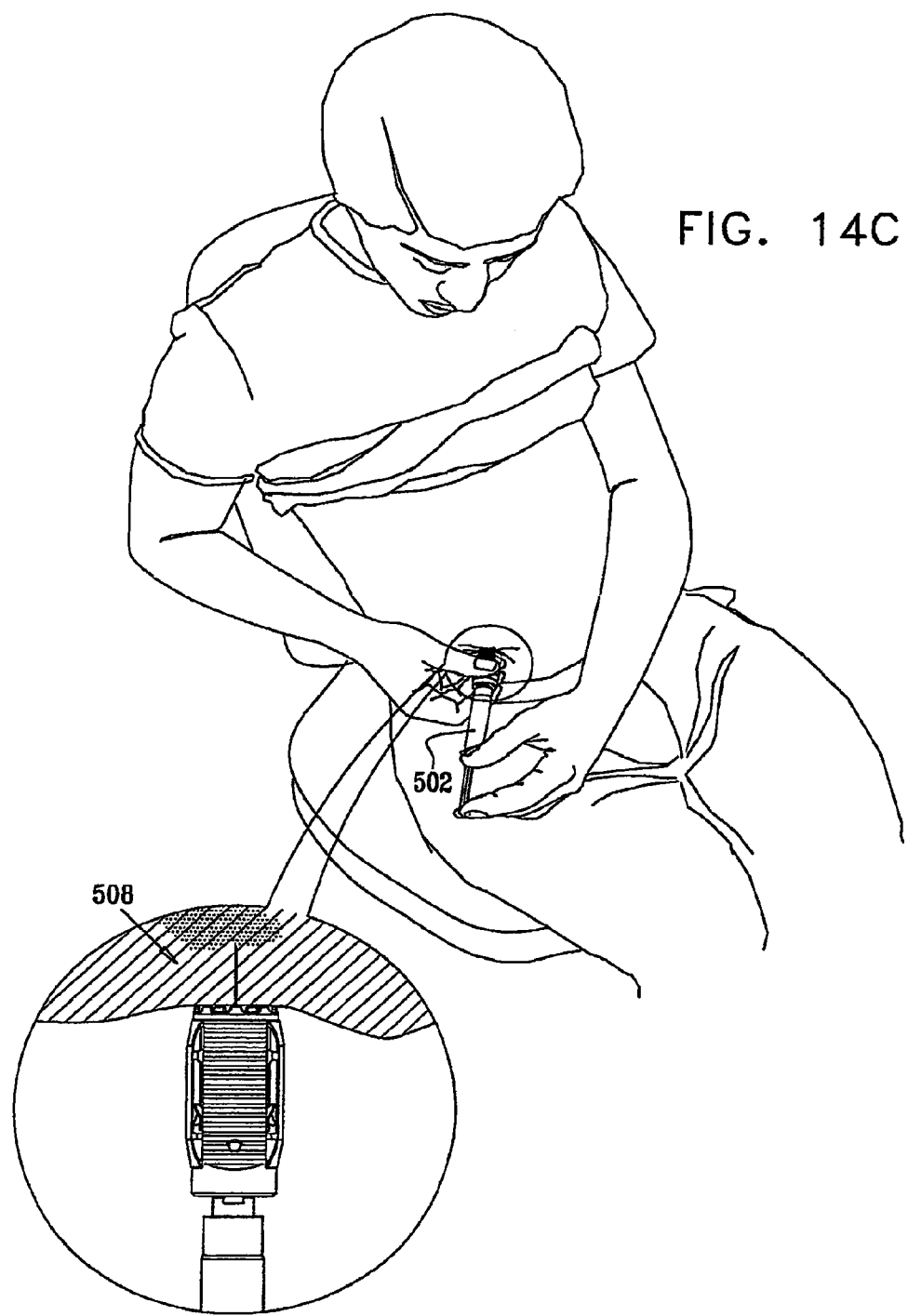

The user may subsequently actuate the automatic needle device by pushing it against an injection site as indicated in FIG. 14B and as described hereinbelow with reference to FIGS. 18-20B. In response to user actuation, automatic needle penetration takes place at the injection site, as indicated in FIG. 14C. Immediately thereafter drug delivery takes place, by user depression of a plunger in syringe 502. The operative orientation of the automatic needle device at this stage is described hereinbelow with reference to FIGS. 21-23B.

Figure 14D:
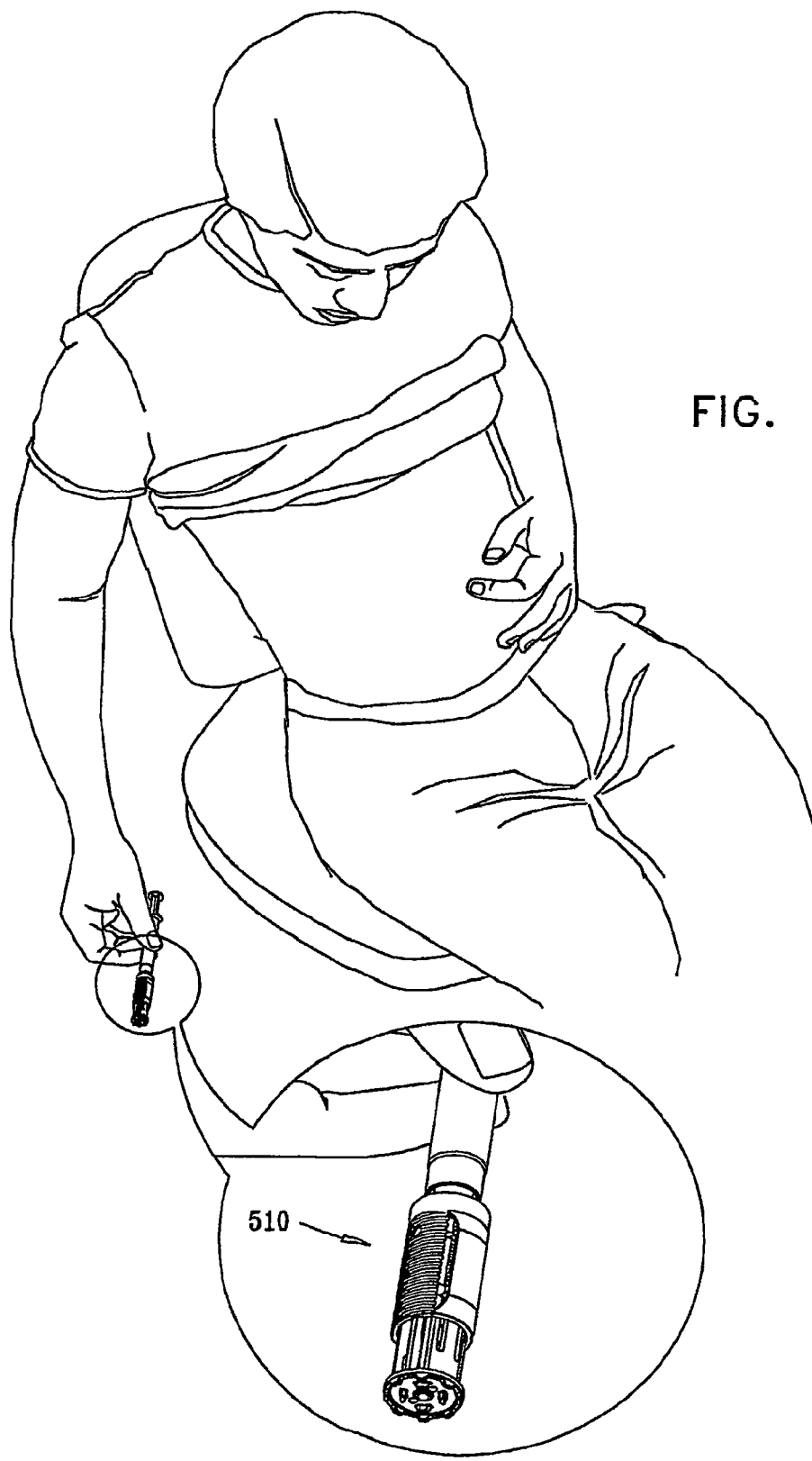

The operative orientation of the automatic needle device immediately following completion of drug delivery and disengagement of the automatic needle from the injection site is indicated in FIG. 14D and is described hereinbelow with reference to FIGS. 24-26B.

Figure 16A:
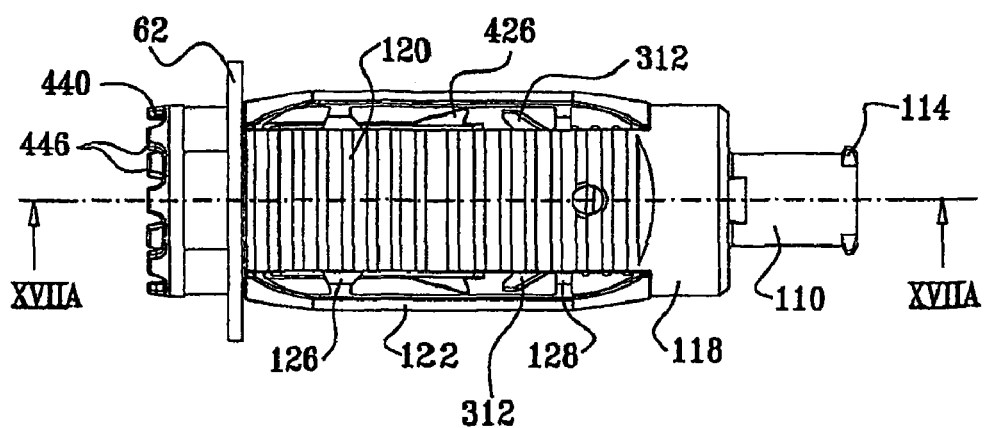
FIGS. 16A and 16B are respective top and side view simplified planar illustrations of the automatic needle device of FIGS. 15A and 15B.
Figure 16B:
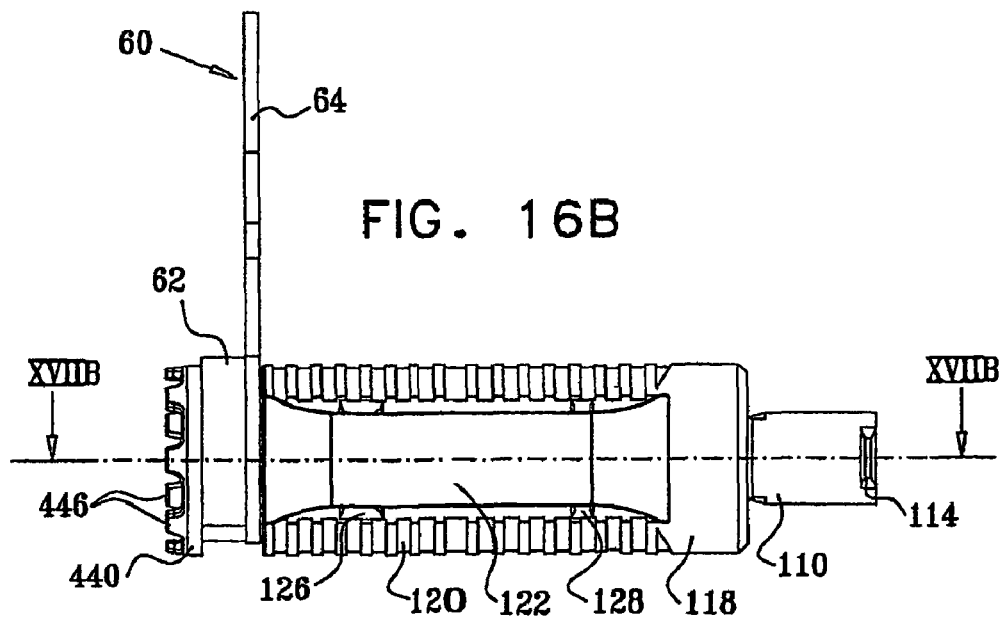

Reference is now made to FIGS. 15A and 15B, which are simplified assembled view illustrations of the automatic needle device of FIGS. 1 and 14A in a pre-use operative orientation, to FIGS. 16A and 16B, which are respective top and side view simplified planar illustrations thereof and to FIGS. 17A and 17B, which are sectional illustrations taken along respective section lines and directions XVIIA-XVIIA and XVIIB-XVIIB in FIGS. 16A and 16B.

As seen in FIGS. 15-17B, in a pre-use operative orientation of the automatic needle device, suitable for storage, the housing element 10 is joined to the needle hub assembly 30 by engagement of inner facing teeth 324 into apertures 144 formed in the cylindrical walls of bore 136. First and second compression springs 20 and 22 are located mutually coaxially within housing element 10.

Compression spring 20 is maintained under compression between forward-facing back wall surface 155 of generally cylindrical portion 118 of housing element 10 and rearward facing wall portion 350 of hub assembly 30.

Compression spring 22 is maintained under compression between forward facing back wall surface 154 and rearward facing ends 413 and 415 of needle guard element 40, which is slidably retained against forward movement by the positioning of curved rearward facing portions 416 and 418 thereof immediately rearward of teeth 326 of needle hub assembly 30.

The needle hub assembly 30 is retained in place by engagement of outwardly facing surfaces of inner facing teeth 324 of rearwardly extending arms 320 and curved rearward facing portions 416 and 418 of needle guard element 40. This prevents rearwardly extending arms 320 of needle hub assembly 30 from bending outwardly and releasing the engagement of inner facing teeth 324 and apertures 144 formed in the cylindrical walls of bore 136 of the housing 10. The tubular portion 62 of safety tab 60 prevents the needle guard element 40 from moving backwards and allowing needle penetration.

Reference is now made to FIG. 18, which is a simplified pictorial illustration of the automatic needle device of FIGS. 1 and 14B after coupling to a syringe 502 in an injection site engagement operative orientation, to FIGS. 19A and 19B, which are respective top and side view simplified planar illustrations thereof and to FIGS. 20A and 20B, which are sectional illustrations taken along respective section lines and directions XXA-XXA and XXB-XXB in FIGS. 19A and 19B.

As seen particularly in FIG. 20A, due to engagement of the needle guard element 40 with an injection site on a body, the needle guard 40 is forced, against the urging of spring 22, to move axially in a rearward direction with respect to the remainder of the automatic needle device, thus sliding curved rearward facing portions 416 and 418 thereof further rearward of teeth 326 of needle hub assembly 30.

This rearward repositioning of curved rearward facing portions 416 and 418 and the pressure of spring 20, allow arms 320 of needle hub assembly 30 to cantilever outwardly.

Reference is now made to FIG. 21, which is a simplified pictorial illustration of the automatic needle device of FIGS. 1 and 14C in an actuated operative orientation, to FIGS. 22A and 22B which are respective top and side view simplified planar illustrations thereof and to FIGS. 23A and 23B which are sectional illustrations taken along respective section lines and directions XXIIIA-XXIIIA and XXIIIB-XXIIIB in FIGS. 22A and 22B.

As seen particularly in FIG. 23A, under the urging of spring 20, inner facing teeth 324 slide out of apertures 144 formed in the cylindrical walls of bore 136, thus allowing the needle hub assembly 30 to move axially forward and to provide needle penetration. The forward motion of needle hub assembly 30 stops when protrusions 312 and 314 come into touching engagement with inwardly extending transverse ribs 126 of the housing 10. At this stage, drug delivery may take place in response to manual operation of syringe 502

It is appreciated that at all times needle 34 sealingly and slidably engages septum 36.

Figure 24:
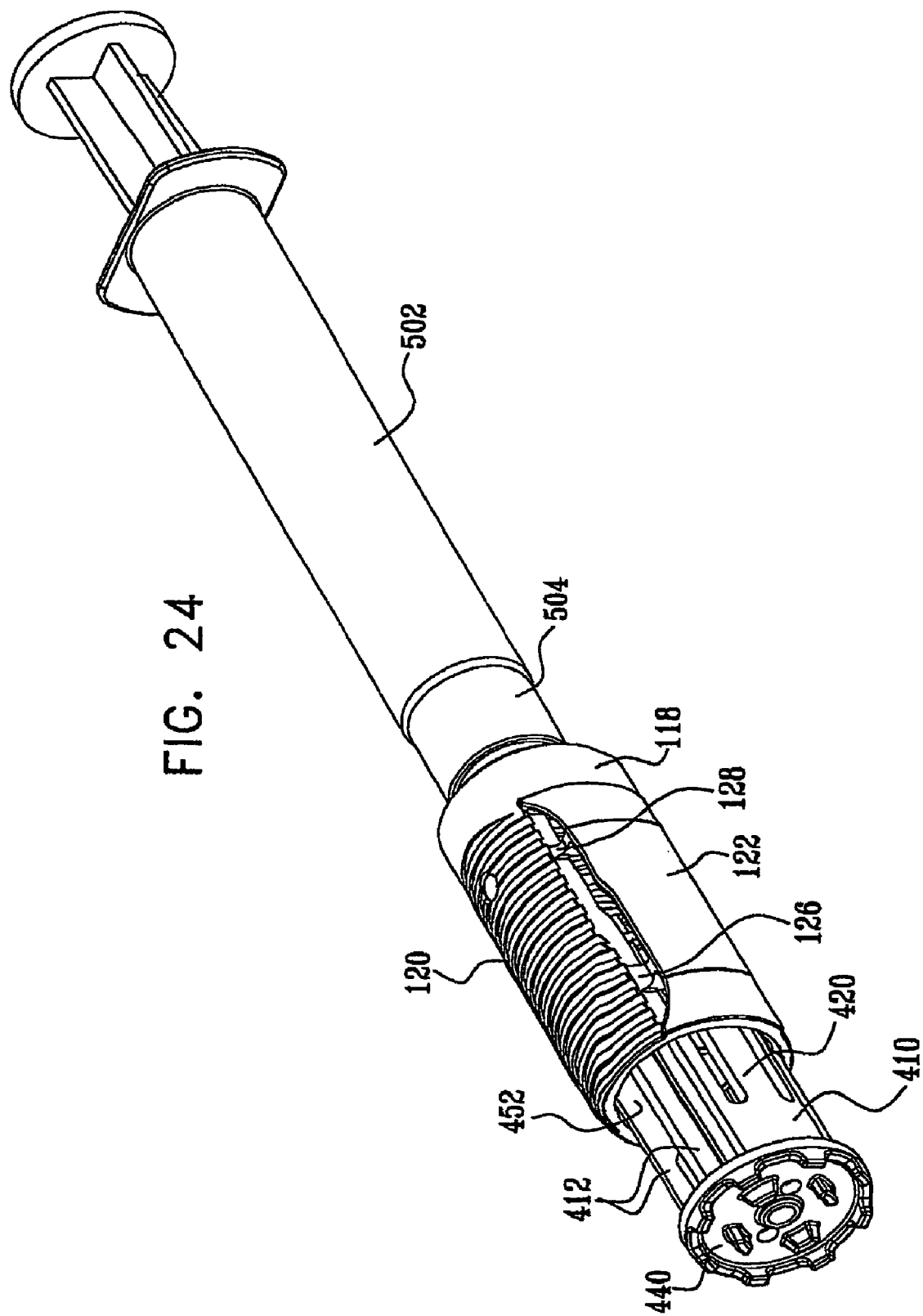
FIG. 24 is a simplified pictorial illustration of the automatic needle device of FIGS. 1 and 14D in a post-drug delivery, needle guarded operative orientation.

Reference is now made to FIG. 24, which is a simplified pictorial illustration of the automatic needle device of FIGS. 1 and 14D in a post-drug delivery, needle guarded operative orientation, to FIGS. 25A and 25B, which are respective top and side view simplified planar illustrations thereof and to FIGS. 26A and 26B, which are sectional illustrations taken along respective section lines and directions XXVIA-XXVIA and XXVIB-XXVIB in FIGS. 25A and 25B.

FIGS. 24-26B illustrate the automatic needle device fully disengaged from the injection site and the needle guard 40 is fully extended under the urging of spring 22 to fully enclose the needle 34. The needle guard 40 is prevented from moving farther forwards by engagement of curved rearward facing portions 416 and 418 and rearwardly extending surface 330 of teeth 326 of needle hub assembly 30. The needle hub assembly 30 is prevented from moving further forward by protrusions 312 and 314 leaning against inwardly extending transverse ribs 126 of the housing 10. The needle guard 40 is prevented from moving rearwardly by outwardly facing tooth 426, which fits in front of inwardly extending transverse ribs 126 of the housing 10. Therefore, at this stage the needle guard 40 is locked in place, protecting keeping the needle 34 from inadvertent engagement.

It is appreciated that the automatic needle device can be attached to various types of injection devices, and that the a luer adapter defined by an internal tapered surface of the tubular portion 110 of the housing element 10 of the automatic needle device may be readily modified for engagement with various injection devices such as pen injectors. It is also possible to integrate the automatic needle apparatus described herein into another injection device and thus to eliminate the need for a luer adapter.

Reference is now made to FIGS. 27-43C, which illustrate the constituent elements of an automatic needle device constructed and operative in accordance with another preferred embodiment of the present invention.

As seen with particular clarity in FIG. 27, the automatic needle device comprises a housing element 810, having an integrally formed safety tab 812, including a tab portion 814 and a spacer portion 816, a resilient element 820, which provides selectable forward displacement to a needle hub assembly 830, which includes a hub portion 832 and a needle 834 adhesively or otherwise adhered thereto and extending rearwardly through a septum portion of resilient element 820, and to a needle guard element 840.

It is appreciated that safety tab 812 can be a separate part formed of any suitable material, for example such as polypropylene, and may formed in various configurations, such as a portion which is inserted into a slot between the needle guard element 840 and the housing element 810, as a stand alone injection molded part, or as an integral part of any of the parts of the automatic needle device such as the housing element 810, the needle guard element 840 or the needle hub 832.

It will additionally be appreciated by those skilled in the art that resilient element 820 may be replaced with compression springs as described hereinabove with reference to FIGS. 1-26B. Alternatively, compression springs 20 and 22 may be replaced by tension springs, elastomeric compression springs or plastic springs which are preferably integrated into housing element 810, into needle hub assembly 830 or into needle guard element 840.

Figure 28A:
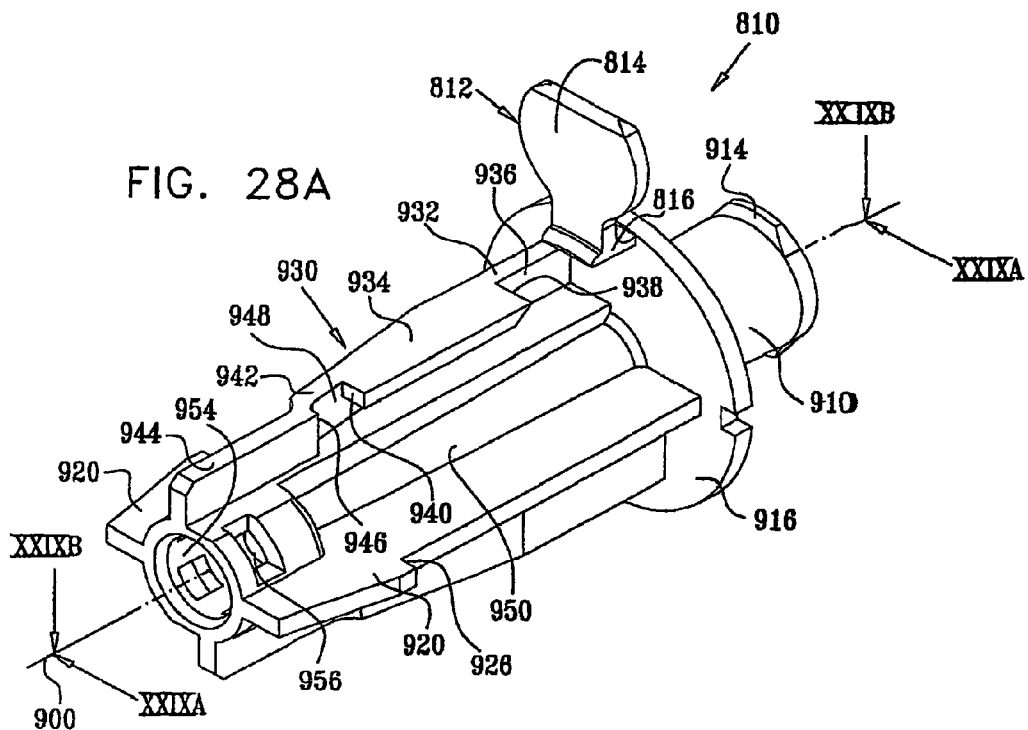
FIGS. 28A and 28B are simplified pictorial illustrations of a housing element which forms part of the automatic needle device of FIG. 27.
Figure 28B:
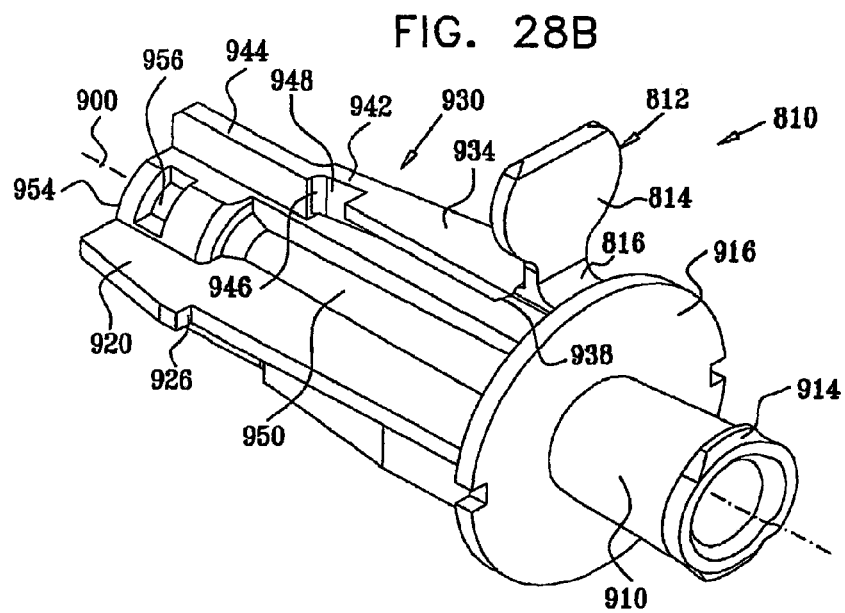
Figure 29A:
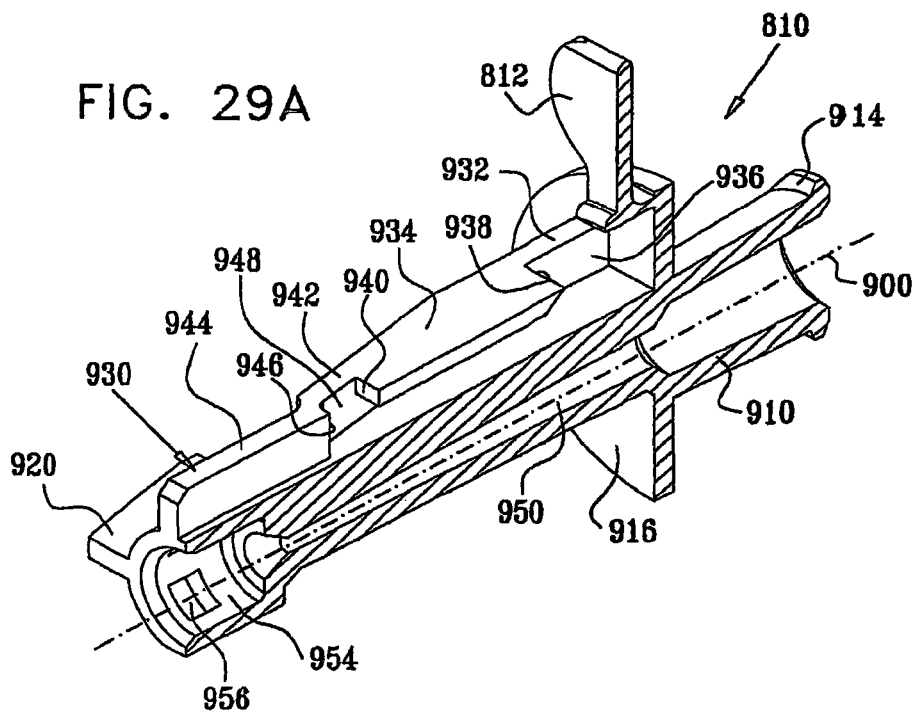
FIGS. 29A and 29B are simplified pictorial sectional illustrations of the housing element of FIGS. 28A and 28B taken along lines XXIXA-XXIXA and XXIXB-XXIXB in FIG. 28A.
Figure 29B:
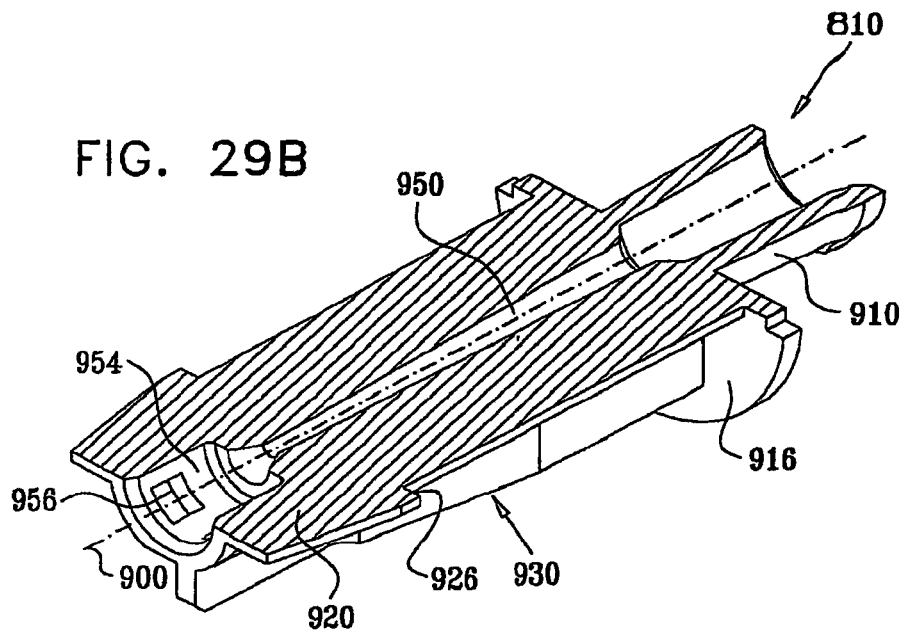
Figure 30A:
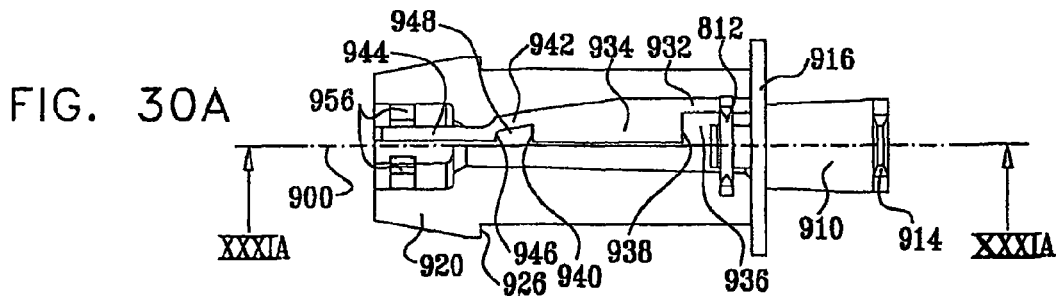
FIGS. 30A and 30B are respective top and side view simplified planar illustrations of the housing element of FIGS. 28A-29B.
Figure 30B:
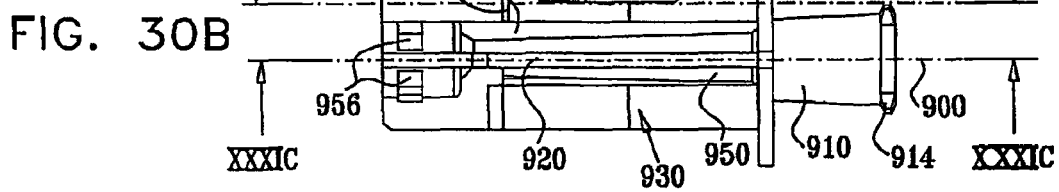
Figure 31A:
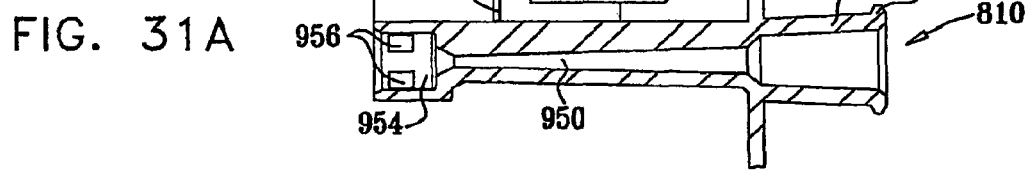
FIGS. 31A, 31B and 31C are sectional illustrations taken along respective section lines and directions XXXIA-XXXIA, XXXIB-XXXIB and XXXIC-XXXIC in FIGS. 30A and 30B.
Figure 31B:
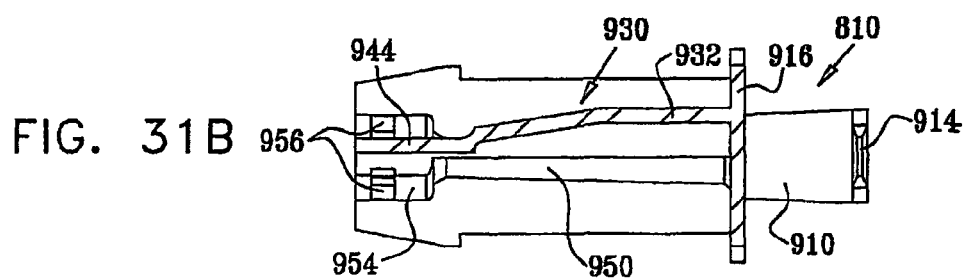
Figure 31C:
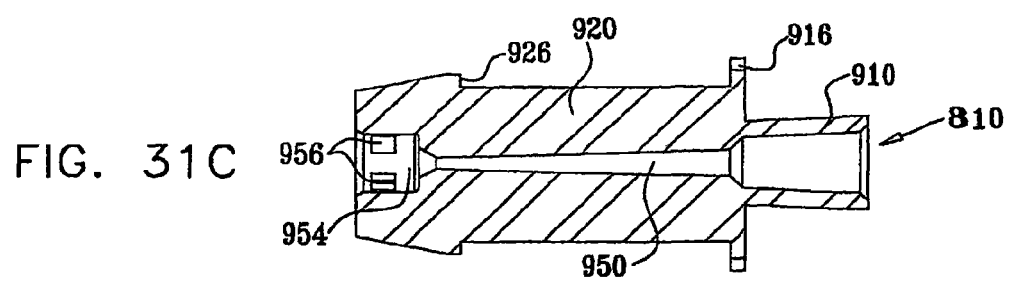

Reference is now made to FIGS. 28A and 28B, which are simplified pictorial illustrations of a preferred housing element 810 which forms part of the automatic needle device of FIG. 27, to FIGS. 29A and 29B which are simplified pictorial sectional illustrations of the housing element of FIGS. 28A and 28B taken along lines XXIXA-XXIXA and XXIXB-XXIXB in FIG. 28A, to FIGS. 30A and 30B which are respective top and side view simplified planar illustrations thereof and to FIGS. 31A, 31B and 31C which are sectional illustrations taken along respective section lines and directions XXXIA-XXXIA, XXXIB-XXXIB and XXXIC-XXXIC in FIGS. 30A and 30B.

As seen in FIGS. 28A-31C, the housing element 810 preferably is an integrally formed element, preferably injection molded of plastic. Housing element 810 preferably has a generally cylindrical configuration and is preferably side-to-side symmetric about a longitudinal axis 900.

Housing element 810 preferably includes a rearward generally tubular portion 910, which terminates in an open back and defines generally symmetric side-facing tabs 914. Forward of rearward generally tubular portion 910 there is provided a flange 916 onto which is removably mounted safety tab 812 (FIG. 27) which, as will be described hereinbelow, when intact, prevents the needle guard 840 from rearward displacement into engagement with flange 916.

Forward of flange 916 there are provided a pair of side-to-side symmetric generally axially directed, radially extending ribs 920, each of which is formed with a rearward facing shoulder 926. Also extending forwardly of flange 916 there is provided a generally axially directed rib 930, which includes a narrow, generally axially directed, radially extending portion 932 forward of which a generally planar portion 934 is formed generally perpendicular to an underlying generally radially extending portion 936. The generally planar portion 934 includes a radially inwardly tapered rearward facing surface 938 and a generally radial forward facing surface 940.

Forwardly of surface 940, rib 930 includes a further narrow not fully axially directed, radially extending portion 942 followed by a generally axially directed, radially extending portion 944, having a rearward facing surface 946. A socket 948 is formed between forward facing surface 940 of planar portion 934 and rearward facing surface 946 of portion 944.

Interiorly of ribs 920 and 930 there is provided a forwardly tapered passageway 950 which terminates in a generally circular septum receiving socket 954 having a plurality of circumferentially distributed apertures 956.

Figure 32A:
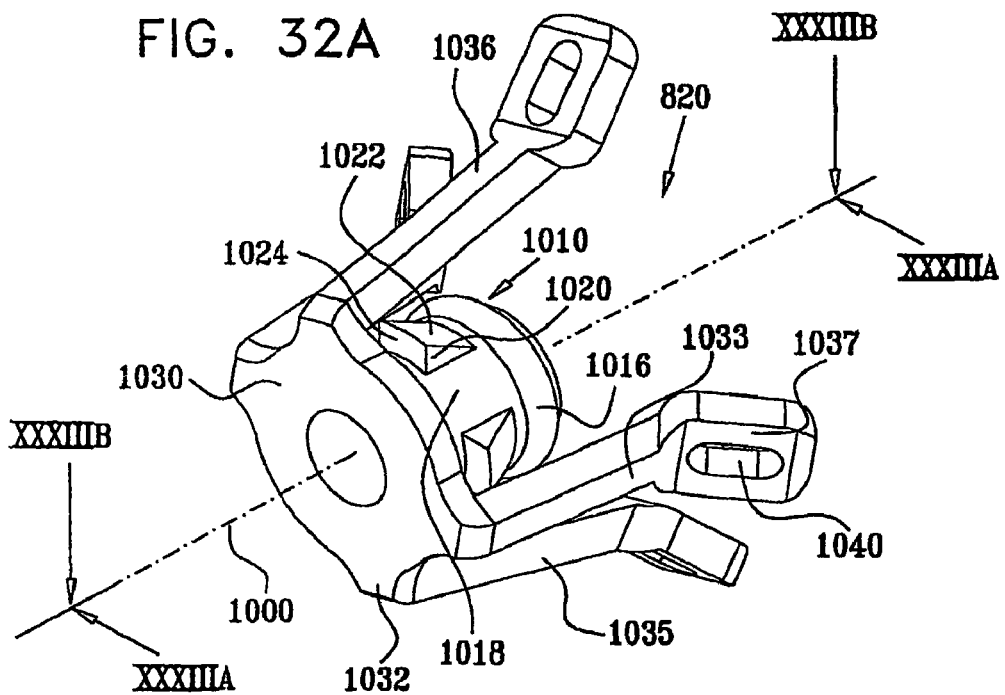
FIGS. 32A and 32B are simplified pictorial illustrations of a resilient element which forms part of the automatic needle device of FIG. 27.
Figure 32B:
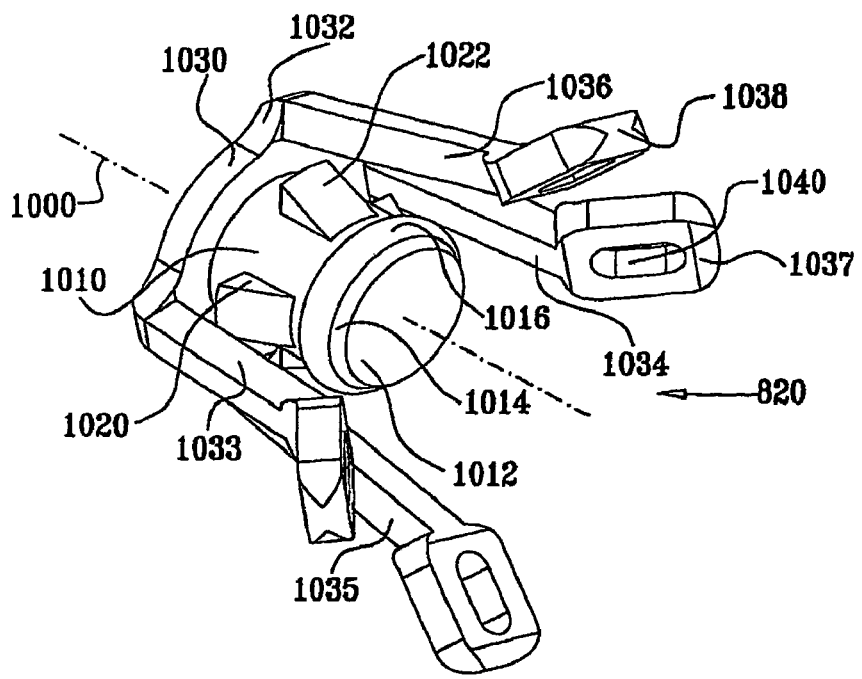
Figure 33A:
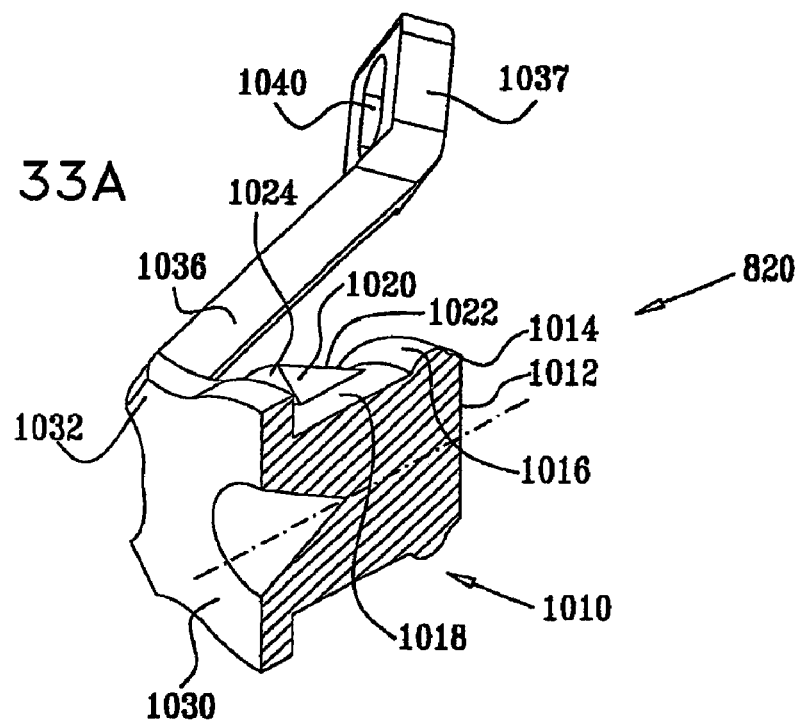
FIGS. 33A and 33B are simplified pictorial sectional illustrations of the resilient element of FIGS. 32A and 32B taken along lines XXXIIIA-XXXIIIA and XXXIIIB-XXXIIIB in FIG. 32A.
Figure 33B:
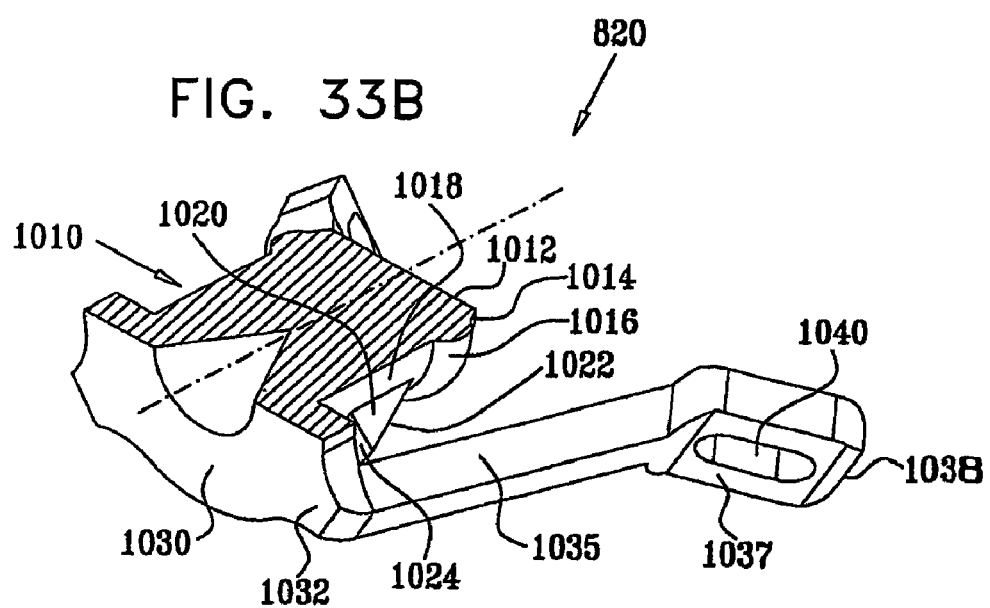
Figure 34A:
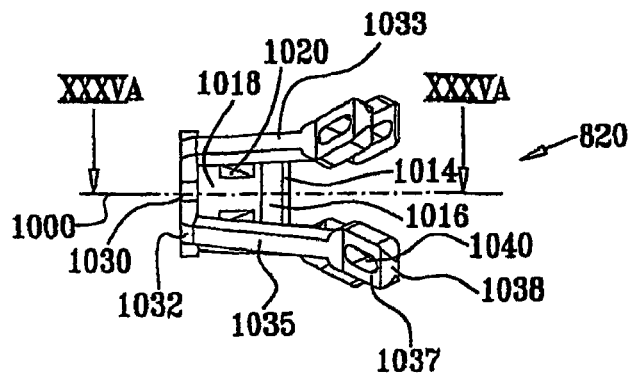
FIGS. 34A and 34B are respective top and side view simplified planar illustrations of the resilient element of FIGS. 32A-33B.
Figure 34B:
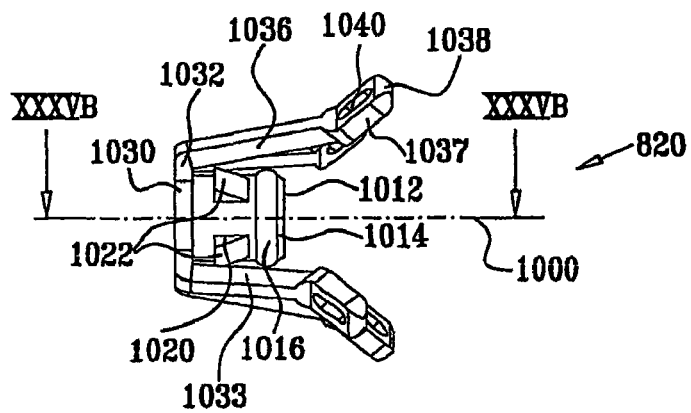
Figure 35A:
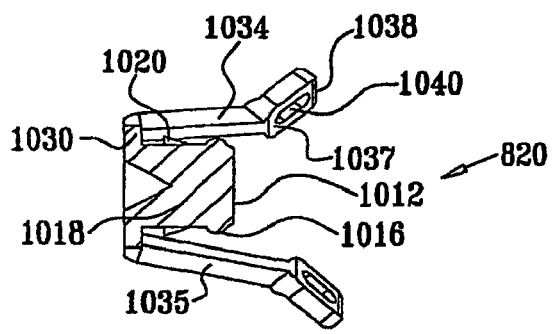
FIGS. 35A and 35B are sectional illustrations taken along respective section lines and directions XXXVA-XXXVA and XXXVB-XXXVB in FIGS. 34A and 34B.
Figure 35B:
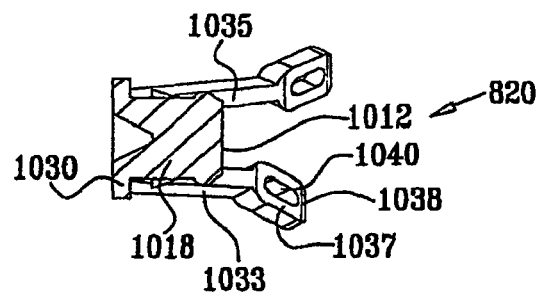

Reference is now made to FIGS. 32A and 32B, which are simplified pictorial illustrations of a resilient element which forms part of the automatic needle device of FIG. 27, to FIGS. 33A and 33B which are simplified pictorial sectional illustrations of the resilient element of FIGS. 32A and 32B taken along lines XXXIIIA-XXXIIIA and XXXIIIB-XXXIIIB in FIG. 32A, to FIGS. 34A and 34B which are respective top and side view simplified planar illustrations of the resilient element of FIGS. 32A-33B and to FIGS. 35A and 35B which are sectional illustrations taken along respective section lines and directions XXXVA-XXXVA and XXXVB-XXXVB in FIGS. 34A and 34B.

As seen in FIGS. 32A-35B, the resilient element 820 is an integrally formed element, preferably injection molded or compression molded of rubber or plastic and preferably has a generally cylindrical configuration and is preferably top-to-bottom and side-to-side symmetric about a longitudinal axis 1000, which, when assembled together with housing element 810, is coaxial with longitudinal axis 900 (FIGS. 28A-31C).

The resilient element preferably includes a generally cylindrical central portion 1010, having a rear-facing wall 1012 formed with a tapered peripheral edge 1014 followed by a peripheral protrusion 1016 having a rounded cross section. Forward of protrusion 1016 is a generally cylindrical portion 1018 having four, circumferentially distributed, radially extending teeth 1020, each of which has a forwardly radially outwardly inclined surface 1022 terminating in a forward facing surface 1024 which lies in a plane which is generally perpendicular to longitudinal axis 1000.

Forward of cylindrical portion 1018 is a forward facing flange 1030 having radially outward extending protrusions 1032 at four corners thereof, separated from each other by 90 degrees. Extending rearwardly and radially outwardly from each protrusion 1032 are tensioned arms 1033, 1034, 1035 and 1036, each of which terminates in a generally rectangular end portion 1037 having tapered outer edges 1038 and formed with a generally rectangular aperture 1040. Tensioned arms 1033 and 1034 are slightly shorter than tensioned arms 1035 and 1036.

Figure 36A:
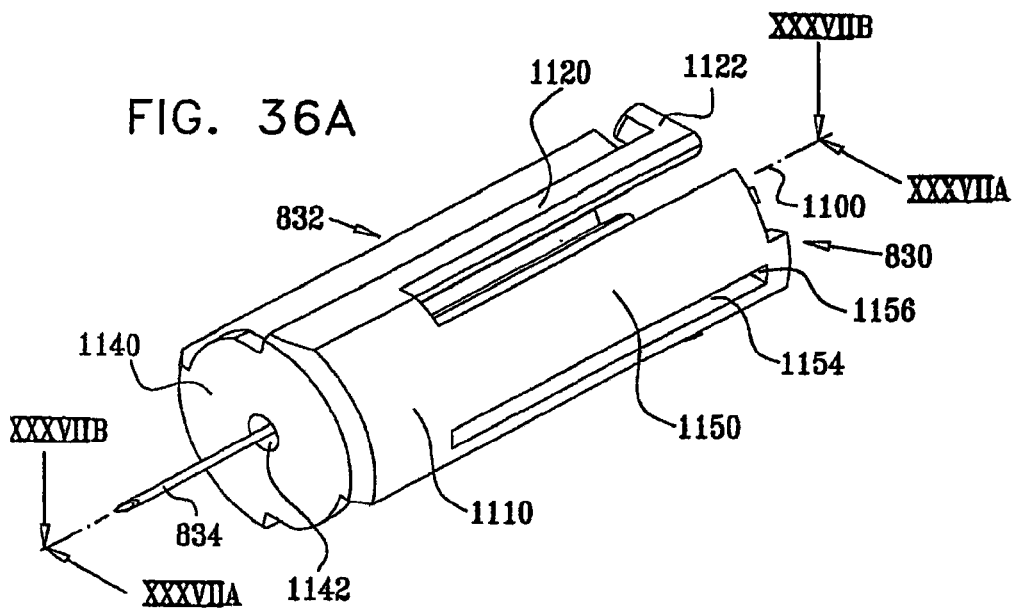
FIGS. 36A and 36B are simplified pictorial illustrations of a needle hub assembly which forms part of the automatic needle device of FIG. 27.
Figure 36B:
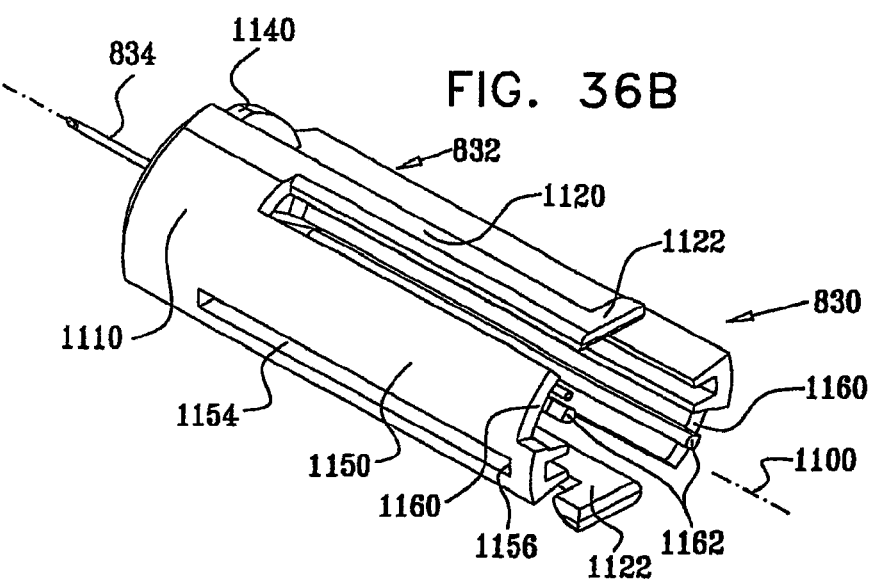
Figure 37A:
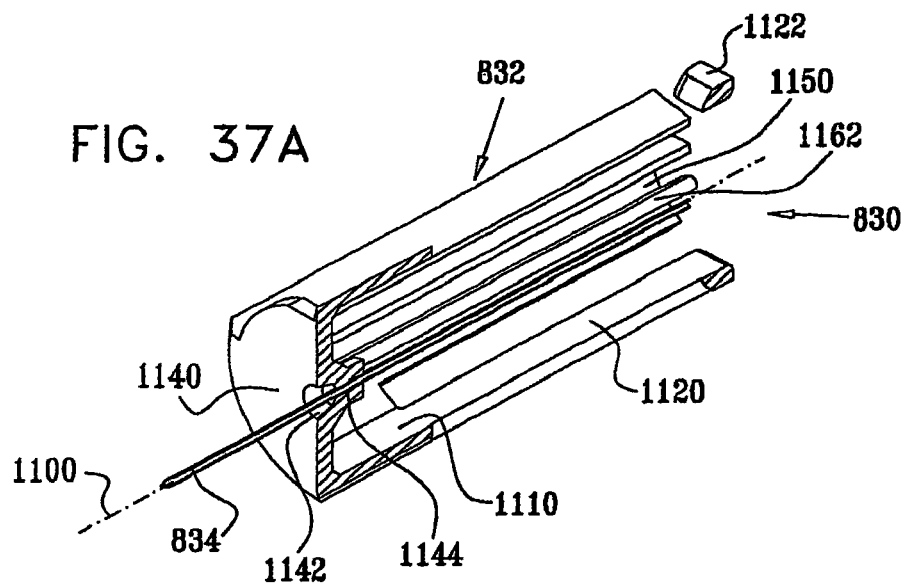
FIGS. 37A and 37B are simplified pictorial sectional illustrations of the needle hub assembly of FIGS. 36A and 36B taken along lines XXXVIIA-XXXVIIA and XXXVIIB-XXXVIIB in FIG. 36A.
Figure 37B:
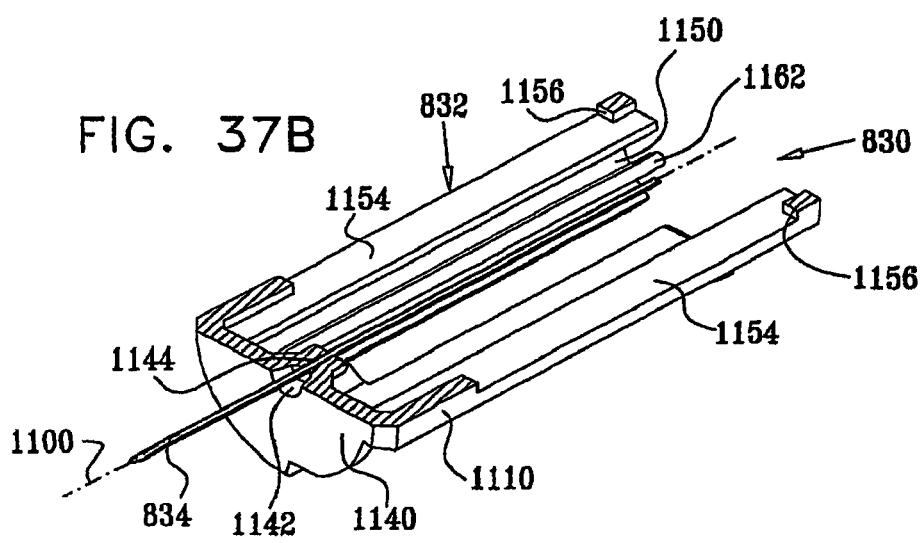
Figure 38A:
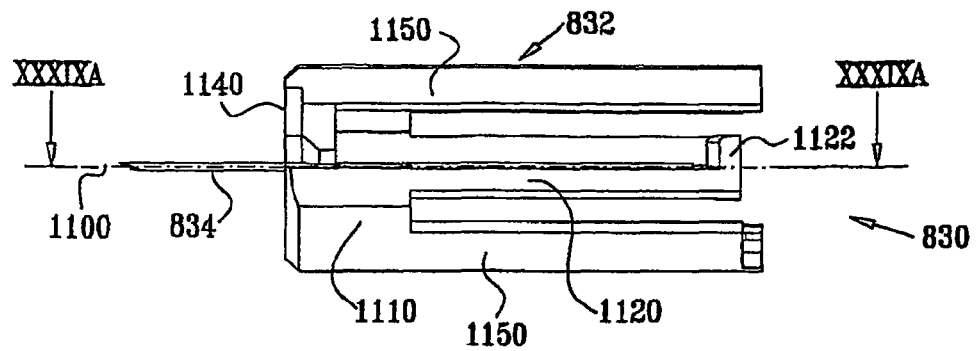
FIGS. 38A and 38B are respective top and side view simplified planar illustrations of the needle hub assembly of FIGS. 36A-37B.
Figure 38B:
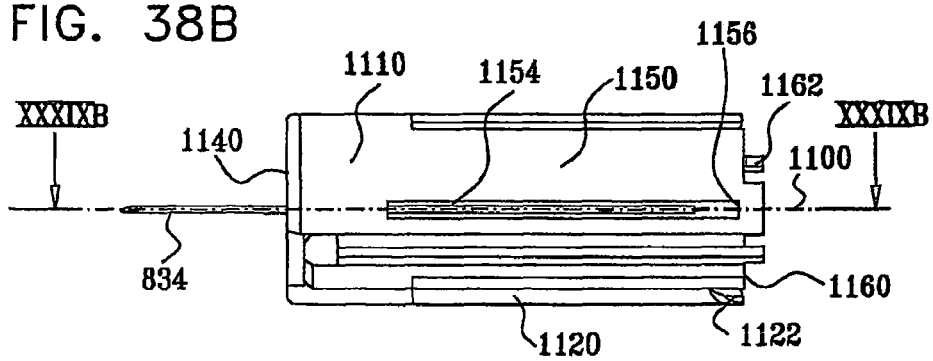
Figure 39A:
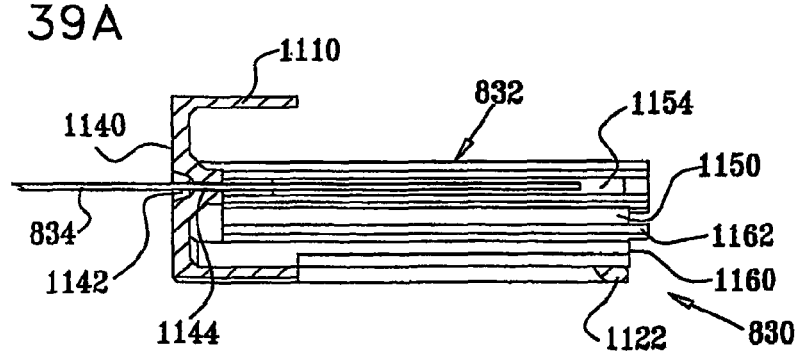
FIGS. 39A and 39B are sectional illustrations taken along respective section lines and directions XXXIXA-XXXIXA and XXXIXB-XXXIXB in FIGS. 38A and 38B.
Figure 39B:
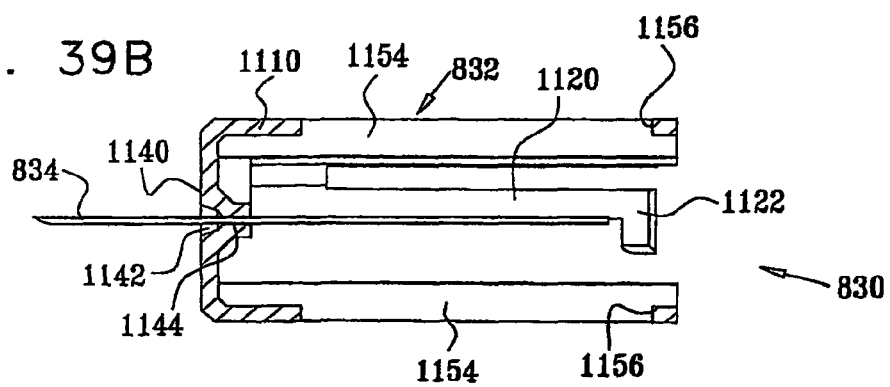

Reference is now made to FIGS. 36A and 36B, which are simplified pictorial illustrations of a needle hub assembly which forms part of the automatic needle device of FIG. 27, to FIGS. 37A and 37B which are simplified pictorial sectional illustrations of the needle hub assembly of FIGS. 36A and 36B taken along lines XXXVIIA-XXXVIIA and XXXVIIB-XXXVIIB in FIG. 36A, to FIGS. 38A and 38B which are respective top and side view simplified planar illustrations of the needle hub assembly of FIGS. 36A-37B and to FIGS. 39A and 39B are sectional illustrations taken along respective section lines and directions XXXIXA-XXXIXA and XXXIXB-XXXIXB in FIGS. 38A and 38B.

As seen in FIGS. 36A-39B, the needle hub assembly 830 preferably comprises a needle hub 832 which is an integrally formed element, preferably injection molded of plastic and a needle 834. Needle hub assembly 830 preferably has a generally cylindrical configuration and is preferably top-to-bottom and side-to-side mirror image symmetric about a longitudinal axis 1100, which, when assembled together with housing element 810, is coaxial with longitudinal axes 900 (FIGS. 28A-31C) and 1000 (FIGS. 32A-35B).

Needle hub assembly 830 preferably defines a generally tubular body 1110. A rearwardly extending arm 1120 extends axially at both the top and the bottom of tubular portion 1110 and terminates in a right angle finger 1122.

Tubular body 1110 defines a generally open back and a forward facing wall portion 1140 adjacent in which is formed a recess 1142, which communicates with a narrow axial bore 1144, arranged to receive needle 834, which extends therethrough and is held in place, preferably by an adhesive, which is located in recess 1142. Alternatively, needle hub portion 832 may be molded directly onto the needle.

A pair of arms 1150 having a cross-section in the shape of a C, extend generally axially rearwardly of tubular body 1110 and are each formed with a longitudinal slot 1154, ending in a rear surface 1156. Extending circumferentially from each arm 1150 is a wall portion 1160 at a rearward end of which extends a rearward-facing finger 1162.

Figure 40A:
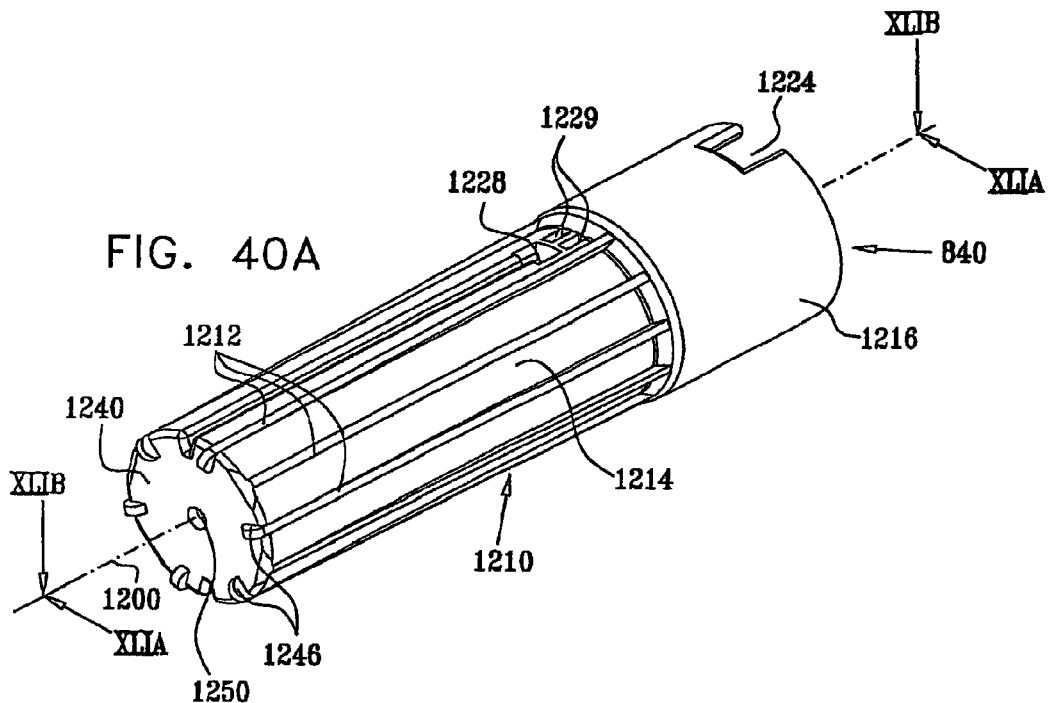
FIGS. 40A and 40B are simplified pictorial illustrations of a needle guard element which forms part of the automatic needle device of FIG. 27.
Figure 40B:
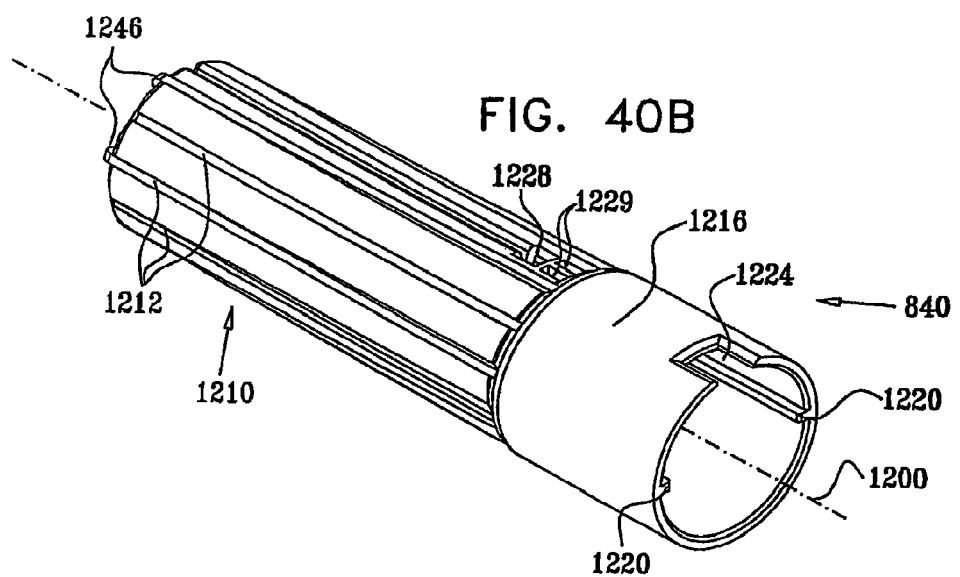
Figure 41A:
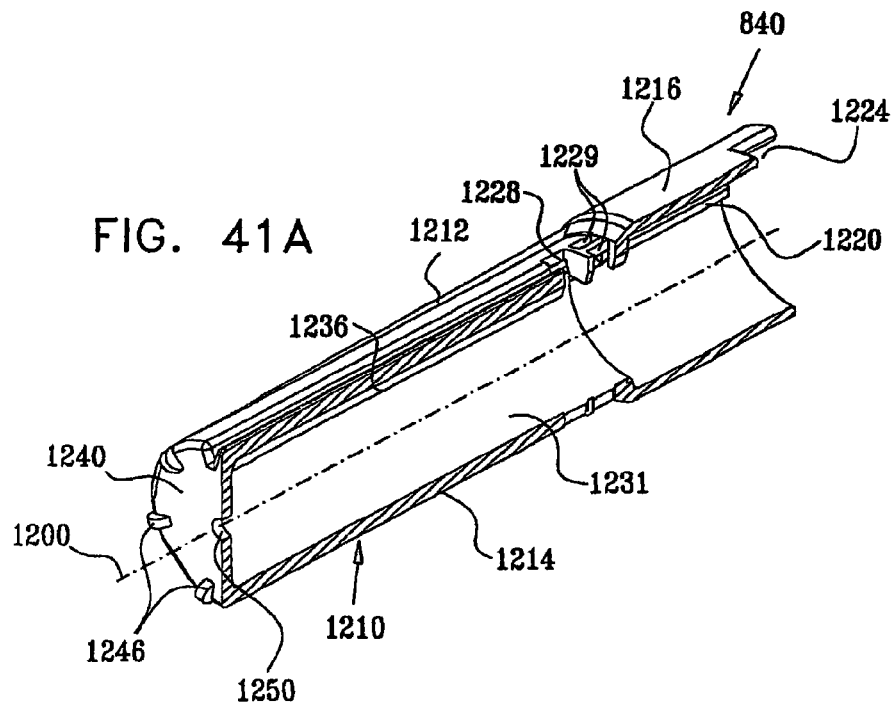
FIGS. 41A and 41B are simplified pictorial sectional illustrations of the needle guard element of FIGS. 40A and 40B taken along the lines XLIA-XLIA and XLIB-XLIB in FIG. 40A.
Figure 41B:
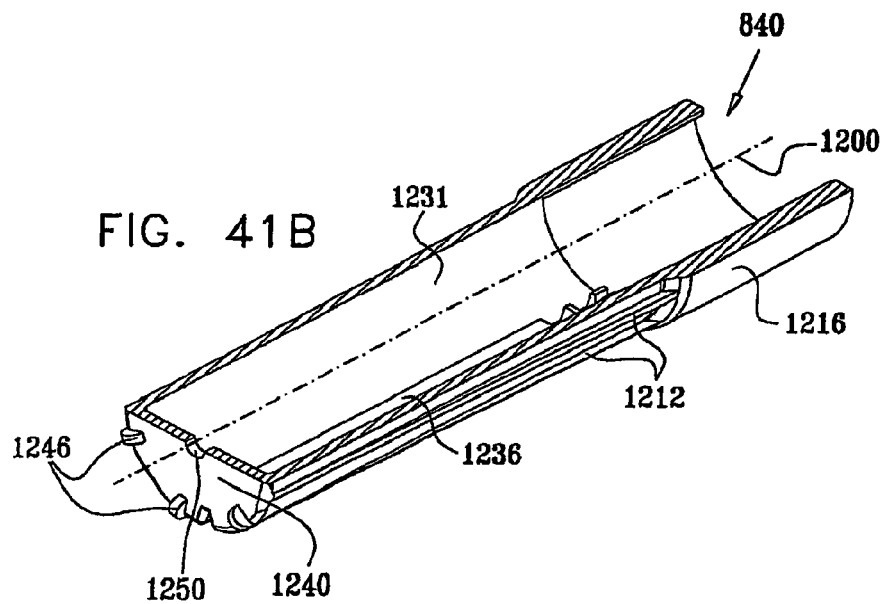
Figure 42A:
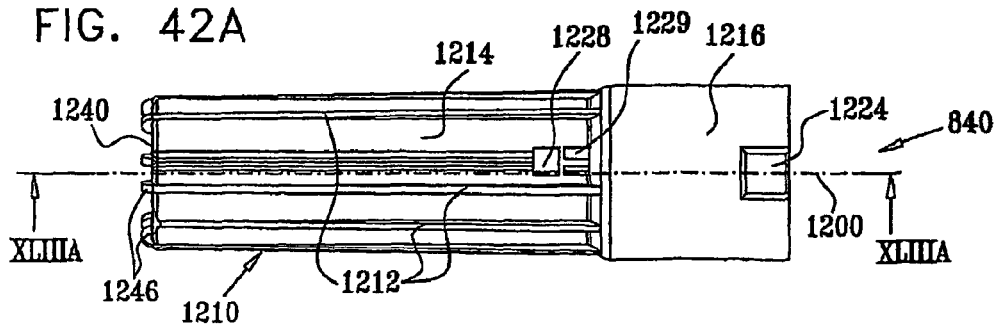
FIGS. 42A and 42B are respective top and side view simplified planar illustrations of the needle guard element of FIGS. 40A-41B.
Figure 42B:
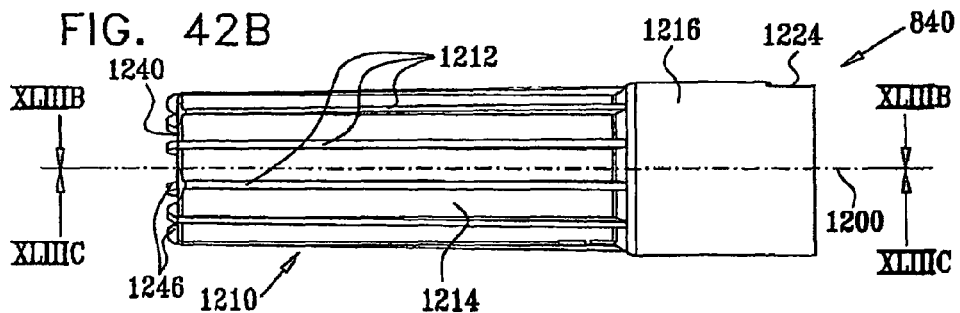
Figure 43A:
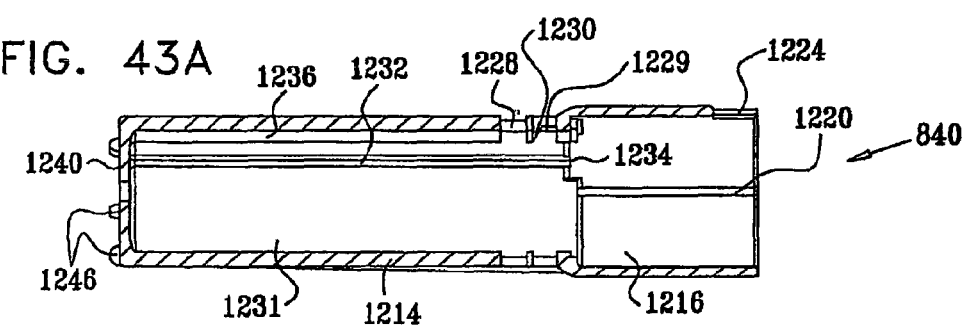
FIGS. 43A, 43B and 43C are sectional illustrations taken along respective section lines and directions XLIIIA-XLIIIA, XLIIIB-XLIIIB and XLIIIC-XLIIIC in FIGS. 42A and 42B.
Figure 43B:
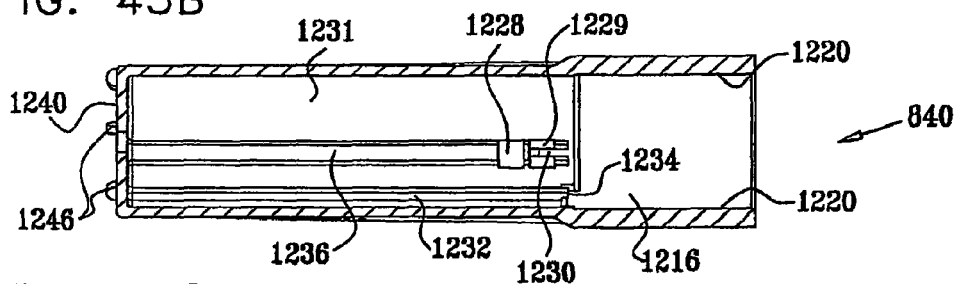
Figure 43C:
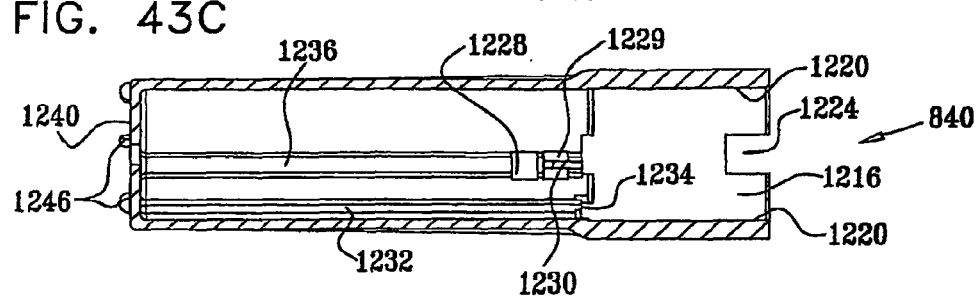

Reference is now made to FIGS. 40A and 40B which are simplified pictorial illustrations of a needle guard element which forms part of the automatic needle device of FIG. 27, to FIGS. 41A and 41B which are simplified pictorial illustrations of the needle guard element of FIGS. 40A and 40B taken along the lines XLIA-XLIA and XLIB-XLIB in FIG. 40A, to FIGS. 42A and 42B which are respective top and side view simplified planar illustrations of the needle guard element of FIGS. 40A-41B and to FIGS. 43A, 43B and 43C which are sectional illustrations taken along respective section lines and directions XLIIIA-XLIIIA, XLIIIB-XLIIIB and XLIIIC-XLIIIC in FIGS. 42A and 42B.

As seen in FIGS. 40A-43C, the needle guard element 840 preferably is an integrally formed element, preferably injection molded of plastic. Needle guard 840 preferably has a generally cylindrical configuration and is preferably top-to-bottom and side-to-side symmetric about a longitudinal axis 1200, which, when assembled together with housing element 810, resilient element 820 and needle hub 830 is coaxial with longitudinal axis 900 (FIGS. 28A-31C), longitudinal axis 1000 (FIGS. 32A-35B) and longitudinal axis 1100 (FIGS. 36A-39B).

Needle guard element 840 preferably defines a generally tubular body 1210. A plurality of mutually circumferentially spaced, longitudinally extending, outward facing ribs 1212 are formed on a forward outer surface 1214 of generally tubular body 1210. Extending rearwardly of ribs 1212 is a generally cylindrical portion 1216 having a pair of oppositely inward facing axial ribs 1220 and a rearward-facing notch 1224 at the top thereof. Forward of cylindrical portion 1216 and generally in line with notch 1224 there is formed in forward outer surface 1214 a socket 1228 and a bifurcated socket 1229. The notch formed between socket 1228 and bifurcated socket 1229 defines an inclined surface 1230.

Formed on an inner cylindrical surface 1231 of generally tubular body 1210 are a pair of longitudinally extending inner facing ribs 1232 which each terminate in a rearward facing finger 1234 located just forward of generally cylindrical portion 1216. Also formed on inner cylindrical surface 1231 are a pair of longitudinally extending inner facing ribs 1236 which are intersected by sockets 1228 and 1229.

Tubular body 1210 defines a generally open back and a forward facing wall portion 1240, defining an injection site engagement surface characterized in that it has a peripheral array of mutually spaced forwardly extending protrusions 1246. Forward facing wall portion 1240 is formed with an axial bore 1250, arranged to allow needle 834 to extend therethrough.

The needle guard element 840 may optionally be formed a pair of side-to-side symmetric windows, to allow viewing of the tip of the needle 834, for example when purging air bubbles from a syringe. Alternatively, needleguard element 840 may be formed of a transparent material.

Reference is now made to FIGS. 44A, 44B, 44C, 44D, 44E and 44F which are pictorial illustrations of various stages in typical use of the automatic needle device of FIG. 27. The automatic needle device of FIG. 27 is stored prior to use in a pre-use operative orientation.

Figure 44A:
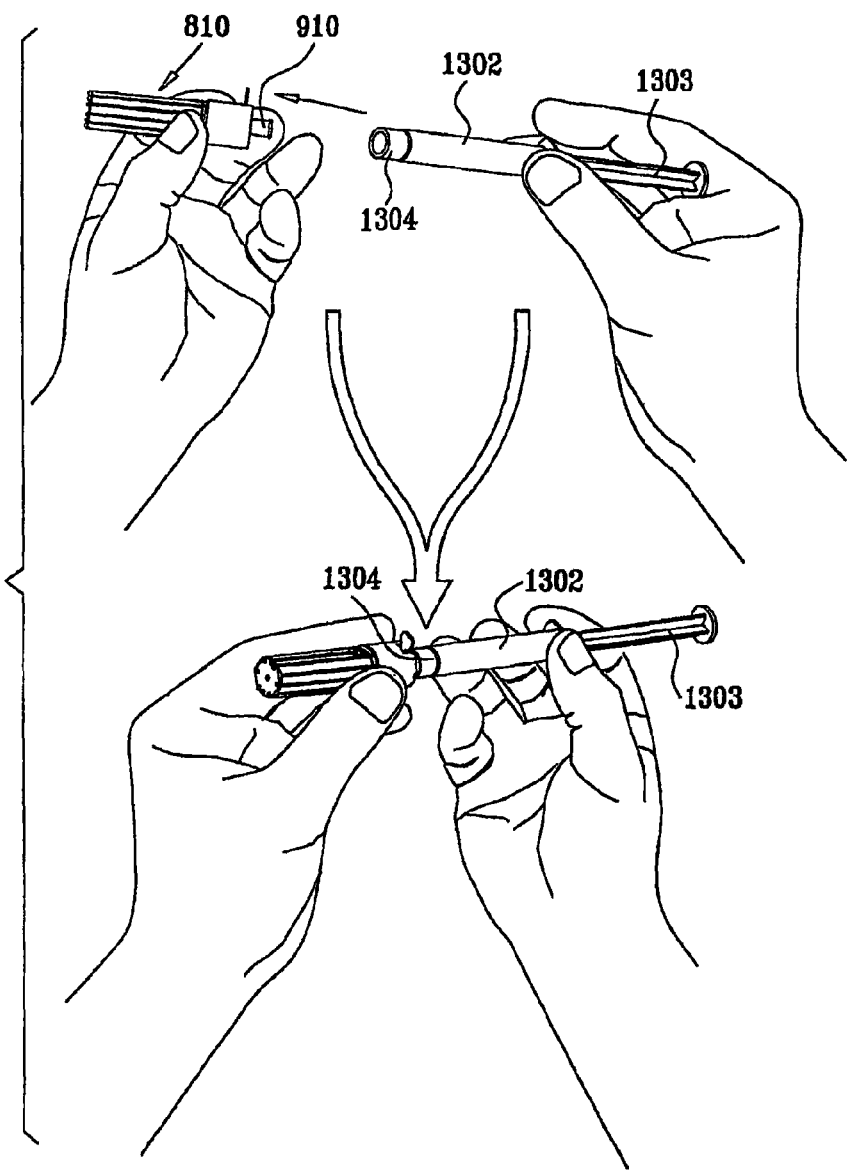
FIGS. 44A, 44B, 44C, 44D, 44E and 44F are simplified pictorial illustrations of typical use of the automatic needle device of FIG. 27.

As shown in FIG. 44A, the user may attach a syringe 1302 to the automatic needle device of FIG. 27, by inserting a forward end 1304 of the syringe into generally tubular portion 910 of housing element 810. A plunger 1306 is inserted in syringe 1302. The operative orientation of the automatic needle device at this stage is described hereinbelow with reference to FIGS. 45-47D.

Figure 44B:
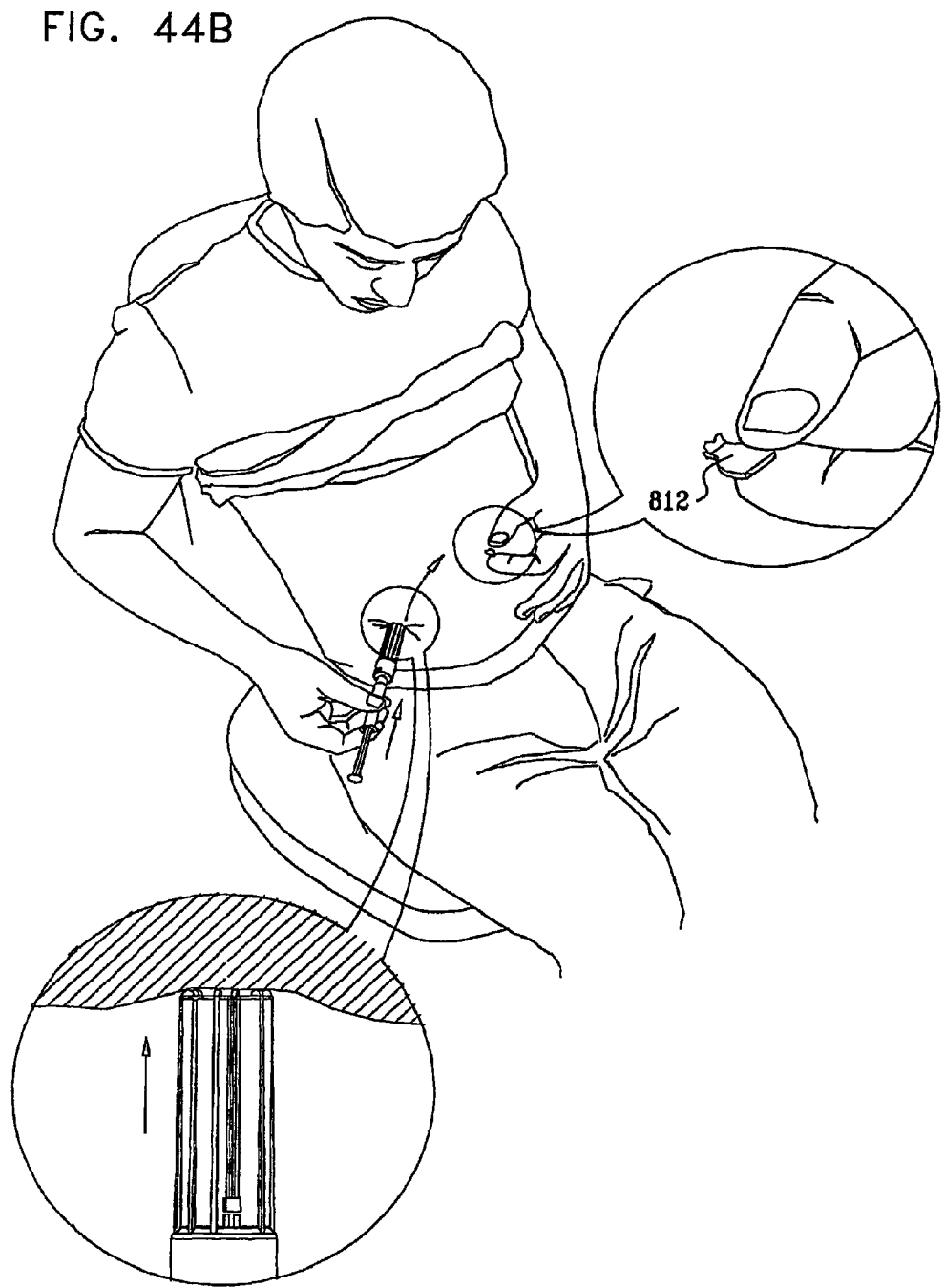
Figure 44C:
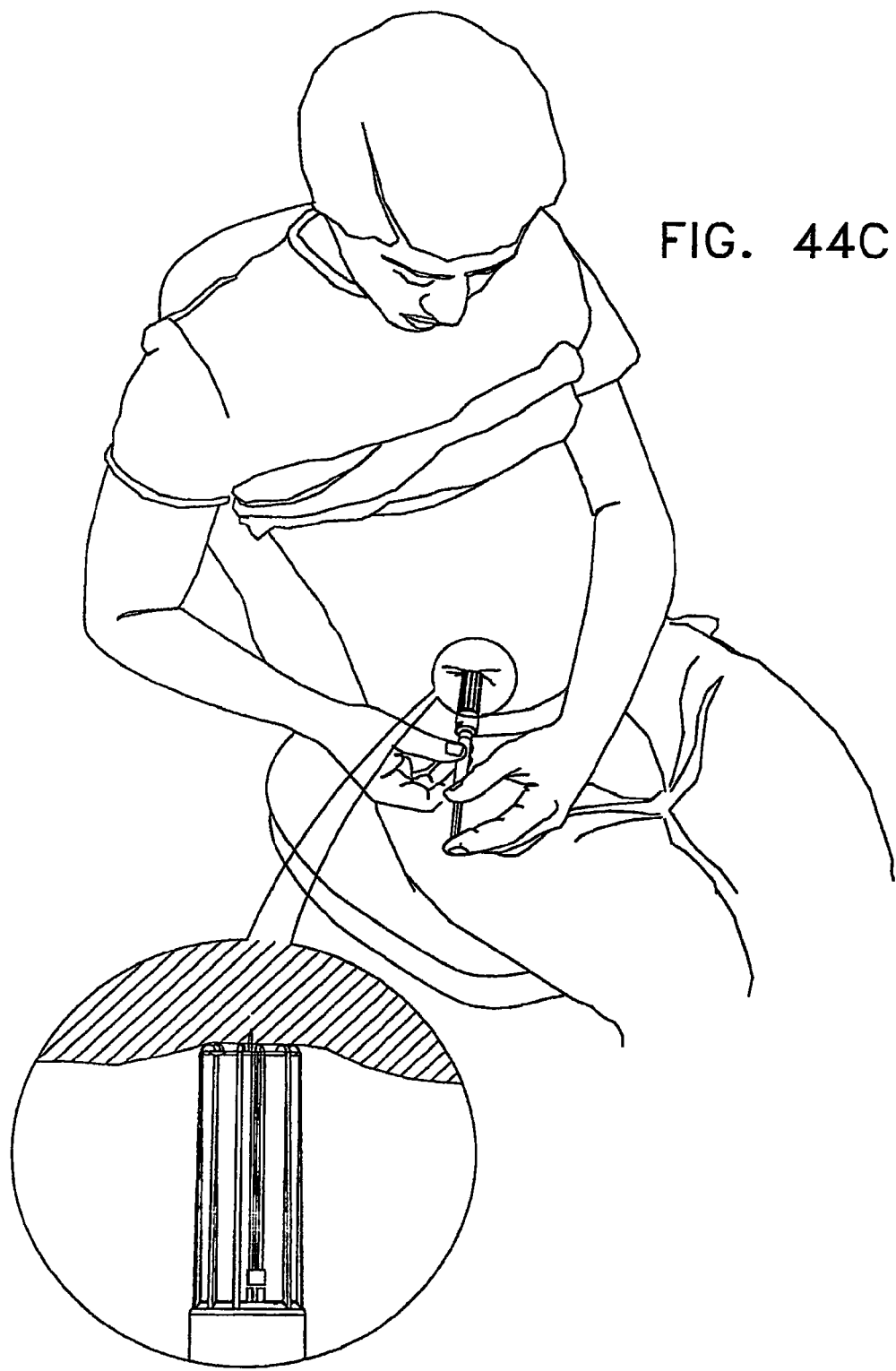

The user then actuates the automatic needle device by removing safety tab 812 and pushing the needle device against an injection site, as shown in FIG. 44B and as described hereinbelow with reference to FIGS. 48-50D. In response to user actuation, needle penetration takes place at the needle site, as shown in FIG. 44C. The operative orientation of the automatic needle device at this stage is described hereinbelow with reference to FIGS. 51-53D.

Figure 44D:
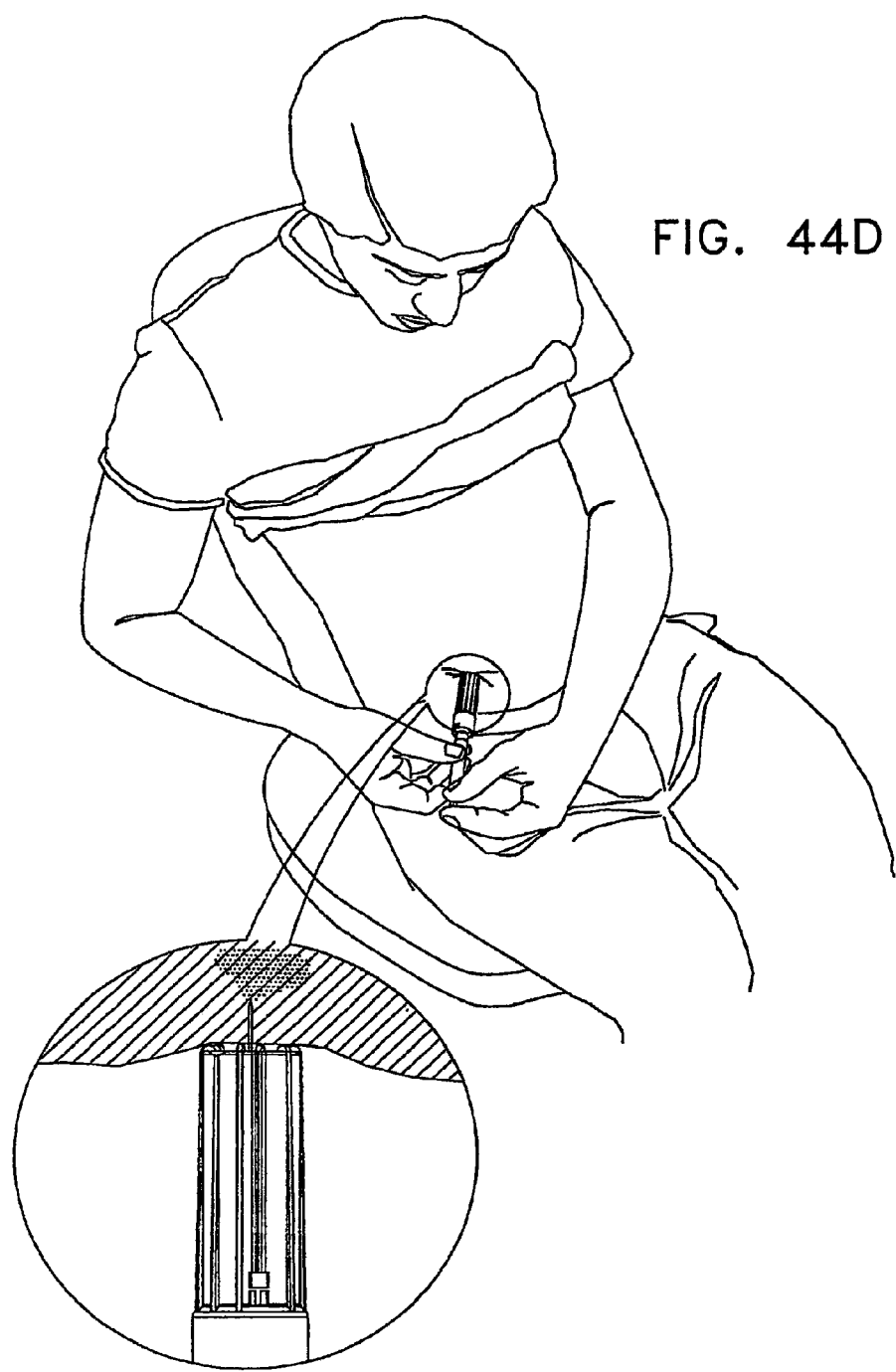

Immediately following needle penetration, drug delivery takes place by the user pushing plunger 1303 of syringe 1302 inward. The operative orientation of the automatic needle device immediately following completion of drug delivery is shown in FIG. 44D and is described hereinbelow with reference to FIGS. 54-56D.

Figure 44E:
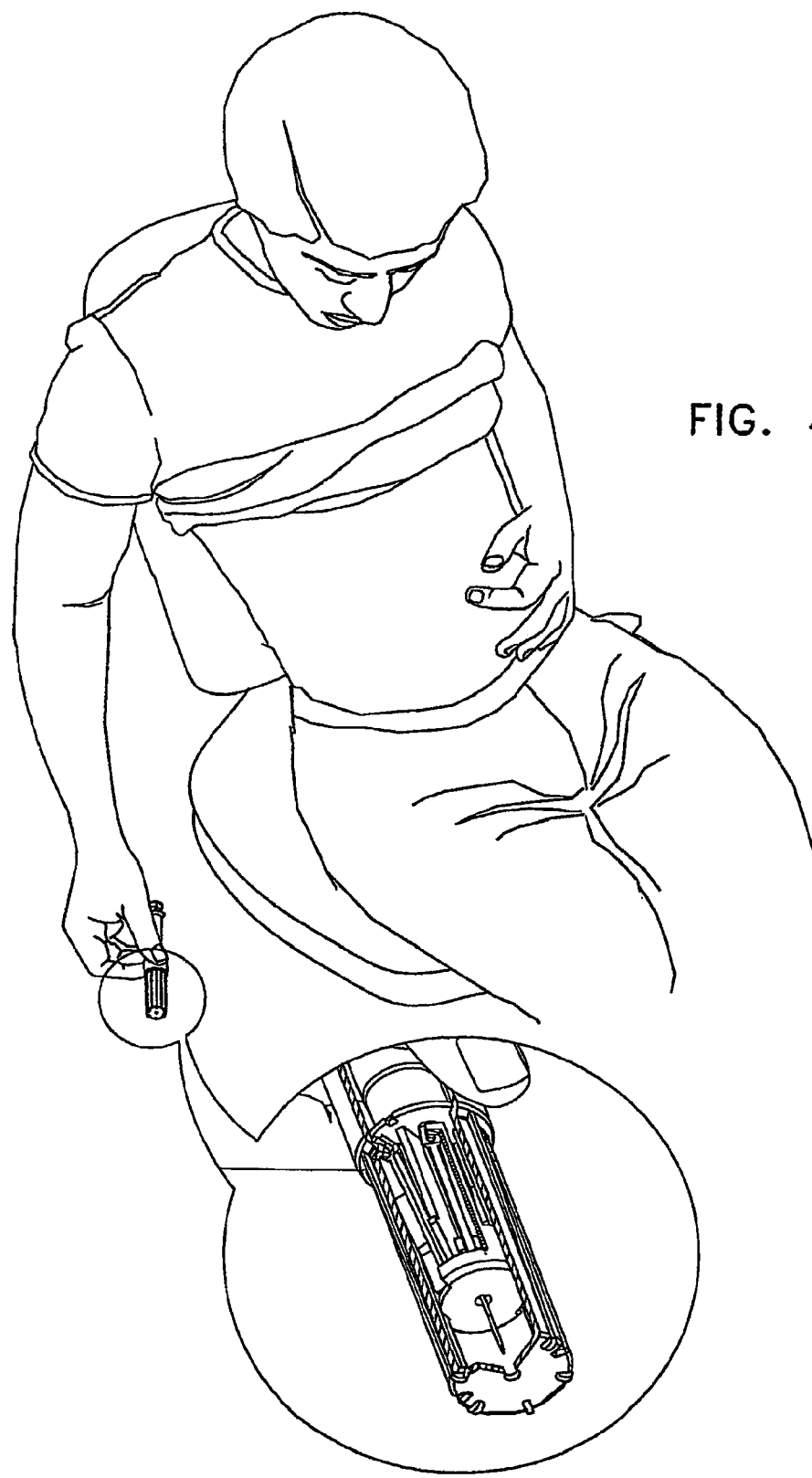

As seen in FIG. 44E, the automatic needle device is then manually disengaged from the injection site. The operative orientation of the automatic injection device at this stage is described hereinbelow with reference to FIGS. 57-59D. Immediately upon disengagement, the needle is protected by the needle guard element 840.

Figure 44F:
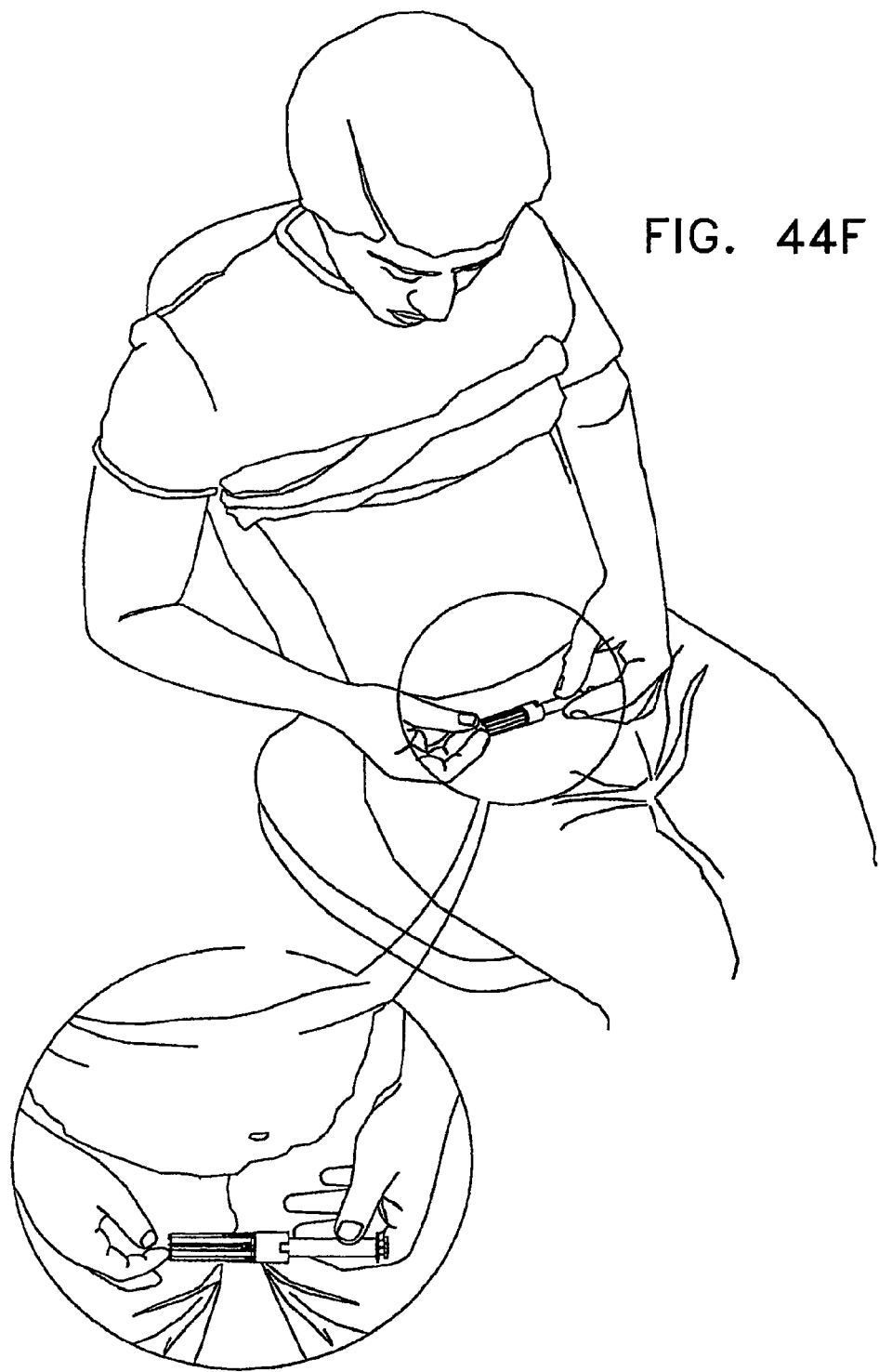

Should the needle guard be forced axially rearward as shown in FIG. 44F, its rearward movement produces corresponding rearward motion of the needle hub assembly 830. The operative orientation of the automatic needle device in this case is described hereinbelow with reference to FIGS. 60-62D.

Reference is now made to FIG. 45, which is a simplified assembled view illustration of the automatic needle device of FIGS. 27 and 44A in a pre-use operative orientation coupled to a syringe and prior to removal of a safety tab, to FIGS. 46A and 46B, which are respective top and side view simplified planar illustrations thereof, to FIGS. 47A and 47B, which are sectional illustrations taken along respective section lines and directions XLVIIA-XLVIIA and XLVIIB-XLVIIB in FIGS. 46A and 46B, to FIG. 47C which is a simplified illustration corresponding to FIG. 46A with the needle guard hidden and to FIG. 47D which is a simplified partially cut-away illustration of the needle guard element 840 and the needle hub assembly 830 of FIG. 46B.

As seen in FIGS. 45-47D, in a pre-use operative orientation of the automatic needle device, the needle hub assembly 830 is urged forwardly along axis 900 relative to housing element 810 by tensioned arms 1033 and 1034 of resilient element 820. End portions 1037 of arms 1033 and 1034 engage corresponding rearward facing fingers 1162 of needle hub assembly 830, while the cylindrical portion 1010 of the resilient element 820 is retained in socket 954 formed in housing element 810.

The housing element 810 retains the needle hub assembly 830 against axial forward displacement relative to housing element 810 by engagement of rearward facing shoulders 926 of ribs 920 of housing element 810 with corresponding rear surfaces 1156 of longitudinal slots 1154 formed in arms 1150 of needle hub assembly 830.

In the pre-use operative orientation of the automatic needle device, the needle guard element 840 is urged forwardly along axis 900 relative to housing element 810 by tensioned arms 1035 and 1036 of resilient element 820. End portions 1037 of arms 1035 and 1036 engage corresponding rearward facing fingers 1234 formed on inner cylindrical surface 1231 of generally tubular body 1210 of the needle guard element 840, while the cylindrical portion 1010 of the resilient element 820 is retained in socket 954 formed in housing element 810.

The needle hub assembly 830 retains the needle guard element 840 against axial forward displacement relative to housing element 810 by engagement of right angle fingers 1122 of needle hub assembly 830 with bifurcated sockets 1229 formed in needle guard element 840.

Safety tab 812 mounted on flange 916 of housing element 810 prevents rearward axial displacement of needle guard element 840 relative to housing element 810.

Reference is now made to FIG. 48, which is a simplified pictorial illustration of the automatic needle device of FIGS. 27 and 44B in an injection site engagement operative orientation following removal of the safety tab 812 from housing element 810, to FIGS. 49A and 49B, which are respective top and side view simplified planar illustrations thereof, to FIGS. 50A and 50B which are sectional illustrations taken along respective section lines and directions LA-LA and LB-LB in FIGS. 49A and 49B, to FIG. 50C which is a simplified illustration corresponding to FIG. 49A with the needle guard hidden and to FIG. 50D which is a simplified partially cut-away illustration of the needle guard element 840 and the needle hub assembly 830 of FIG. 49B.

As seen particularly in FIG. 50A, due to engagement of the needle guard element 840 with an injection site on a body, the needle guard 840 is forced, against the urging of tensioned arms 1035 and 1036, to move axially in a rearward direction with respect to the housing element 810. This displacement stretches tensioned arms 1035 and 1036.

This rearward repositioning of needle guard element 840 produces an identical rearward displacement of needle hub assembly 830, against the urging of tensioned arms 1033 and 1034, by virtue of engagement of right angle fingers 1122 of needle hub assembly 830 with bifurcated sockets 1229 formed in needle guard element 840. This displacement stretches tensioned arms 1033 and 1034.

The rearward displacement of the needle hub assembly 830 causes the needle 834 to be displaced rearwardly by an identical amount with respect to cylindrical portion 1018 of resilient element 820.

Reference is now made to FIG. 51, which is a simplified pictorial illustration of the automatic needle device of FIGS. 27 and 44C in a needle actuated operative orientation, to FIGS. 52A and 52B which are respective top and side view simplified planar illustrations thereof, to FIGS. 53A and 53B which are sectional illustrations taken along respective section lines and directions LIIIA-LIIIA and LIIIB-LIIIB in FIGS. 52A and 52B, to FIG. 53C which is a simplified illustration corresponding to FIG. 52A with the needle guard hidden and to FIG. 53D which is a simplified partially cut-away illustration of the needle guard element 840 and the needle hub assembly 830 of FIG. 52B.

As seen particularly in FIG. 53A, due to rearward displacement of the needle guard element 840 and of the needle hub assembly 830 relative to the housing element 810 and specifically relative to planar portion 934 thereof, the right angle fingers 1122 are now free to be cantilevered inwardly by sliding along rearward facing inclined surfaces 1230 and to slide forwardly along tapered rearward facing surfaces 938 thereof and along inner facing surfaces of planar portions 934, thus permitting axial forward motion of the needle hub assembly 830 under the urging of tensioned arms 1033 and 1034, which become less stretched as a result.

The forward displacement of the needle hub assembly 830 causes the needle 834 to be displaced forwardly with respect to cylindrical portion 1018 of resilient element 820.

The forward axial motion of the needle hub assembly 830 produces needle penetration at the injection site.

Figure 54:
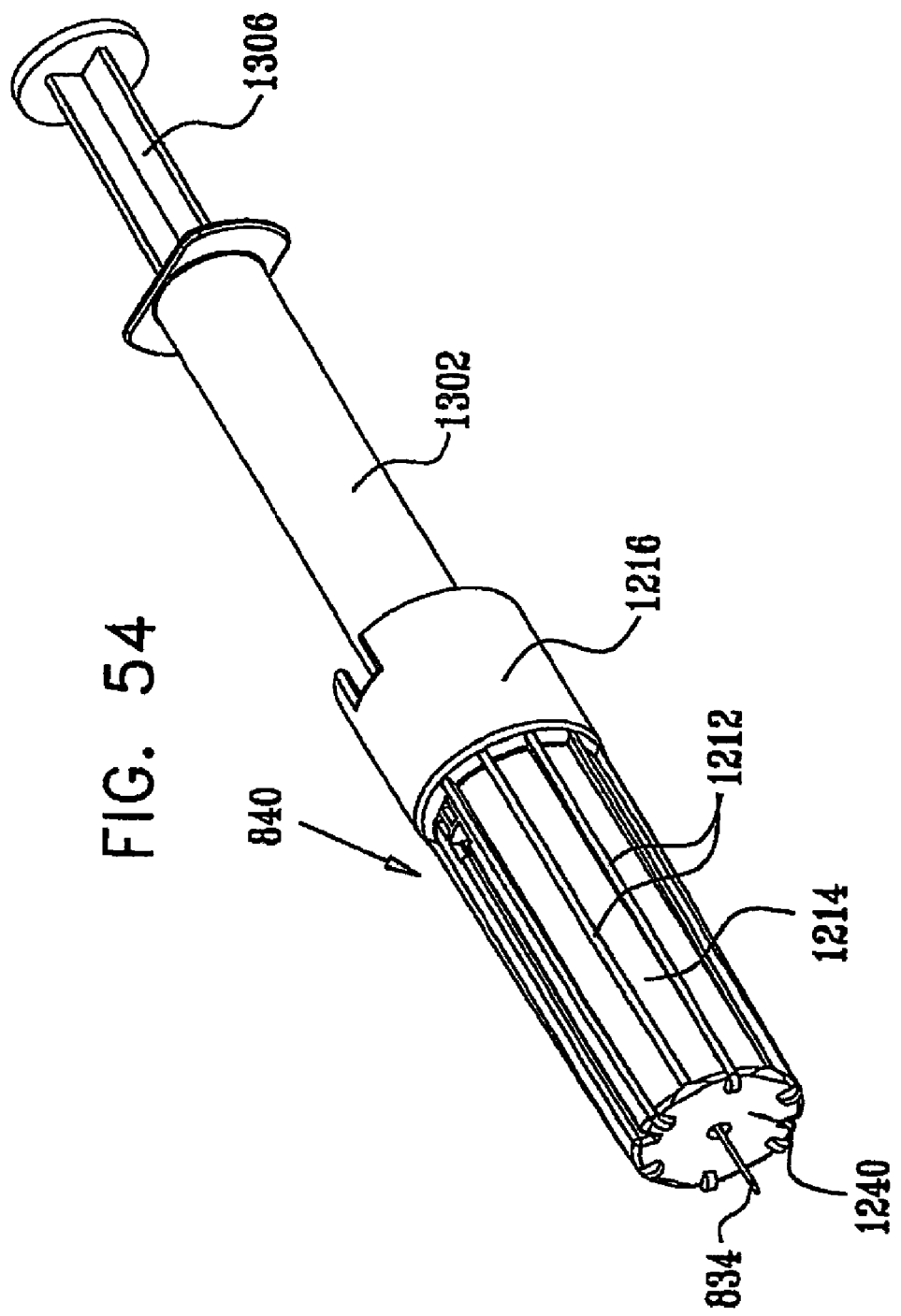
FIG. 54 is a simplified pictorial illustration of the automatic needle device of FIGS. 27 and 44D in an immediate post drug delivery operative orientation.

Reference is now made to FIG. 54, which is a simplified pictorial illustration of the automatic needle device of FIGS. 27 and 44D in a full needle penetration and an immediately post drug delivery operative orientation, to FIGS. 55A and 55B, which are respective top and side view simplified planar illustrations thereof, to FIGS. 56A and 56B, which are sectional illustrations taken along respective section lines and directions LVIA-LVIA and LVIB-LVIB in FIGS. 55A and 55B, to FIG. 56C which is a simplified illustration corresponding to FIG. 55A with the needle guard hidden and to FIG. 56D which is a simplified partially cut-away illustration of the needle guard element 840 and the needle hub assembly 830 of FIG. 55B.

It is seen that the needle hub assembly 830 is a forward axial position, at which right angle fingers 1122 are seated in respective sockets 948, thus locking the needle hub assembly 830 to housing element 810. In this position, the right angle fingers 1122 are bent circumferentially and radially inward and are retained in this orientation by engagement with respective ribs 1236 formed on inner cylindrical surface 1231 of needle guard element 840. The further axial forward motion of the needle hub assembly 830 under the urging of tensioned arms 1033 and 1034 causes arms 1033 and 1034 to be even less stretched.

Full needle penetration is provided at this stage and a user normally injects a drug into the injection site by depressing plunger 1306 of syringe 1302.

Figure 57:
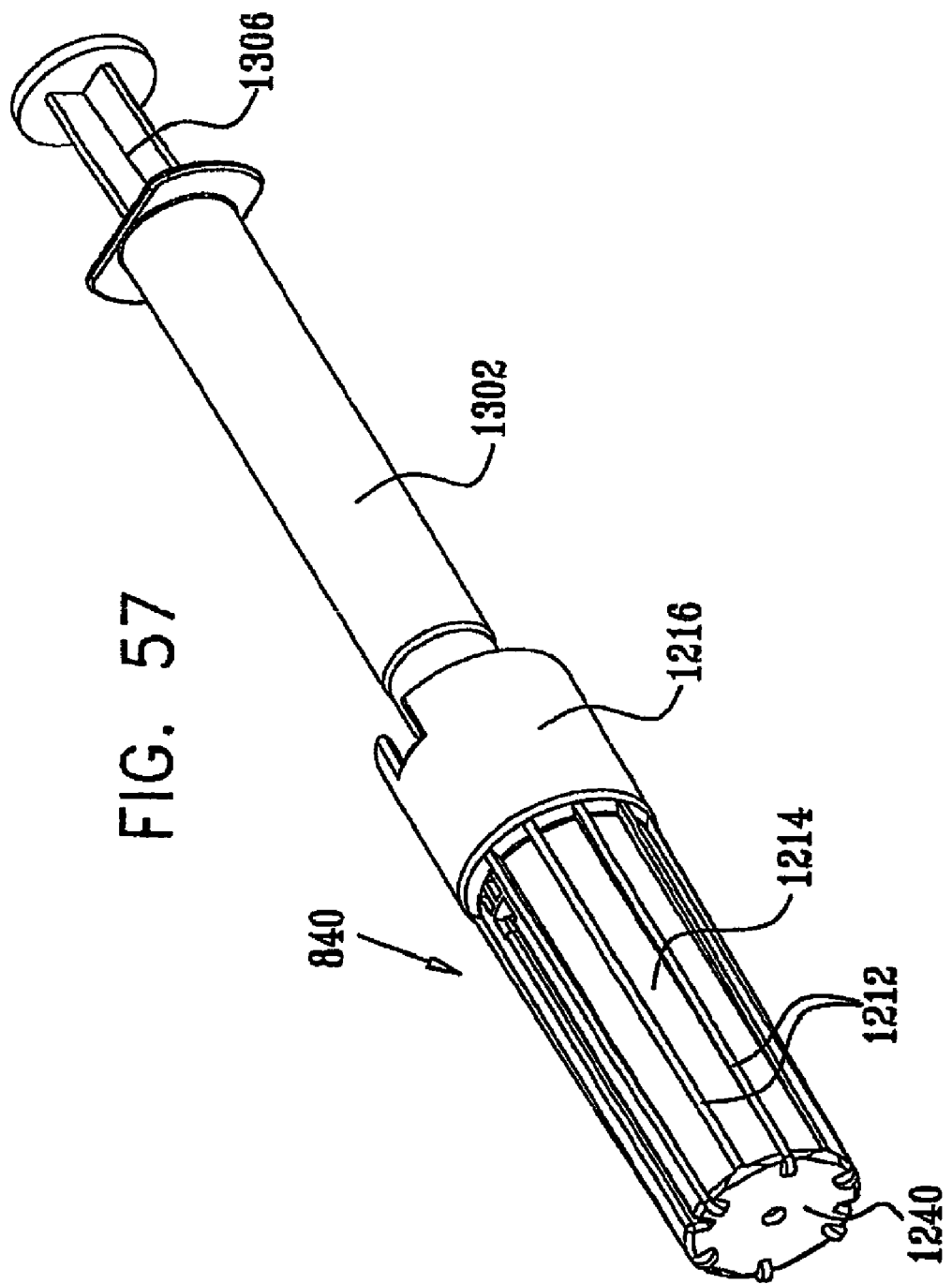
FIG. 57 is a simplified pictorial illustration of the automatic needle device of FIGS. 27 and 44E in a post-drug delivery, needle guarded operative orientation.

Reference is now made to FIG. 57 which is a simplified pictorial illustration of the automatic needle device of FIGS. 27 and 14E in a post-drug delivery, needle guarded operative orientation, to FIGS. 58A and 58B, which are respective top and side view simplified planar illustrations of the automatic needle device of FIG. 57, to FIGS. 59A and 59B which are sectional illustrations taken along respective section lines and directions LIXA-LIXA and LIXB-LIXB in FIGS. 58A and 58B, to FIG. 59C which is a simplified illustration corresponding to FIG. 58A with the needle guard hidden and to FIG. 59D which is a simplified partially cut-away illustration of the needle guard element 840 and the needle hub assembly 830 of FIG. 58B.

FIGS. 57-59D illustrate the automatic needle device fully disengaged from the needle site and the needle guard element 840 fully extended under the urging of tensioned arms 1035 and 1036 to fully enclose the needle 834. The needle guard 840 is prevented from moving further forward by engagement of right angle fingers 1122 of needle hub assembly 830 in respective sockets 1128 formed in needle guard element 840 and by engagement of rearward facing shoulders 926 of ribs 920 of housing element 810 with corresponding rear surfaces 1156 of longitudinal slots 1154 formed in arms 1150 of needle hub assembly 830.

Figure 60:
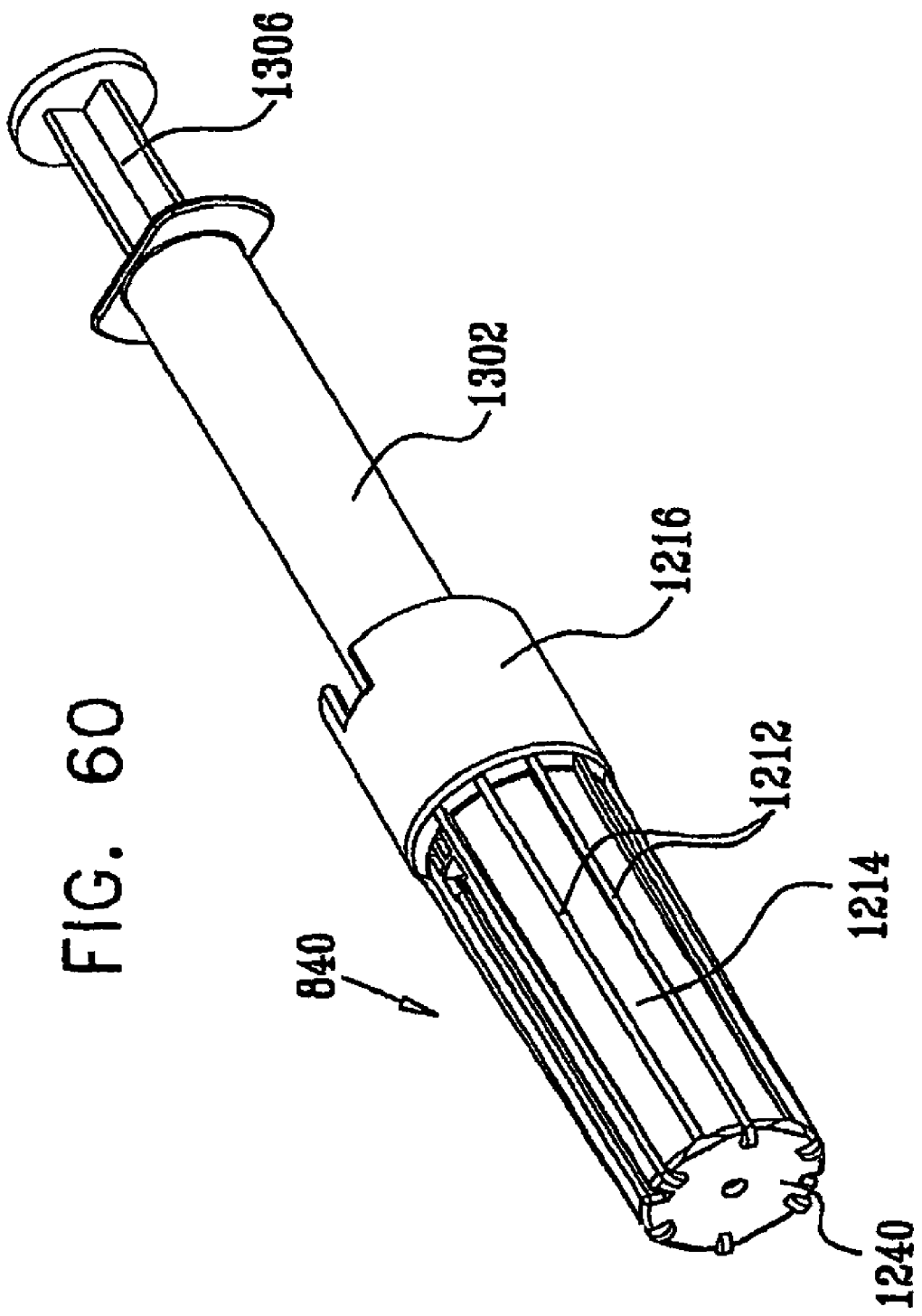
FIG. 60 is a simplified pictorial illustration of the automatic needle device of FIGS. 27 and 44F in a needle guard pushed back misuse operative orientation.
Figure 61A:
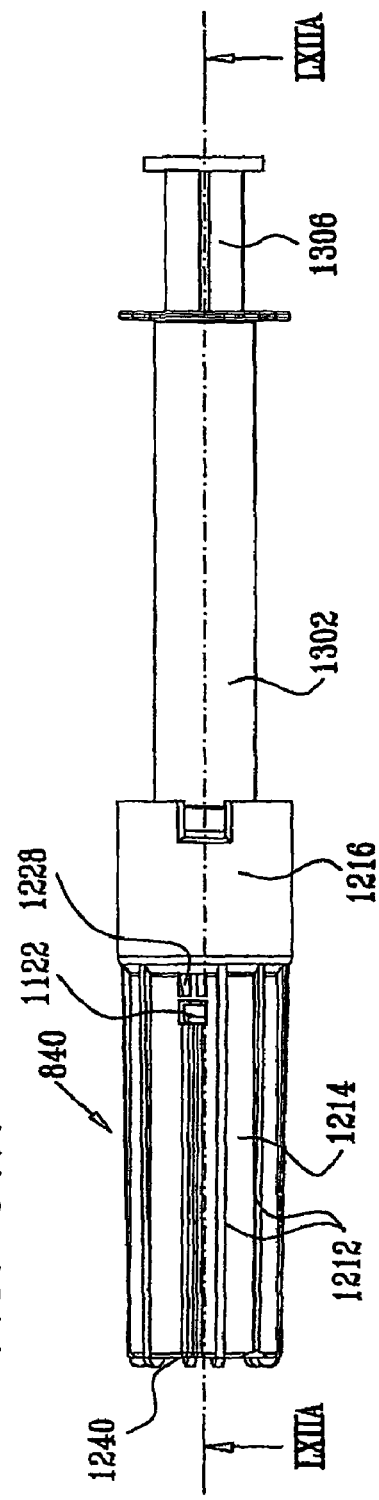
FIGS. 61A and 61B are respective top and side view simplified planar illustrations of the automatic needle device of FIG. 60.
Figure 61B:
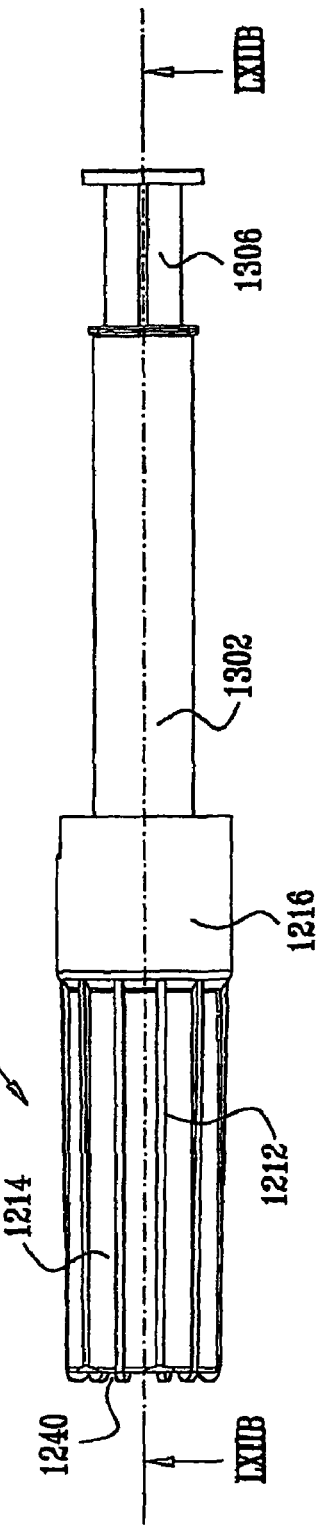

Reference is now made to FIG. 60 which is a simplified pictorial illustration of the automatic needle device of FIGS. 27 and 44F in a needle guard pushed back misuse operative orientation, to FIGS. 61A and 61B which are respective top and side view simplified planar illustrations of the automatic needle device of FIG. 60, to FIGS. 62A and 62B are sectional illustrations taken along respective section lines and directions LXIIA-LXIIA and LXIIB-LXIIB in FIGS. 61A and 61B, to FIG. 62C which is a simplified illustration corresponding to FIG. 61A with the needle guard hidden and to FIG. 62D which is a simplified partially cut-away illustration of the needle guard element 840 and the needle hub assembly 830 of FIG. 61B.

FIGS. 60-62D illustrate an important feature of the present invention provided by engagement of right angle fingers 1122 of needle hub assembly 830 in respective sockets 1128 formed in needle guard 840. Should the needle guard 840 be pushed rearwardly with respect to housing element 810, needle hub assembly 830 and needle 834 move axially rearwardly together with needle guard element, so that the needle 834 does not protrude from the needle guard 840. It is appreciated that the automatic needle device can be attached to various types of injection devices, and that the a luer adapter defined by an internal tapered surface of the tubular portion 110 of the housing element 10 of the automatic needle device may be readily modified for engagement with various injection devices such as pen injectors. It is also possible to integrate the automatic needle apparatus described herein into another injection device and thus to eliminate the need for a luer adapter.

Figure 63:
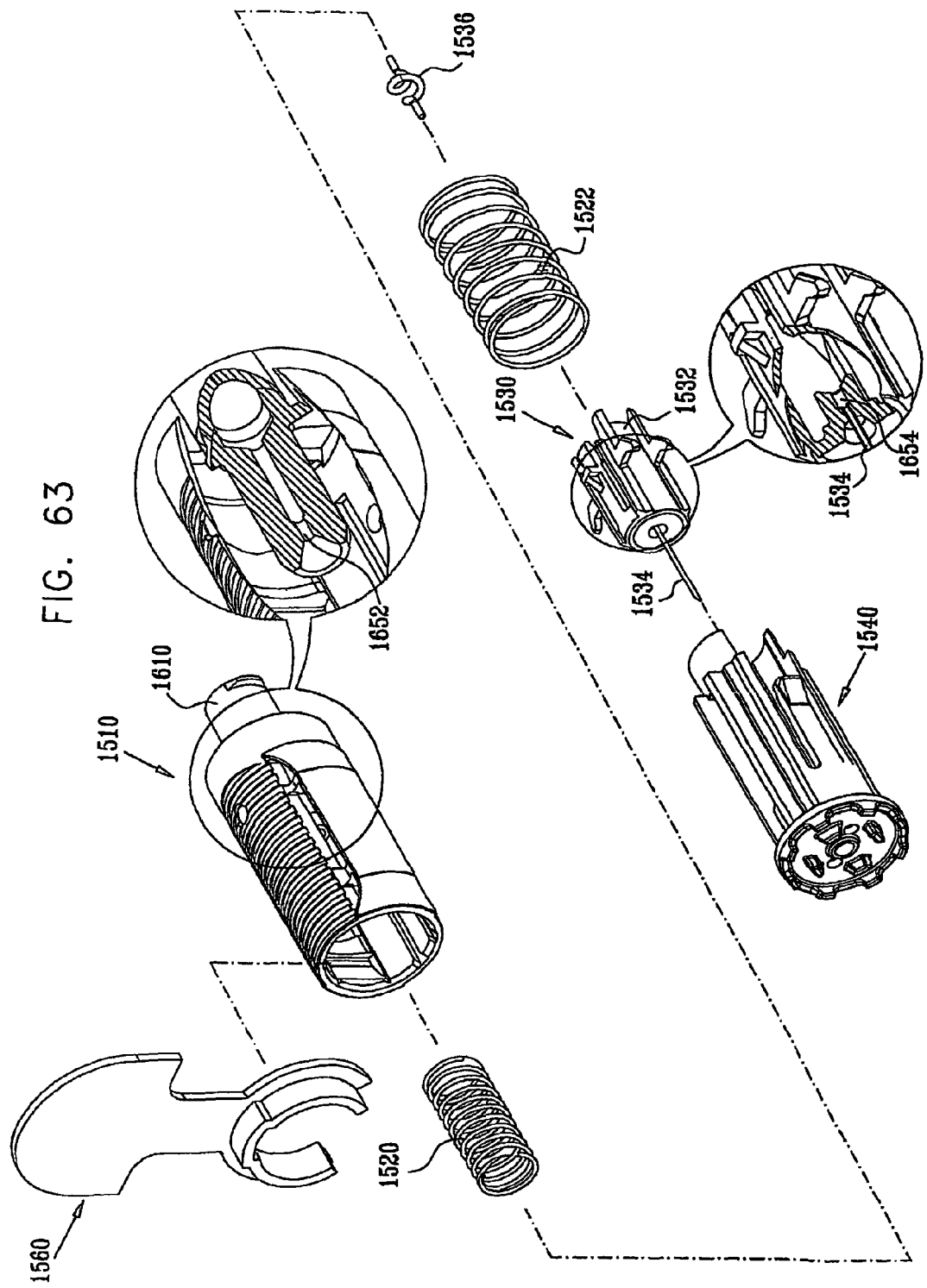
FIG. 63 is a simplified exploded view illustration of an automatic needle device constructed and operative in accordance with yet another preferred embodiment of the present invention, which is a modified version of the embodiment of FIGS. 1-26.

Reference is now made to FIGS. 63-75B, which illustrate an automatic needle device constructed and operative in accordance with yet another preferred embodiment of the present invention. The embodiment of FIGS. 63-75B is a modification of the embodiment of FIGS. 1-26B. Accordingly, for the sake of conciseness, it is described in somewhat abbreviated form hereinbelow:

As seen with particular clarity in FIG. 63, the automatic needle device comprises a housing element 1510 into which are generally coaxially seated respective first and second compression springs 1520 and 1522, which provide selectable forward displacement to a needle hub assembly 1530, which includes a hub portion 1532 and a needle 1534 adhesively adhered thereto and rearwardly coupled to a forward end of an elastic tube 1536, whose rearward end is coupled to a liquid passage passageway formed in housing element 1510, and to a needle guard element 1540. Alternatively, needle hub portion 1532 may be injected onto the needle, by a method such as insert molding.

A safety tab 1560 is preferably mounted onto the forward section of housing element 1510, thus disabling actuation of the automatic needle device. The automatic needle device is only functional once the safety tab is removed, as described hereinbelow.

It will be appreciated that safety tab 1560 can be formed of any suitable material, for example such as polypropylene, and may be formed in various configurations, such as a portion which is inserted into a slot between the needle guard element 1540 and the housing element 1510, as a stand alone injection molded part, or as an integral part of any of the parts of the automatic needle device such as the housing element 1510 as described hereinabove with reference to FIGS. 27-62D, the needle guard element 1540 or the needle hub assembly 1530.

It will additionally be appreciated by those skilled in the art that compression springs 1520 and 1522 may be replaced with a resilient element as described hereinabove with reference to FIGS. 27-62D. Alternatively, compression springs 1520 and 1522 may be replaced by tension springs, elastomeric compression springs or plastic springs which are preferably integrated into housing element 1510, into needle hub assembly 1530 or into needle guard element 1540.

Reference is now made to FIGS. 2A and 2B, which are simplified pictorial illustrations of a preferred housing element 10 which forms part of the automatic needle device of FIG. 1, to FIGS. 3A and 3B are respective top and side view simplified planar illustrations thereof, to FIGS. 4A and 4B which are sectional illustrations taken along respective section lines and directions IVA-IVA and IVB-IVB in FIGS. 3A and 3B and to FIGS. 5A and 5B which are pictorial sectional illustrations taken along respective section lines and directions VA-VA and VB-VB in FIG. 2A.

Housing element 1510 is identical to the housing element 10 other than in the following respect, shown in FIG. 63:

Communicating with an interior of rearward generally tubular portion 1610 there is provided a narrow passageway 1652 which sealingly receives the rearward end of elastic tube 1536.

Reference is now made to FIGS. 6A and 6B, which are simplified pictorial illustrations of a needle hub assembly 30 which forms part of the automatic needle device of FIG. 1, to FIGS. 7A and 7B, which are respective top and side view simplified planar illustrations of the needle hub assembly of FIGS. 6A and 6B, to FIGS. 8A and 8B, which are sectional illustrations taken along respective section lines and directions VIIIA-VIIIA and VIIIB-VIIIB in FIGS. 7A and 7B and to FIGS. 9A and 9B, which are pictorial sectional illustrations taken along respective section lines and directions IXA-IXA and IXB-IXB in FIG. 6A.

Needle hub assembly 1530 is identical to needle hub assembly 30 shown in FIGS. 6A-9B, except in that the needle 1534 is shorter than needle 34 in the embodiment of FIGS. 1-26B, due to the provision of the elastic tube 1536, the forward end of which is sealingly located in a narrow passageway 1654 provided in the needle hub assembly.

Reference is now made to FIGS. 10A and 10B, which are simplified pictorial illustrations of a needle guard element 40 which forms part of the automatic needle device of FIG. 1, to FIGS. 11A and 11B, which are respective top and side view simplified planar illustrations of the needle guard element of FIGS. 10A and 10B, to FIGS. 12A and 12B, which are sectional illustrations taken along respective section lines and directions XIIA-XIIA and XIIB-XIIB in FIGS. 11A and 11B and to FIGS. 13A and 13B which are pictorial sectional illustrations taken along respective section lines and directions XIIIA-XIIIA and XIIIB-XIIIB in FIG. 10A.

The needle guard element 1540 is identical to needle guard element 40 shown in FIGS. 10A-13B.

Reference is now made to FIGS. 14A, 14B, 14C and 14D which when taken together form a simplified pictorial illustration of various stages of typical use of the automatic needle device of FIG. 1. FIGS. 14A-14D also illustrate the various stages of typical use of the automatic needle device of FIG. 63 and the above description of FIGS. 14A-14D applies to the embodiment of FIGS. 63-75B as well.

Figure 64A:
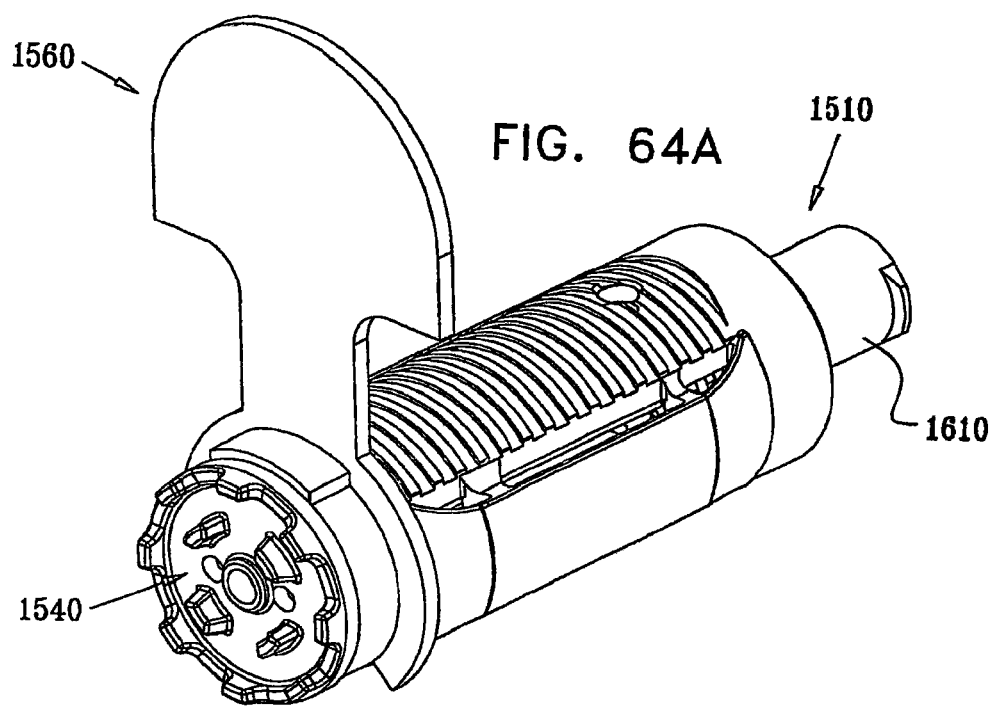
FIGS. 64A and 64B are simplified assembled view illustrations of the automatic needle device of FIG. 63 in a pre-use operative orientation.
Figure 64B:
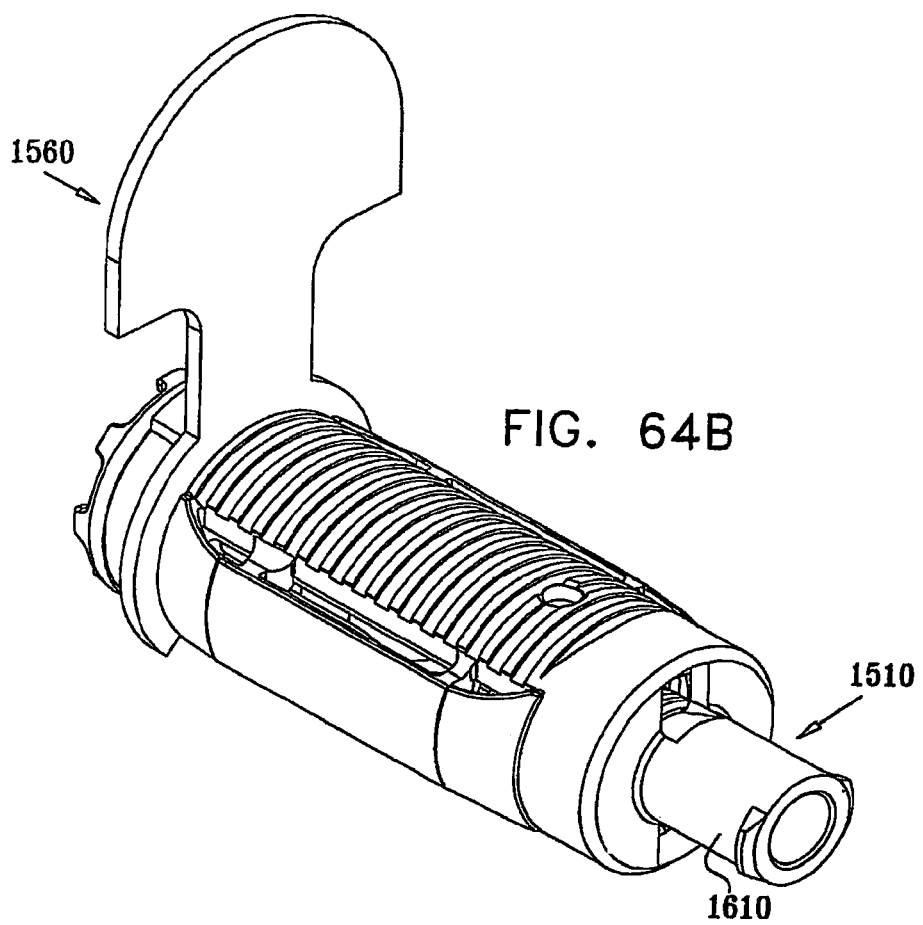
Figure 65A:
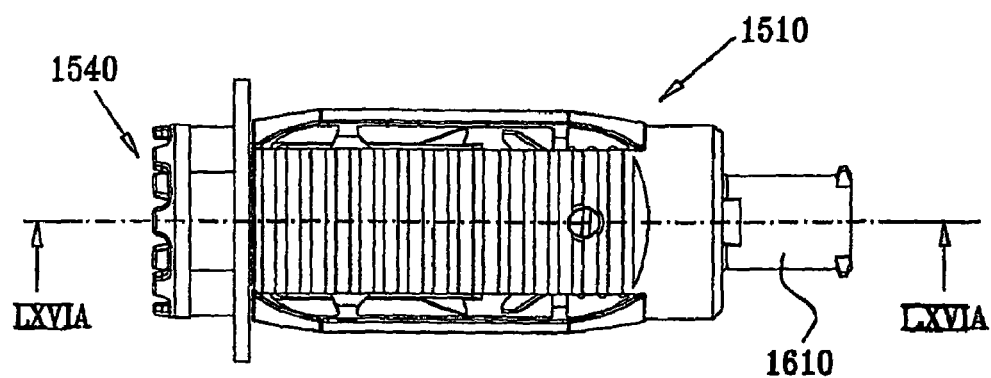
FIGS. 65A and 65B are respective top and side view simplified planar illustrations of the automatic needle device of FIGS. 64A and 64B.
Figure 65B:
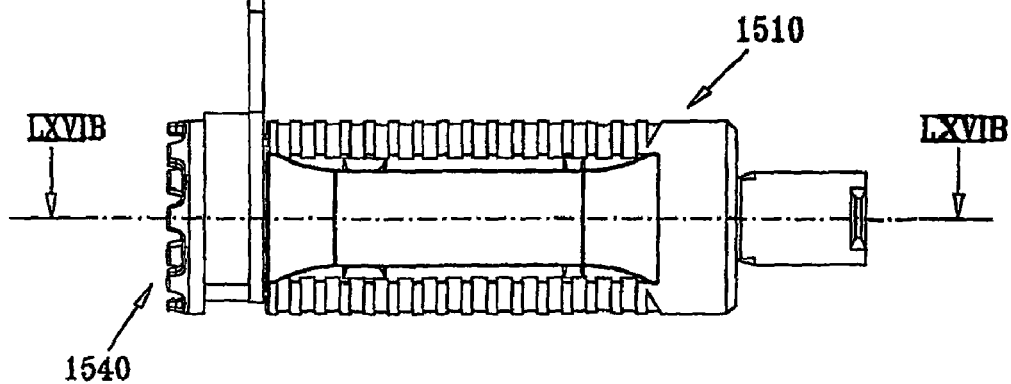
Figure 66A:
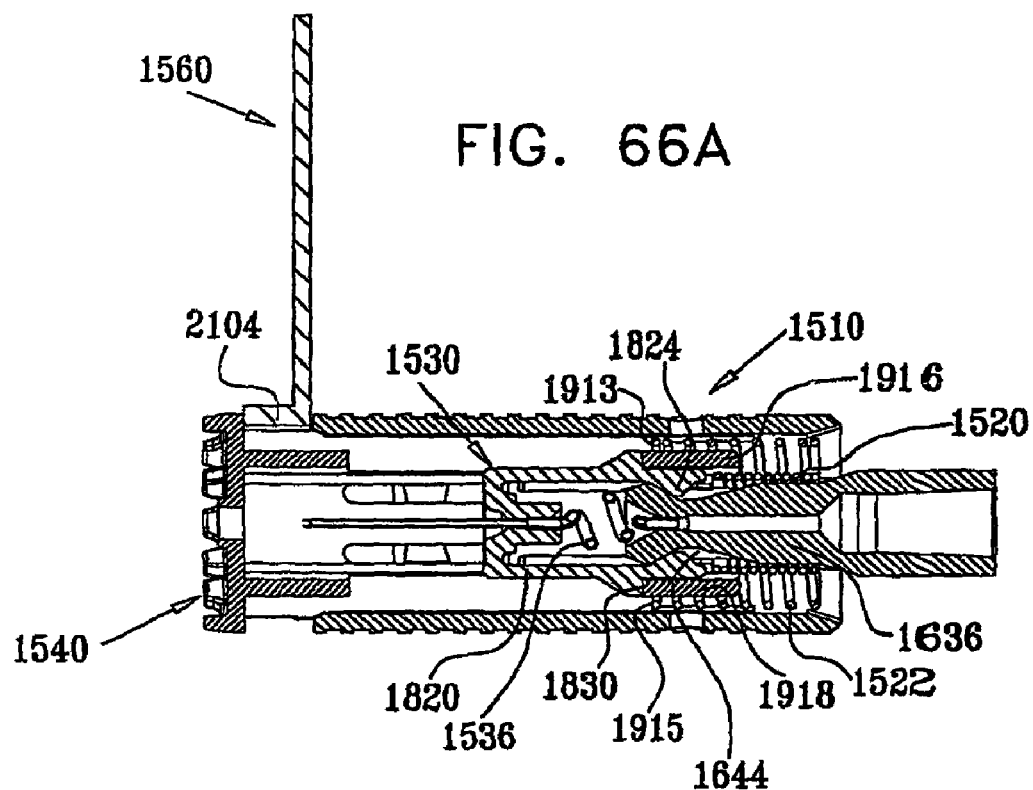
FIGS. 66A and 66B are sectional illustrations taken along respective section lines and directions LXVIA-LXVIA and LXVIB-LXVIB in FIGS. 65A and 65B.
Figure 66B:
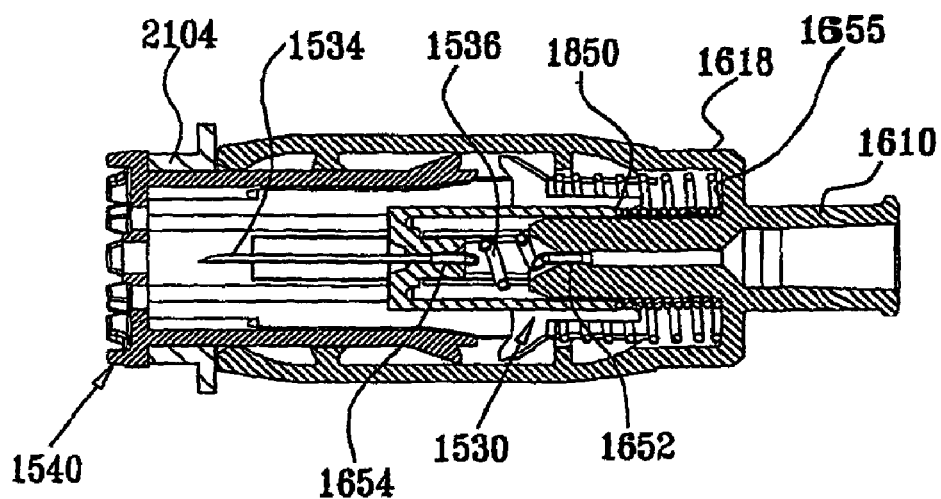

Reference is now made to FIGS. 64A and 64B, which are simplified assembled view illustrations of the automatic needle device of FIG. 63 in a pre-use operative orientation, to FIGS. 65A and 65B, which are respective top and side view simplified planar illustrations thereof and to FIGS. 66A and 66B, which are sectional illustrations taken along respective section lines and directions LXVIA-LXVIA and LXVIB-LXVIB in FIGS. 65A and 65B.

As seen in FIGS. 64-66B, in a pre-use operative orientation of the automatic needle device, suitable for storage, the housing element 1510 is joined to the needle hub assembly 1530 by engagement of inner facing teeth 1824 into apertures 1644 formed in the cylindrical walls of bore 1636. First and second compression springs 1520 and 1522 are located mutually coaxially within housing element 1510. Compression spring 1520 is maintained under compression between forward-facing back wall surface 1655 of generally cylindrical portion 1618 of housing element 1510 and rearward facing wall portion 1850 of hub assembly 1530. Compression spring 1522 is maintained under compression between forward facing back wall surface 1655 and rearward facing ends 1913 and 1915 of needle guard element 1540, which is slidably retained against forward movement by the positioning of curved rearward facing portions 1916 and 1918 thereof immediately rearward of teeth 1826 of needle hub assembly 1530.

The needle hub assembly 1530 is retained in its place by engagement of outwardly facing surface of inner facing teeth 1824 of rearwardly extending arm 1820 and curved rearward facing portions 1916 and 1918 of needle guard element 1540, thus preventing rearwardly extending arms 1820 of needle hub assembly 1530 from bending outwards and releasing the engagement of inner facing teeth 1824 and apertures 1644 formed in the cylindrical walls of bore 1636 of the housing 1510. The tubular portion 2104 of safety tab 1560 prevents the needle guard element 1540 from moving backwards and actuating needle penetration.

It is seen that the elastic tube 1536 is in a relatively compressed state and is coupled at a forward end thereof to narrow passageway 1654 provided in the needle hub assembly 1530 and is coupled at a rearward end thereof to narrow passageway 1652 formed in housing element 1510.

Reference is now made to FIG. 67, which is a simplified pictorial illustration of the automatic needle device of FIG. 63 after coupling thereto of a syringe 2002 in an injection site engagement operative orientation, to FIGS. 68A and 68B, which are respective top and side view simplified planar illustrations thereof and to FIGS. 69A and 69B, which are sectional illustrations taken along respective section lines and directions LXIXA-LXIXA and LXIXB-LXIXB in FIGS. 68A and 68B.

As seen particularly in FIG. 69A, due to engagement of the needle guard element 1540 with an injection site on a body, the needle guard 1540 is forced, against the urging of spring 1522, to move axially in a rearward direction with respect to the remainder of the automatic needle device, thus sliding curved rearward facing portions 1916 and 1918 thereof further rearward of teeth 1826 of needle hub assembly 1530.

This rearward repositioning of curved rearward facing portions 1916 and 1918 and the pressure of spring 1520, allow arms 1820 of needle hub assembly 1530 to cantilever outward.

It is seen that the elastic tube 1536 is in a relatively extended state.

Figure 70:
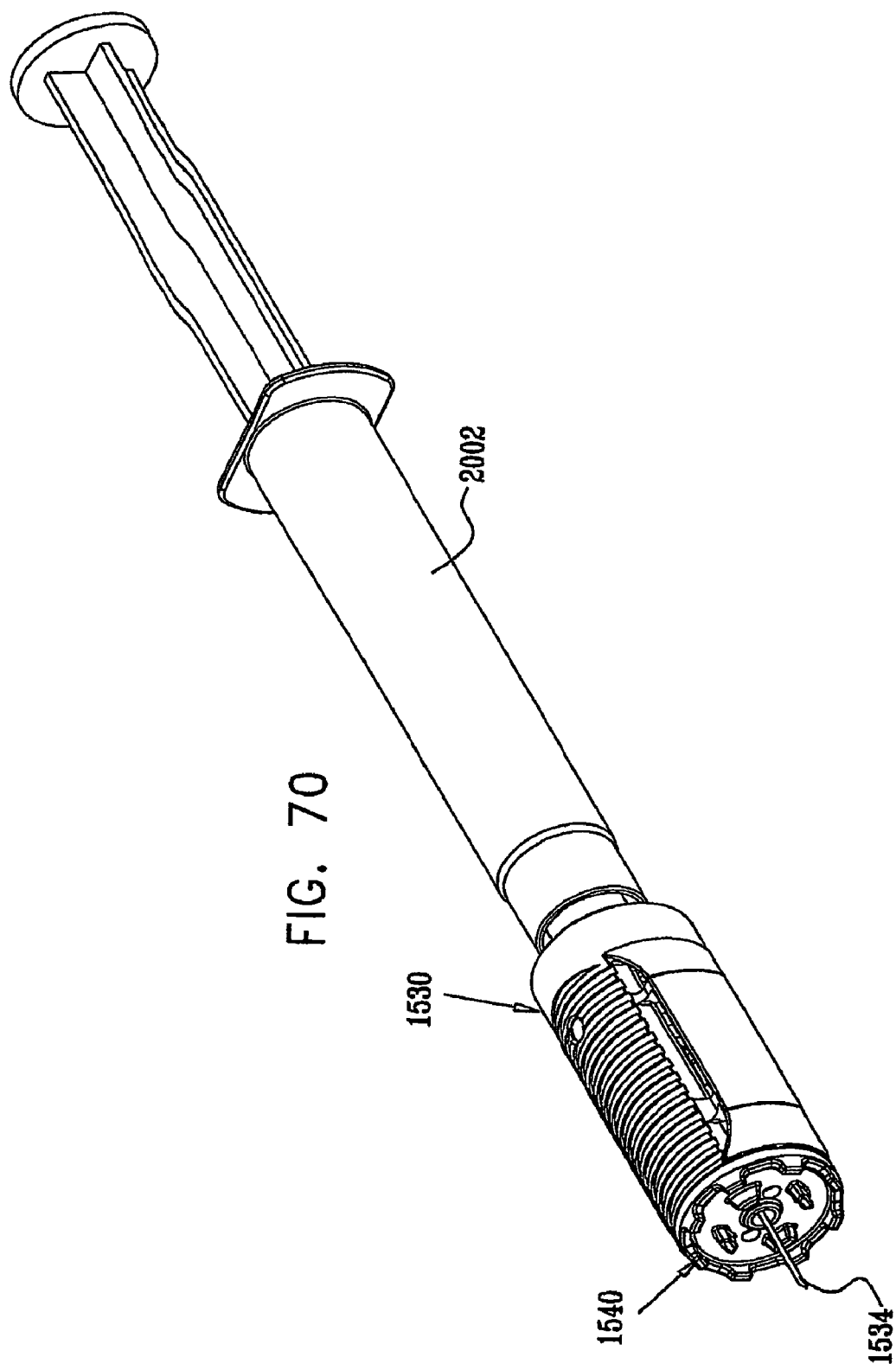
FIG. 70 is a simplified pictorial illustration of the automatic needle device of FIG. 63 in a needle actuated operational orientation.

Reference is now made to FIG. 70, which is a simplified pictorial illustration of the automatic needle device of FIG. 63 in an actuated operative orientation, to FIGS. 71A and 71B which are respective top and side view simplified planar illustrations thereof and to FIGS. 72A and 72B which are sectional illustrations taken along respective section lines and directions LXXIIA-LXXIIA and LXXIIB-LXXIIB in FIGS. 71A and 71B.

As seen particularly in FIG. 72A, under the urging of spring 1520, inner facing teeth 1824 slide out of apertures 1644 formed in the cylindrical walls of bore 1636, thus allowing the needle hub assembly 1530 to move axially forward and to provide needle penetration. The forward motion of needle hub assembly 1530 stops when protrusions 1812 and 1814 come into touching engagement with inwardly extending transverse ribs 1626 of the housing 1510. At this stage, drug delivery may take place in response to manual operation of a syringe 2002.

It is seen that the elastic tube 1536 is in a highly extended state.

Figure 73:
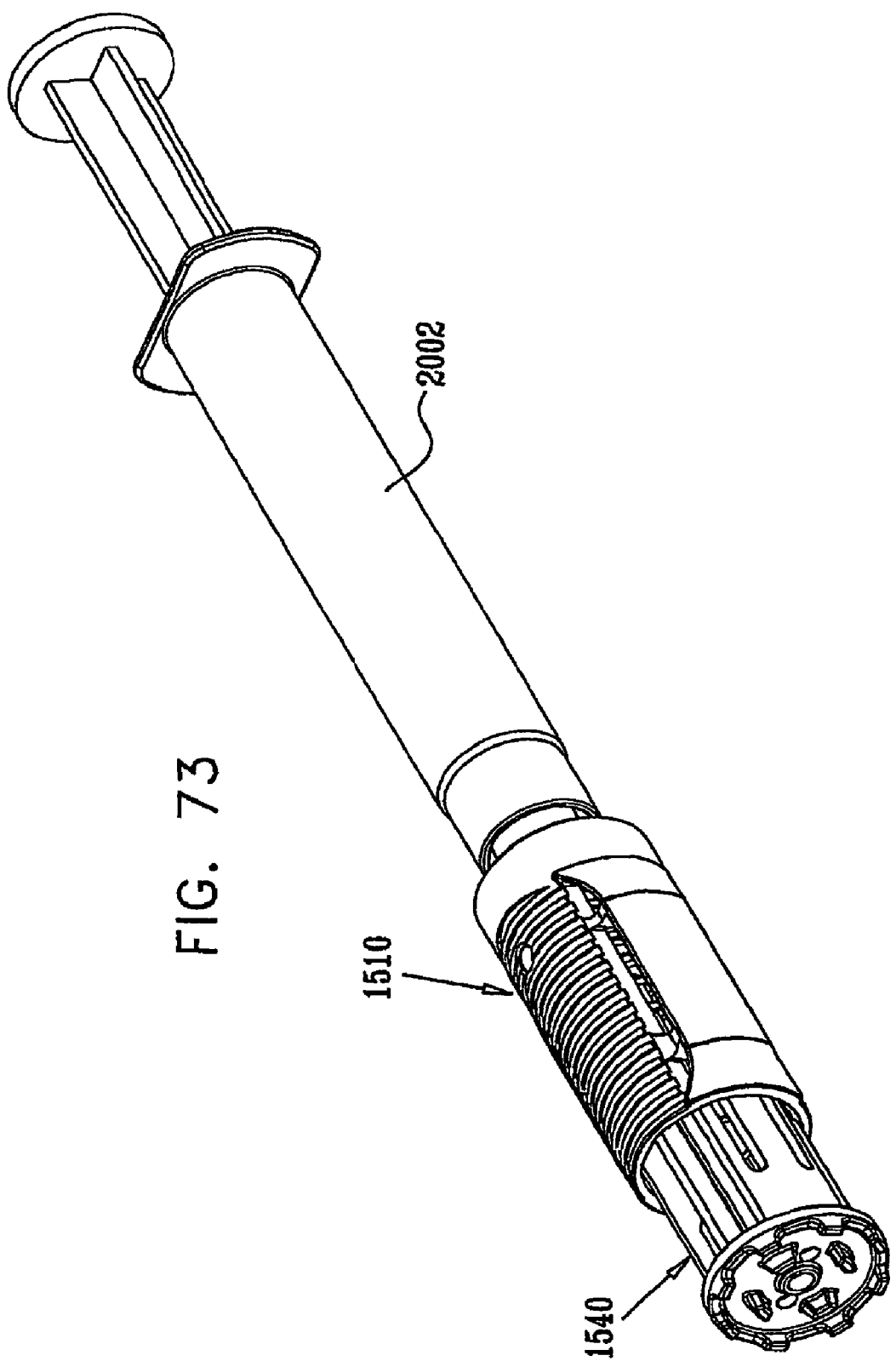
FIG. 73 is a simplified pictorial illustration of the automatic needle device of FIG. 63 in a post-drug delivery, needle guarded operative orientation.
Figure 74A:
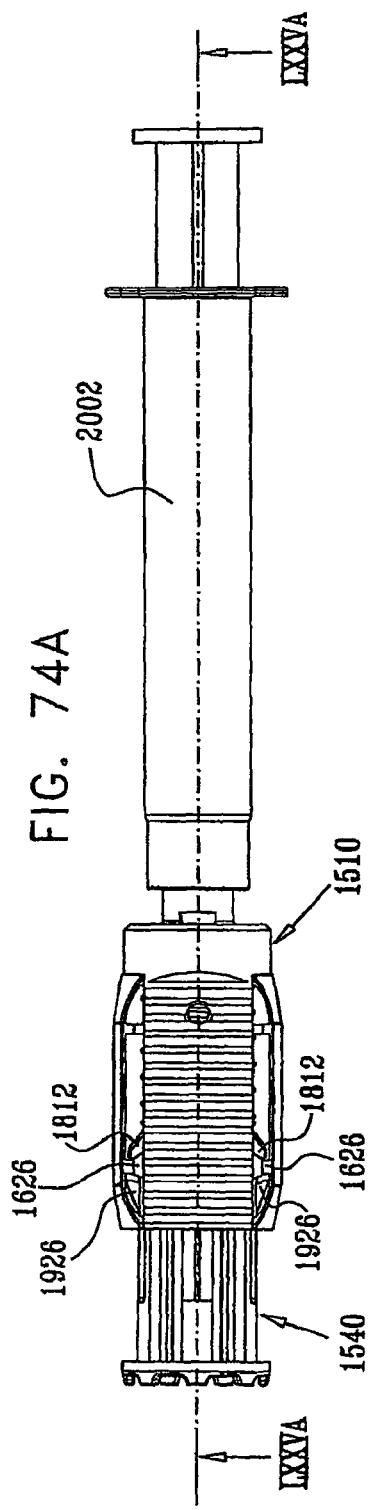
FIGS. 74A and 74B are respective top and side view simplified planar illustrations of the automatic needle device of FIG. 73.
Figure 74B:
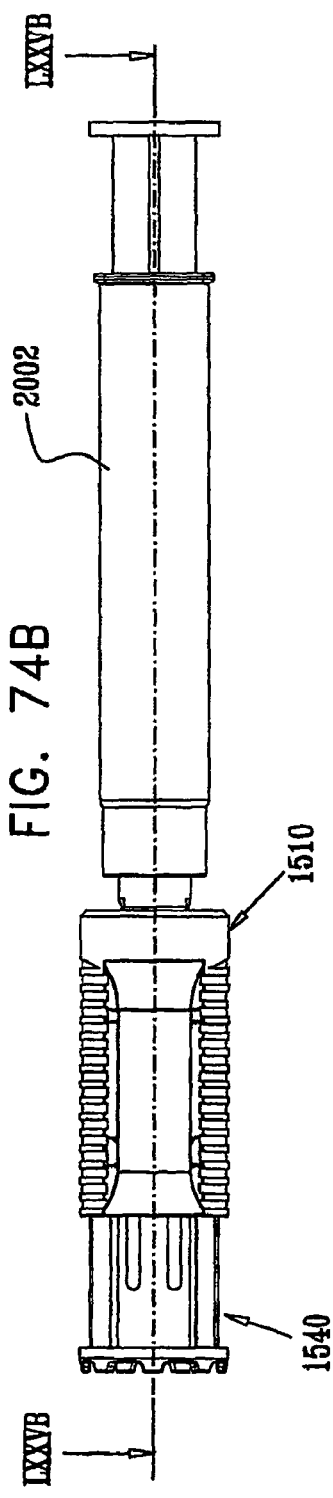

Reference is now made to FIG. 73, which is a simplified pictorial illustration of the automatic needle device of FIG. 63 in a post-drug delivery, needle guarded operative orientation, to FIGS. 74A and 74B, which are respective top and side view simplified planar illustrations thereof and to FIGS. 75A and 75B, which are sectional illustrations taken along respective section lines and directions LXXVA-LXXVA and LXXVB-LXXVB in FIGS. 74A and 74B.

FIGS. 73-75B illustrate the automatic needle device fully disengaged from the injection site and the needle guard 1540 fully extended under the urging of spring 1522 to fully enclose the needle 1534. The needle guard 1540 is prevented from moving farther forwards by engagement of curved rearward facing portions 1916 and 1918 and rearwardly extending surface 1830 of teeth 1826 of needle hub assembly 1530. The needle hub assembly 1530 is prevented from moving further forward by protrusions 1812 and 1814 leaning against inwardly extending transverse ribs 1626 of the housing 1510. The needle guard 1540 is prevented from moving rearwardly by outwardly facing tooth 1926 which snap-fits in front of inwardly extending transverse ribs 1626 of the housing 1510. Therefore, at this stage the needle guard 1540 is locked in place keeping the needle protected. It is seen that the elastic tube 1536 remains in a highly extended state. It is appreciated that the automatic needle device can be attached to various types of injection devices, and that the a luer adapter defined by an internal tapered surface of the tubular portion 110 of the housing element 10 of the automatic needle device may be readily modified for engagement with various injection devices such as pen injectors. It is also possible to integrate the automatic needle apparatus described herein into another injection device and thus to eliminate the need for a luer adapter.

It will be appreciated by persons skilled in the art that the present invention is not limited to what has been particularly shown and described hereinabove. Rather the scope of the present invention includes both combinations and subcombinations of various features described hereinabove as well as modifications of such features which would occur to a person of ordinary skill in the art upon reading the foregoing description and which are not in the prior art.

The invention claimed is:

1. An automatic needle device comprising:
   a housing element adapted to be connected to an external injection device;
   at least one needle bearing element adapted, when actuated, to be displaced with respect to said housing element from a non-penetration position to a penetration position; and
   a needle guard adapted for positioning with respect to said at least one needle bearing element in at least one mutually locked needle guarding orientation, whereby displacement of said needle guard relative to said housing causes corresponding displacement of said at least one needle bearing element.

2. An automatic needle device according to claim 1 and wherein:
   said at least one mutually locked needle guarding orientation comprises a first mutually locked needle guarding orientation; and
   said needle guard and said at least one needle bearing element are unlockable from said first mutually locked needle guarding orientation.

3. An automatic needle device according to claim 2 and wherein:

said at least one mutually locked needle guarding orientation also comprises a second mutually locked needle guarding orientation; and said needle guard and said at least one needle bearing element are lockable in said second mutually locked needle guarding orientation.

4. An automatic needle device according to claim 1 and wherein said needle guard and said at least one needle bearing element are lockable in said mutually locked needle guarding orientation from an unlocked orientation.

5. An automatic needle device according to claim 1 and also comprising a safety tab operative for disabling actuation of the automatic needle device.

6. An automatic needle device according to claim 2 and also comprising a resilient element and wherein movement of each of said needle guard and said at least one needle bearing element relative to said housing element loads said resilient element.

7. An automatic needle device according to claim 6 and wherein each of said needle guard and said at least one needle bearing element loads said resilient element independently of each other.

8. An automatic needle device according to claim 3 and wherein said needle guard comprises a first socket and a second socket, said first socket engaging said needle bearing element in a first, pre injection, operative orientation and said second socket engaging said needle bearing element in a second, post injection operative orientation.

9. An injection device comprising:
a housing element;
a unitary resilient element arranged to be located within said housing element, said unitary resilient element including a septum portion and at least one displacement actuating portion; and
at least one needle bearing element including a needle sealingly engaging said septum portion, said at least one needle bearing element adapted, when actuated, to be displaced by said at least one displacement actuating portion of said unitary resilient element with respect to said housing element from a non-penetration position to a penetration position.

10. An injection device according to claim 9 and wherein said housing element is adapted to be connected to an external injection device.

11. An automatic needle device according to claim 9 and also comprising a safety tab operative for disabling actuation of the automatic needle device.

12. An automatic needle device according to claim 9 and also comprising a needle guard adapted for positioning with respect to said at least one needle bearing element in at least one mutually locked needle guarding orientation, whereby displacement of said needle guard relative to said housing causes corresponding displacement of said at least one needle bearing element.

13. An automatic needle device according to claim 12 and wherein:
said at least one mutually locked needle guarding orientation comprises a first mutually locked needle guarding orientation; and
said needle guard and said at least one needle bearing element are unlockable from said first mutually locked needle guarding orientation.

14. An automatic needle device according to claim 13 and wherein:
said at least one mutually locked needle guarding orientation also comprises a second mutually locked needle guarding orientation; and
said needle guard and said at least one needle bearing element are lockable in said second mutually locked needle guarding orientation.

15. An automatic needle device according to claim 13 and wherein said needle guard and said at least one needle bearing element are lockable in said mutually locked needle guarding orientation from an unlocked orientation.

16. An automatic needle device according to claim 14 and wherein said resilient element engages said at least one needle bearing element and said needle guard.

17. An automatic needle device according to claim 16 and wherein movement of each of said needle guard and said at least one needle bearing element relative to said housing element loads said resilient element.

18. An automatic needle device according to claim 17 and wherein each of said needle guard and said at least one needle bearing element load said resilient element independently of each other.

19. An automatic needle device according to claim 12 and wherein said needle guard comprises a first socket and a second socket, said first socket engaging said needle bearing element in a first, pre injection, operative orientation and said second socket engaging said needle bearing element in a second, post injection operative orientation.

* * * * *